US009151744B2

(12) United States Patent
Pongrácz et al.

(10) Patent No.: US 9,151,744 B2
(45) Date of Patent: Oct. 6, 2015

(54) LUNG TISSUE MODEL

(75) Inventors: Judit Erzsébet Pongrácz, Hosszúhetény (HU); Domokos Bartis, Pécs (HU)

(73) Assignee: Pécsi Tudományegyetem, Pécs (HU)

( * ) Notice: Subject to any disclaimer, the term of this patent is extended or adjusted under 35 U.S.C. 154(b) by 89 days.

(21) Appl. No.: 13/289,097

(22) Filed: Nov. 4, 2011

(65) Prior Publication Data

US 2012/0045770 A1 Feb. 23, 2012

Related U.S. Application Data

(63) Continuation-in-part of application No. PCT/IB2010/051978, filed on May 5, 2010.

(60) Provisional application No. 61/410,023, filed on Nov. 4, 2010.

(30) Foreign Application Priority Data

May 5, 2009 (HU) .................................... 0900819
Nov. 4, 2010 (EP) .................................... 10462007

(51) Int. Cl.
*C12N 5/077* (2010.01)
*C12Q 1/02* (2006.01)
*G01N 33/50* (2006.01)
*C12N 5/071* (2010.01)
*G01N 33/574* (2006.01)

(52) U.S. Cl.
CPC .......... *G01N 33/5044* (2013.01); *C12N 5/0688* (2013.01); *C12N 5/0697* (2013.01); *G01N 33/5088* (2013.01); *G01N 33/57423* (2013.01); *C12N 2501/415* (2013.01); *C12N 2502/1323* (2013.01); *C12N 2502/28* (2013.01); *C12N 2503/04* (2013.01); *C12N 2533/90* (2013.01); *G01N 2500/00* (2013.01)

(58) Field of Classification Search
None
See application file for complete search history.

(56) References Cited

U.S. PATENT DOCUMENTS

| 2001/0055804 A1 | 12/2001 | Shekhar et al. |
| 2003/0109920 A1 | 6/2003 | Martins-Green et al. |
| 2004/0223952 A1* | 11/2004 | ten Have-Opbroek et al. ............ 424/93.2 |
| 2008/0112890 A1 | 5/2008 | Lelkes et al. |
| 2008/0274088 A1* | 11/2008 | Panoskaltsis-Mortari et al. ............ 424/93.7 |
| 2009/0325216 A1* | 12/2009 | Mayer ............ 435/29 |
| 2011/0052551 A1* | 3/2011 | Flaherty et al. ............ 424/93.7 |

FOREIGN PATENT DOCUMENTS

| WO | 2004/046322 A2 | 6/2004 |
| WO | 2008/100555 A2 | 8/2008 |
| WO | WO2009092092 | * 7/2009 |
| WO | WO2009108772 | * 9/2009 |
| WO | 2010/128464 A1 | 11/2010 |

OTHER PUBLICATIONS

Ong et al.Biomaterials 29 (2008) 3237-3244.*
Molnar et al.European Journal of Cardio-thoracic Surgery 37 (2010) 1402-1410.*
Pongracz et al. Respir. Res. Jan. 26, 2006;7:15, 1-10.*
Carterson et al. Infection and Immunity, Feb. 2005, p. 1129-1140.*
Molnar et al. European Journal of Cardio-thoracic Surgery 37 (2010) 1402-1410.*
Pongracz et al. Respir. Res. Jan. 26, 2006; 7:15, 1-10.*
Akri, G. et al., (2009). "Wnt pathway aberrations including autocrine Wnt activation occur at high frequency in human non-small-cell lung carcinoma." Oncogene 28, pp. 2163-2172.
Alcorn, J.L, et al., (1997). "Primary Cell Culture of Human Type II Pneumonocytes: Maintenance of a Differentiated Phenotype and Transfection with Recombinant Adenoviruses." Am. J. Respir. Cell Mol. Biol., 17(6): pp. 672-682.
Anderson, G. et al., (1993). "MHC class II-positive epithelium and mesenchyme cells are both required for T-cell development in the thymus. Nature." 4 362(6415):70-3.
Bartling, B. et al., (2006). "Proliferative stimulus of lung fibroblasts on lung cancer cells is impaired by the receptor for advanced glycation end-products." Am J Respir Cell Mol Biol. Jan;34(1):83-91. Epub Sep. 15, 2005.
Belinsky et al., (1992). "Role of the alveolar type II cell in the development and progression of pulmonary tumors induced by 4-(methylnitrosamino)-1-(3-pyridyl)-1-butanone in the A/J mouse." Cancer Res. 52 3164-3173.
Bellusci, S. et al. (1997). "Fibroblast growth factor 10 (FGF10) and branching morphogenesis in the embryonic mouse lung." Development. 124(23): 4867-4878.
Bruno, M.D. et al. (1995). "Lung cell-specific expression of the murine surfactant protein A (SP-A) gene is mediated by interactions between the SP-A promoter and thyroid transcription factor-1." J.Biol.Chem. 270: 6531-6536.
Cardoso, W.V. (2001). "Molecular regulation of lung development." Annu Rev Physiol. 63: 471-494.

(Continued)

*Primary Examiner* — Robert Yamasaki
(74) *Attorney, Agent, or Firm* — Jason D. Voight

(57) ABSTRACT

The present invention provides for an engineered three dimensional (3D) pulmonary model tissue culture which is free of any artificial scaffold.

26 Claims, 20 Drawing Sheets

(56) References Cited

OTHER PUBLICATIONS

Carterson, A.J. et al. (2005). "A549 lung epithelial cells grown as three-dimensional aggregates: alternative tissue culture model for *Pseudomonas aeruginosa* pathogenesis." Infect Immun. 73(2):1129-40.

Colvin, J.S. et al. (1999). "Genomic organization and embryonic expression of the mouse fibroblast growth factor 9 gene." Dev Dyn. 216(1): 72-88.

Colvin, J.S. et al. (2001). "Lung hypoplasia and neonatal death in Fgf9-null mice identify this gene as an essential regulator of lung mesenchyme." Development 128(11): 2095-2106.

De Moerlooze, L. et al. (2000). "An important role for the IIIb isoform of fibroblast growth factor receptor 2 (FGFR2) in mesenchymal-epithelial signalling during mouse organogenesis." Development 127(3): 483-492.

Deslee, G. et al. (2007). "Bronchial epithelial spheroids: an alternative culture model to investigate epithelium inflammation-mediated COPD" Respir Res. 8(1): 86.

Dobbs, L.G. (1989). "Pulmonary Surfactant. Annual Review of Medicine" 40, 431-446.

Fjellbirkeland, L. et al. (1996). "Nonadhesive stationary organ culture of human bronchial mucosa" Am. J. Respir. Cell Mol. Biol.; 15: 197-206. (abstract).

Foster, K.A. et al. (1998). "Characterization of the A549 cell line as a type II pulmonary epithelial cell model for drug metabolism." Exp Cell Res. 15;243(2):359-66.

Goodman, T.T. et al. (2008). "3-D tissue culture systems for the evaluation and optimization of nanoparticle-based drug carriers." Bioconjug Chem. 19(10):1951-9. Epub Sep. 13, 2008.

Guarino, M. et al. (2009). "Direct contribution of epithelium to organ fibrosis: epithelial-mesenchymal transition." Human Pathology, 40(10): p. 1365-1376.

Hare, K.J. et al. (1999). "In vitro models of T cell development. Seminars in Immunology" 11(1): p. 3-12.

Honig, M.G. et al. (1989). "DiI and diO: versatile fluorescent dyes for neuronal labelling and pathway tracing." Trends Neurosci. 12(9): 333-335.

Hughes, T. et al. (2007) "Why Use a Rat Lung?", a poster presented at National Center for Replacement, Refinement and Reduction of animals in Research, Showcasing the 3Rs Portcullis House, Feb. 28, 2007.

Ikeda, K. et al. (1995). "Gene structure and expression of human thyroid transcription factor-1 in respiratory epithelial cells." J. Biol. Chem. 270: 8108-8114.

Innovative Medicines Initiative (2008). "Innovative Medicines Initiative (IMI) Research Agenda" European Technology Platform.

Königshoff, M. et al. (2008). "Functional Wnt Signaling Is Increased in Idiopathic Pulmonary Fibrosis." PLoS One, 3(5): p. e2142.

Krause, D.S. et al., (2001). "Multi-Organ, Multi-Lineage Engraftment by a Single Bone Marrow-Derived Stem Cell." Cell, 105:369-377.

Kreda, S.M. et al. (2001). "Expression and localization of epithelial aquaporins in the adult human lung" Am. J. Respir. Cell. Mol. Biol. 24, 224-234.

Lako, M. et al. (1998). "Isolation, characterisation and embryonic expression of WNT11, a gene which maps to 11q13.5 and has possible roles in the development of skeleton, kidney and lung" Gene. 219(1-2):101-10.

Lazzaro, D. et al. (1991). "The transcription factor, TTF-1, is expressed at the onset of thyroid and lung morphogenesis and in restricted regions of the foetal brain." Development 113: 1093-1104.

Matute-Bello, G. et al. (2008). "Animal models of acute lung injury" Am J Physiol Lung Cell Mol Physiol 295: L379-L399.

Min, H. et al. (1998). "Fgf-10 is required for both limb and lung development and exhibits striking functional similarity to Drosophila branchless." Genes Dev. 12(20): 3156-3161.

Molnar, T.F. et al. (2010). "Tissue engineering and biotechnology in general thoracic surgery" Eur J Cardiothorac Surg. 37(6):1402-10.

Napolitano, A.P. et al. (2007). "Dynamics of the self-assembly of complex cellular aggregates on micromolded nonadhesive hydrogels." Tissue Eng. 13(8): 2087-94.

Neagu, A. et al. (2006). "Computational Modeling of Tissue Self-Assembly." Modern Physics Letters B 20: 1207-1231.

Nichols, J.E. eta al. (2008). "Engineering of a Complex Organ: Progress Toward Development of a Tissue-engineered Lung." Proc Am Thorac Soc,. 5(6): p. 723-730.

Ornitz, D.M. et al. (2001). "Fibroblast growth factors." Genome Biol. 2(3): 3005.

Seike, M., et al., (2009). "Epithelial to Mesenchymal Transition of Lung Cancer Cells." Journal of Nippon Medical Scool, 76(4): p. 181-181. (abstract).

Sekine, K. et al. (1999). "Fgf10 is essential for limb and lung formation." Nat Genet. 21(1): 138-141.

Shannon, J.M. et al. (2004). "Epithelial-Mesenchymal Interactions in the Developing Lung." Annual Review of Physiology 66: 625-645.

Sherbet, G.V., (2009). "Metastasis promoter S100A4 is a potentially valuable molecular target for cancer therapy." Cancer Letters, 280(1): p. 15-30.

Ulrich, M. et al. (1998). "Localization of *Staphylococcus aureus* in Infected Airways of Patients with Cystic Fibrosis and in a Cell Culture Model of *S. aureus* Adherence" Am. J. Respir. Cell Mol. Biol. vol. 19 No. 1 83-91.

Vertrees, R.A. et al. (2008). "Cellular differentiation in three-dimensional lung cell cultures." Cancer Biol Ther. Mar; 7(3): 404-12.

Vertrees, R.A. et al. (2009). "Development of a three-dimensional model of lung cancer using cultured transformed lung cells." Cancer Biol Ther. 8(4):356-65.

Voulgari, A. et al. (2009). "Epithelial-mesenchymal transition in cancer metastasis: Mechanisms, markers and strategies to overcome drug resistance in the clinic." Biochimica et Biophysica Acta (BBA)—Reviews on Cancer 1796, 75-90.

Wang, X.Q. et al. (2009). "Oncogenic K-Ras Regulates Proliferation and Cell Junctions in Lung Epithelial Cells through Induction of Cyclooxygenase-2 and Activation of Metalloproteinase-9" Molecular Biology of the Cell 20, 791-800.

Wardlaw, S.A. et al. (2002). "Transcriptional regulation of basal cyclooxygenase-2 expression . . . " Molecular Pharmacology, 62, 326-333.

Yang, M.G. et al. (2006). "The TTF-1/TAP26 complex differentially modulates surfactant protein-B (SP-B) and -C (SP-C) promoters in lung cells." Biochem Biophys Res Commun. 344(2): 484-490.

Zeisberg, M. et al. (2009). "Biomarkers for epithelial-mesenchymal transitions. The Journal of Clinical Investigation" 119, 1429-1437.

Zhang, X. et al. (2005). "Reciprocal epithelial-mesenchymal FGF signaling is required for cecal development." Development. 133: 173-180.

\* cited by examiner

A

B

LUNG TISSUE MODEL

This application is a continuation-in-part of International Application PCT/IB2010/051978, filed May 5, 2010, and also claims priority to U.S. provisional application 61/410,023, filed Nov. 4, 2010, which applications are incorporated by reference herein.

FIELD OF THE INVENTION

The present invention provides for an engineered three dimensional (3D) pulmonary model tissue culture which is free of any artificial scaffold. Three dimensional models of healthy lung tissue as well as disease tissues are available. The product according to the invention can be marketed e.g. in the form of tissue cultures, plates or arrays comprising such cultures or kits. The invention is applicable in medical and scientific research, for testing compounds for their effect on lung tissue, for screening, testing and/or evaluating drugs, and in certain cases in diagnostics of lung diseases.

BACKGROUND ART

Tissue engineering is a rapidly developing field of biomedical research that aims at repair, replace or regenerate damaged tissues. Due to the latest events of disastrous phase II clinical drug trials (e.g. TGN1412), further goals of tissue engineering include generation of human tissue models for safety and efficacy testing of pharmaceutical compounds. Tissue engineering in general and our model in particular exploits biological morphogenesis, which is an example of self-assembly.

Cell and tissue engineering is pursued nowadays from several perspectives. In one aspect, it is used to gain deeper insight into cell biology and physiology.
Three Dimensional Tissue Models Two main directions are being developed in tissue engineering research: tissue scaffold based and tissue scaffold free systems. While scaffold based systems use mostly biodegradable scaffold material to provide an artificial 3D structure to facilitate cellular interactions, a scaffold free system allows direct cell to cell interactions, and allows cells to grow on their secreted scaffold material in the model.

In US 2001/0055804 A1 ("Three dimensional in vitro model of human preneoplastic breast disease") discloses a three dimensional in vitro cell culture system useful as a model of a preneoplastic breast disease for screening drugs. Said model is prepared by co-culturing preneoplastic epithelial cells of breast origin, endothelial cells and breast fibroblasts on a reconstituted base membrane in a medium comprising further additives like growth factors, estrogens etc. Thus, in this solution a base membrane, preferably Matrigel® is used as a tissue scaffold. According to the description a network of branching ductal alveolar units vasculature is formed within about 3-7 days in this system.

The system relates to breast and not lung and there is no suggestion to make a lung culture by that method. In US 2003/0109920 ("Engineered animal tissue") microvascular endothelial cells were obtained from adult lung and placed between two layers of human dermal fibroblasts present in a three dimensional collagen gel. Thus, a sandwich structure was formed.

Though the vascular endothelial cells were obtained from human lung, the artificial tissue prepared by this method was similar to human skin, therefore, it can not be actually considered as a pulmonary tissue model. In US 2008/0112890 ("Fetal pulmonary cells and uses thereof") a 3D tissue-like preparation is taught which is based on fetal mouse epithelial, endothelial and mesenchymal cells. The authors used mouse embryonic lung cells to the preparation in order to obtain lung prosthesis and perform screening on the 3D tissue-like preparation. As a matrix, a hydrogel, MATRIGEL™ was used to establish appropriate cell-cell interactions. It appears from the description that a fibroblast overgrowth was experienced upon coculturing epithelial cells and fibroblasts.

WO2008/100555 ("Engineered lung tissue construction for high throughput toxicity screening and drug discovery") relates to a lung tissue model preparation comprising fetal pulmonary cells and a tissue scaffold made of a biocompatible material and preferably a fibroblast growth factor. Fetal pulmonary cells comprise epithelial, endothelial and mesenchymal cells. A number of applicable biocompatible materials are listed.

WO2004/046322 ("Replication of biological tissue") preparation of an artificial 3-D tissue is proposed under microgravity environment. The tissue is based on human breast cancer cells and is useful as a breast cancer model. In a rotating bioreactor chamber at first connective tissue cells are cultured till the formation of a 3-D spheroid structure, then sequentially endothelial and epithelial cells are added to the culture. It is to be noted that the teaching is theoretical and while protocols are provided to culture the cells and to handle to cultures, no actual results of the experiments are disclosed.

Vertrees, R A, Zwischenberger, J B et al. (2008) cultured mesenchymal cells (human bronchial tracheal cells) on collagen coated microporous cyclodextrin beads (Cytodex-3 micro carrier beads) in rotating walled vessels. After 24 to 48 h a malignant phenotype human epithelial cell line (BZR-T33) was added. The purpose of the authors was to develop a 3-D model of lung cancer. The authors observed that in the prior art primary cell lines "of human broncho-epithelial cells and human lung cancers provide a more differentiated model similar to the structure and function of epithelial cells in vivo; however, these models are short-lived in vitro."

Nichols, J. E. and Cortiella, J (2008) review recent advancements toward the development of a tissue-engineered lung and find that hitherto developed lung tissue models used specialized scaffold materials and were kept in culture lengthily. The authors mention that "[P]roblems to be faced in the development of . . . lung, depend on . . . the development of appropriate scaffolds and matrices to enhance and support three-dimensional (3D) production of tissues.

Molnar T. F. and Pongracz J. E. provide an overview of different applications of tissue engineering among others in lung tissue cultures. The authors note that "3D cultures . . . create additional problems, including difficulties of gas and nutrient exchange in the third dimension. To circumvent this problem, scaffolds . . . are purposefully engineered in a way to make tissue build-up and allow cellular interactions, nutrients and gas exchange to occur." They conclude, however, that "Biotechnology in reconstructive surgery is still a test-tube based laboratory issue . . . "

Scaffoldless designs are not envisioned in these two reviews.
Wnt Signaling and Wnt11

Wnt proteins are secreted morphogens that are required for basic developmental processes as well as maintenance of adult tissue homeostasis. In the lung, Wnt signaling controls proliferation, cell-fate decision, maturation and terminal differentiation of progenitor cells. Alveolar type II (ATII) cells are progenitors of alveolar type I (ATI) cells that create the primary gas exchange surface of the alveoli. However, how ATII type differentiation is regulated is still far from understood.

Wnt signaling regulates a variety of developmental processes [Dobbs, L. G. (1989)]. Over-expression (Wnt13 and Wnt2,4) or down-regulation (Wnt7a,5) of Wnts or Wnt pathway inhibitors (Dkk3,6, WIF7 and sFRP8), are characteristic in different types of pulmonary diseases including fibrosis and tumors. Additionally, over-expression of disheveled (Dvl), a signal transducer of Wnt signals, has been reported in 75% of NSCLC cases, highlighting the importance of Wnt pathways in pulmonary cancers.

At least three signaling pathways are involved in the signal transduction process: the canonical or β-catenin dependent, and two non-canonical pathways. Epithelial-mesenchymal transitition (EMT) is generally linked to increased β-catenin dependent signaling activity in many invasive or metastatic tumors [Voulgari, A. and Pintzas, A (2009); Zeisberg, M. and Neilson, E. G. (2009)]. Although β-catenin mutations in lung cancers are relatively rare, upregulation of uncomplexed β-catenin without genetic alteration to β-catenin itself has been shown in a high proportion of human NSCLCs [Akiri G. et al. (2009)]. β-catenin dependent signaling is also essential in pulmonary regeneration. Thus, a balance in Wnt levels seems to be essential to keep the healthy equilibrium in pulmonary homeostasis.

The shortcomings of non-human models in mimicking human tissue characteristics often compromise the success of understanding molecular interactions in human tissues. Recently, therefore primary human cells are frequently used in molecular studies. In traditional two dimensional cell cultures, however, primary cells loose their characteristic differentiation markers [Shannon, J. M., (1987)]. The present inventor have not information about any art study on the effect of Wnt11 in 3D model tissue cultures.

Despite the extensive literature of lung models, it appears that the prior art discloses only tissue scaffold based three dimensional models and no simple, tissue scaffold free lung tissue model, comprising at least epithelial cells and fibroblasts, is disclosed in the prior art.

The present Inventors have surprisingly found that by simple biochemical methods a tissue scaffold free lung tissue model system can be created which has certain morphological features of lung tissue and is in several aspects more favorable than two dimensional (2D) systems or systems based on a matrix. The model of the invention avoids the problem of fibroblast overgrowth. The present inventors also recognized and provide the first evidence that Wnt11 is a regulator of ATII type differentiation. Thus, due to the effect of Wnt11 the model can be further improved both in terms of marker expression and morphology. Wnt11 is also shown to be down-regulated in lung cancers (LCs). Thus, according to the invention a pulmonary cancer model is provided wherein expression of Wnt11 is down-regulated in the mesenchymal cells of the model tissue culture.

Moreover, the present Inventors recognized that Wnt11 is useful in repair and/or regeneration of tissue, preferably lung tissue after injury.

The pulmonary model tissue culture can be prepared rapidly. The present invention provides a model tissue which is ready for use in various tests. The model is suitable to study cell-cell interactions in various lung tissues to mimic normal function and disease development.

BRIEF DESCRIPTION OF THE INVENTION

The invention provides for an engineered three dimensional pulmonary model tissue culture, said model tissue culture having one or more of the following features, a) being free of an artificial tissue scaffold,
b) being composed of cultured cells or having a cultured cellular material wherein the cells are in direct cell-cell interaction with cells of one or more other cell types of the tissue material,
c) comprising at least cultured pulmonary epithelial and cultured mesenchymal cells, preferably pulmonary mesenchymal cells, preferably fibroblasts, wherein preferably the ratio of the pulmonary epithelial cells and the mesenchymal cells in the model tissue is at least 1:6, preferably at least 1:3, and at most 6:1, preferably at most 3:1,
d) having a morphology of one ore more cellular aggregate (s) wherein the surface of the aggregates is enriched in the pulmonary epithelial cells, or wherein the pulmonary epithelial cells and the mesenchymal cells, preferably fibroblasts are at least partially segregated in said aggregates, i.e. the ratio of epithelial cells on or at the surface of an aggregate is higher than in the inner or interior part of an aggregate, and/or the aggregates comprise a multiplicity of cavities,
e) wherein the epithelial cells express epithelial differentiation markers, preferably at least one alveolar type II (ATII) marker.

In a preferred embodiment said model tissue culture is obtainable by preparing a mixed suspension of at least pulmonary epithelial cells and mesenchymal cells, preferably fibroblast cells,
pelleting the cells of the suspension,
incubating the pelleted suspension in the presence of $CO_2$,
exposing the model tissue culture or the cells of the model tissue culture to a regulator of ATII type differentiation, preferably Wnt11,
and wherein
the model tissue culture comprises cuboid-like epithelial pulmonary cells, preferably the epithelial cells expressing at least one alveolar type II (ATII) epithelial differentiation marker show cuboid-like morphology. Preferably the ratio of cuboid-like epithelial pulmonary cells is at least 10%, 20%, 30%, 40%, 50%, 60%, 70%, 80% or 90% of the pulmonary epithelial cells or of the ATII type pulmonary cells.

In a preferred embodiment at least one type of cells of said model tissue culture express Wnt11; preferably said model tissue culture comprise alveolar epithelial cells or cells derived therefrom, said cells carrying a recombinant Wnt11 gene cloned for overexpression. In a preferred embodiment the gene of the Wnt11 protein is controlled by an inducible promoter.

In a further preferred embodiment the Wnt11 protein was added to cells of the model tissue upon culturing as a 3D culture.

a) In a preferred embodiment said model tissue culture is free of an artificial matrix material for providing a three dimensional environment to the cells. In an embodiment said model tissue culture is free of any artificial tissue scaffold material, either biodegradable or non-biodegradable tissue scaffold material, e.g. a porous three dimensional matrix; a three dimensional gel matrix. In an embodiment said model tissue culture is free of or does not comprise a microporous membrane support.

b) In a preferred embodiment said model tissue culture also comprises an extracellular matrix, the extracellular matrix proteins of which are secreted by at least one of the cell types comprising the tissue, preferably by fibroblasts.

c) In further preferred embodiments the pulmonary epithelial cells comprise at least one of the following cell types:
type I pneumocytes, [alveolar type I cells (ATI)]

type II pneumocytes, [alveolar type II cells (ATII)].

Preferably, said type II pneumocytes (alveolar epithelial cells with ATII characteristics) express one or more of the following markers: TTF1 transcription factor, surfactant protein A (SFPA), surfactant protein C (SFPC) and aquaporin 3 (AQP 3).

Preferably, said type I pneumocytes (alveolar epithelial cells with ATI characteristics) express one or more of the following markers: TTF1 transcription factor, aquaporin 3 (AQP 3), aquaporin 4 (AQP 4) and aquaporin 5 (AQP 5).

In various further embodiments at least one of pulmonary epithelial cells and pulmonary mesenchymal cells are present in the model.

Preferably, the cells are amphibian, reptilian, avian or, more preferably mammalian cells.

Preferred avian cells are poultry pulmonary cells.

Preferred mammalian cells are cells of herbivorous animals, preferably livestock animals like cells of e.g. sheep, goat, bovine cells, or rodent cells, e.g. rabbit or murine cells. Further preferred mammalian cells are those of omnivorous animals like pig cells. Highly preferred cells are human cells.

In further embodiments the pulmonary epithelial cells and/or the mesenchymal cells are obtained from
established cell lines, preferably from commercial sources,
healthy donors
patient donors.

In a preferred embodiment the cells are primary cells. In a preferred embodiment the cells are not de-differentiated cells or only partially de-differentiated cells.

In a further preferred embodiment the cells are de-differentiated cells or the cells are de-differentiated before culturing them to 3D model tissue culture.

In a preferred embodiment the pulmonary epithelial cells comprise small airways epithelial cells, preferably small airways epithelial cells with ATII characteristics.

In a further preferred embodiment the model tissue culture of the invention also comprises endothelial cells. In a preferred embodiment the endothelial cells are HMVEC or HUVEC cells.

Optionally, the model tissue culture of the invention may further comprise cells of further type selected from macrophages, mast cells, smooth muscle cells.

d) In a preferred embodiment the diameter of the cavities are or the average diameter of the cavities is at least 0.1, 0.5, 1, 2 or 5 nm, and at most 40, 60, 80, 100, 200, 500 or 1000 nm, typically vary between 1 to 200 nm or 2 to 100 nm.

Preferably, both epithelial cells and mesenchymal cells take part in the formation of said cavities, preferably in the formation of walls of the cavities. Preferably, the surface of the cavity wall is enriched in epithelial cells, similarly to the surface of the aggregate.

In a preferred embodiment, if the cells or the tissue culture is treated with a regulator of ATII type differentiation, preferably Wnt11, the size and or the density and or the number of cavities are increased in comparison with a control non-treated 3D culture.

In a preferred embodiment the average diameter or the typical diameter of the aggregate is at least 10 µm, 40 µm, 60 µm, 80 µm, 100 µm or 120 µm and the average diameter or typical diameter of the aggregate is at most 1000 µm, 800 µm, 600 µm, 500 µm, 400 µm or 300 µm.

Highly advantageously the average diameter or typical diameter of the aggregate is 100-300 µm, in a preferred embodiment it is about 200 µm.

Average size of the aggregates and average diameter of the cavities can be assessed and calculated or estimated by any experimentally and mathematically correct means. While the aggregates are essentially spherical in shape, it is evident that diameters for each aggregate multiple diameters can be determined due to a deviation from the exact sphere and depending on the position of the aggregate during measurement and on the measurement method. In case of cavities, e.g. tissue sections and imaging methods can be used for this purpose as exemplified herein. For example, smallest and largest diameter can be measured directly in the microscope measuring the size of several aggregates and averaged. Expediently, a microscope is used for this purpose.

In a preferred embodiment the majority of the aggregates, preferably at least the 60%, 70%, 80% or 90% of the aggregates has a diameter of at least 10 µm, 40 µm, 60 µm, 80 µm, 100 µm or 120 µm, and a diameter of at most 1000 µm, 800 µm, 600 µm, 500 µm, 400 µm or 300 µm, highly advantageously the diameter of the above ratio of the aggregates is 100-300 µm, in a preferred embodiment it is about 200 µm.

In a preferred embodiment, the culture samples in each aggregate or each container of a kit comprise cells in an amount of at least $10^3$, preferably at least $10^4$, more preferably at least $2*10^4$, $3*10^4$, $4*10^4$, $5*10^4$ cells, and at most $10^6$, more preferably at most $5*10^5$, $4*10^5$, $3*10^5$, $2*10^5$ or at most $10^5$ cells.

In a preferred embodiment the pulmonary epithelial cells and the fibroblasts are segregated based on a difference in their surface tension. Preferably, the majority of the pulmonary epithelial cells are located on the surface of the aggregate.

Preferably, the majority of the pulmonary epithelial cells form a pulmonary epithelial cell lining on the surface of the aggregate, preferably said pulmonary epithelial cell lining covering, at least partly, the surface of the aggregate.

In a further preferred embodiment the aggregates also comprise endothelial cells.

In a preferred embodiment the ratio of the endothelial cells, in comparison with the epithelial and fibroblast cells is higher in the center or central region of the aggregates that in the surface of the aggregates, or the ratio of the endothelial cells is increasing from the surface of the aggregates towards the center of the aggregates.

In a preferred embodiment the aggregates have a layered structure wherein the core or central region of the aggregates comprises the maximum ratio of endothelial cells, the intermediate layer or region of the aggregates comprises the maximum ratio of fibroblasts and the outer layer or surface layer of the aggregates comprises the maximum layer of epithelial cells.

e) In a preferred embodiment the epithelial differentiation markers expressed by the tissue cells of the engineered three dimensional pulmonary model tissue are at least one or more markers selected from the following group:
ATII type differentiation markers, preferably TTF1 transcription factor, cytokeratin 7, (KRT7), surfactant protein A (SFPA), surfactant protein C (SFPC) and aquaporin 3 (AQP 3)
and/or provided that ATI type cells are present
ATI type differentiation markers, preferably aquaporin 4 (AQP 4) and aquaporin 5 (AQP 5).

The markers expressed also depend on the cell type used in the tissue culture.

The level of any of the markers can be detected at mRNA or a protein level. Thus, the level of the marker may be mRNA level and/or protein level.

Preferably, the model tissue culture of the present invention at least one of the level of AQP3 (Aquaporin 3) and SFTPA (Surfactant protein A) is increased, i.e. they are up-reguated in comparison with a control 2D culture.

In a preferred embodiment, in the engineered three dimensional pulmonary model tissue culture
a) at least one alveolar epithelial cell (AEC) marker is up-regulated, and/or
b) at least one inflammation marker is down-regulated, and/or
c) epithelial-mesenchymal transition (EMT) is inhibited, and/or
d) at least one EMT marker is down-regulated,
in comparison with a control tissue culture selected from
a control 3D culture not exposed to a regulator of ATII type differentiation,
a control 2D culture not exposed to a regulator of ATII type differentiation,
a control 2D culture exposed to a regulator of ATII type differentiation.

In a further preferred embodiment in the engineered three dimensional pulmonary model tissue culture at least one of the following ATII markers are up-regulated:
a surfactant protein, preferably a surfactant protein selected from surfactant protein C (SFPC), pro surfactant protein C (pro-SFTPC), surfactant protein A (SFPA) preferably by at least 10%, 20%, 40%, 50%, 100% or 200%,
aquaporin 3 (AQP3), preferably by at least 20%, 50%, 100% or 200%,
thyroid transcription factor-1 (TTF1), preferably by at least 10%, 20%, 40%, 50% or 100%,
preferably in comparison with a control culture selected from
a control 3D culture not exposed to a regulator of ATII type differentiation,
a control 2D culture not exposed to a regulator of ATII type differentiation,
a control 2D culture exposed to a regulator of ATII type differentiation;
and/or
at least one of the following EMT markers is down-regulated:
S100 Ca binding protein A4 (S100A4),
N-cadherin,
snail homolog 2 (SLUG), preferably in comparison with a control tissue culture selected from
a control 3D culture not exposed to a regulator of ATII type differentiation,
a control 2D culture not exposed to a regulator of ATII type differentiation,
and/or
E-cadherin is up-regulated
in comparison with one or more control tissue culture as defined above.

Preferably, the model tissue culture of the present invention at least one inflammatory marker selected from IL1b, IL6 and CXCL8 is down-regulated, i.e. their level is decreased in 3D culture conditions in comparison with a control 2D culture.

Preferably, the model tissue culture of the present invention the level of at least one of de-differentiation markers S100A4 and N-cadherin is decreased in comparison with purified primary cells in 2D culture conditions or in a control 2D tissue culture.

In various further embodiments at least one of pulmonary epithelial cells and pulmonary mesenchymal cells are present in the model and, in analogy with embryonic lung development,
pulmonary epithelial cells secrete one or more fibroblast growth factors selected from FGF4, FGF8, FGF9.
pulmonary epithelial cells express on the cell surface FGFR2b receptors.
pulmonary mesenchymal cells, preferably fibroblasts secrete FGF7 and FGF10 and expresses FGFR1c and FGFR2c receptors.

In a preferred embodiment of the tissue culture of the present invention the ATII type differentiation markers and/or ATI type differentiation markers are expressed at a level higher, more preferably at a level of at least 10%, at least 20%, or at least 30% higher than that measured in a two dimensional tissue culture used as a reference.

Preferably, mRNA level(s) and/or protein level(s) of said epithelial marker(s) in the model tissue is higher than one or more or each of the control or reference cultures as defined above or
a two dimensional culture of the same cell types,
a culture of only pulmonary epithelial cells,
a culture of only primary fibroblast cells, preferably human fibroblast cells.

Preferably, the level of at least two of said markers is elevated.

In a preferred embodiment small airways epithelial cells are applied.

In a further preferred embodiment small airways epithelial cells showing at least some ATII type characteristics are applied. In this case the model tissue shows increased mRNA level(s) and/or protein level(s) of at least one or more markers selected from the following group of ATII type differentiation markers, e.g. those listed above. The engineered three dimensional pulmonary model tissue of the invention preferably shows a reduced expression of one or more pro-inflammatory cytokine and or one or more EMT markers.

Preferably, mRNA level(s) and/or protein level(s) of said on or more pro-inflammatory cytokine in the model tissue is lower than one or more or each of the following reference cultures
a two dimensional culture of the same composition of cells,
a culture of only pulmonary epithelial cells, wherein said pulmonary epithelial cells are treated analogously to the model tissue culture.

Preferably, the pro-inflammatory cytokine(s) are selected from the following group:
CXCL-8 pro-inflammatory cytokine, IL6, IL1a, IL1b, TNFalpha.

In a highly preferred embodiment the pro-inflammatory chemokine is CXCL-8 chemoattractant.

In a preferred embodiment the model tissue culture comprises pulmonary epithelial cells and pulmonary mesenchymal cells and does not comprise endothelial cells, wherein
the level of one or more of the following markers is increased relative to a control comprising non-cultured cells: E-cad, IL-1b and/or IL6,
the level of E-cad is increased relative to a control 2 dimensional culture,
the level of one or more of the following markers is decreased relative to a control 2 dimensional culture: IL-1b, CXCL8, IL6.

In a preferred embodiment the model tissue culture comprises pulmonary epithelial cells, pulmonary mesenchymal cells and endothelial cells, wherein
the level of one or more of the following markers is decreased relative to a control comprising non-cultured cells: E-cad, N-cad.
the level of E-cad is increased relative to a control 2 dimensional culture, the level of one or more of the following markers is decreased relative to a control 2 dimensional culture: N-cad, S100A4.

In a preferred embodiment the three dimensional pulmonary model tissue culture further comprises cells selected from the following group:
  endothelial cells, e.g. to mimic vasculature,
  macrophages,
  mast cells.
  At later stages the model can be extended using cell types:
  smooth muscle cells,
  nerve cells.

Disease Models

The invention also relates to an engineered three dimensional pulmonary model tissue culture wherein said model tissue culture
  a) is free of an artificial tissue scaffold wherein said artificial tissue scaffold is a porous three dimensional matrix; a three dimensional gel matrix or a porous membrane support,
  b) comprises cultured mesenchymal cells, preferably fibroblasts,
  c) comprises cultured pulmonary epithelial cells,
  d) has a morphology of one or more cellular aggregate(s), wherein the aggregates comprise a multiplicity of cavities, In the model tissue culture said epithelial and/or mesenchymal, preferably fibroblast cells comprise affected cells having a pathologic feature of a diseased lung tissue so that said model tissue culture is a pulmonary disease model tissue culture.

In preferred embodiments the disease involves a condition selected from inflammation, tumor, fibrosis, injury of a tissue and the model tissue culture is to be considered as an inflammatory model, a tumor model, a fibrosis model or a regeneration model, respectively.

In a preferred embodiment the engineered three dimensional pulmonary model tissue culture according to the invention Wnt11 is silenced, down-regulated or knocked-out in the cells of said model tissue culture, preferably in fibroblast cells, and thereby the model tissue culture shows EMT features typical of a tumor, preferably non-small cell lung carcinoma, more preferably adenocarcinoma.

Preferably the tumor model is a non-small cell lung cancer model.

Preferably the model culture expresses EMT markers typical of a tumor, preferably at least one of the following markers: S100A4, N-cadherin, SLUG, preferably, expresses at a higher level than a control culture wherein Wnt11 is not silenced, down-regulated and/or knocked-out.

In a preferred embodiment Wnt11 levels are down-regulated by transduction of the mesenchymal cells or of the epithelial cell of the model by siRNA. In the latter case e.g. a recombinant adenovirus can be used which does not infect fibroblasts.

Affected cells of the disease model can be but are not limited to cells obtained from patients (patient cells), cell lines which have a disease feature, e.g. tumor cell lines; cells exposed to an environmental effect, e.g. pro-inflammatory material, causing a disease feature; cells exposed to the effect of a mutagen and selected for a disease feature; or genetically modified cells transformed to express a protein or in which a gene is silenced so as to have a diseased feature.

In a preferred embodiment the cells are obtained from healthy subjects and disease state is induced therein. In this embodiment for example signaling of tumor induction or potential drug targets can be determined. In an other embodiment tumor model tissue is prepared from immortal cells, e.g. from malignously transformed or tumorous cells or cell lines. While in this embodiment no "healthy" control is present, this system is useful in drug testing as a sample contacted with a placebo drug provides a control for drug treatment samples.

In an embodiment tumorous cells are obtained from a patient, and efficiency of a projected therapy can be tested. Thus, the model tissue culture can be used for establishing personalized therapy.

Method for Preparation

The invention also provides for a method for the preparation of the engineered three dimensional pulmonary model tissue culture as defined herein, said method comprising the steps of
  preparing a mixed suspension of at least primary fibroblast cells and pulmonary epithelial cells,
  placing the mixed suspension or an aliquot thereof in a container suitable for pelleting the cells of the suspension,
  pelleting the cells,
  incubating the pelleted suspension in the presence of $CO_2$ for a time sufficient to the cells to form a three dimensional pulmonary model tissue comprising cellular aggregate(s),
  optionally assaying the model tissue for
  a) expression of one or more epithelial differentiation markers characteristic to lung tissue, and an increased expression level as compared to a suitable reference culture e.g. as disclosed herein, is considered as indicative of the formation of a three dimensional pulmonary model tissue culture; and/or
  b) expression of one or more pro-inflammatory cytokine, and a decreased expression level as compared to any suitable reference culture e.g. as disclosed herein, is considered as indicative of the formation of a three dimensional pulmonary model tissue culture, and/or
  c) at least one EMT marker, and a decreased expression level as compared to a suitable reference culture (as defined above) is considered as indicative of the formation of a three dimensional pulmonary model tissue culture, and/or
  d) morphology of the one or more aggregate(s).

In a preferred embodiment cells of the culture are exposed to/contacted with Wnt11, wherein preferably
  a) Wnt11 is added to the culture during culturing,
  b) a cell culture is provided wherein at least one type of cells, preferably epithelial or mesenchymal cells, are recombinant and overexpress Wnt11.

Preferably, the container is a non-tissue culture treated container.

Preferably, multiple aliquots are placed into multiple containers,

Preferably, the containers are wells of a plate, e.g. a 96 well plate or a 384 well plate, Preferably, pelleting is carried out at 200 g to 600 g, 1 to 20 minutes, preferably 2 to 10 minutes.

Preferably, the cells are supplied with a reporter molecule, e.g. are stained with a biocompatible dye to report on cellular features as disclosed herein.

The containers can be V-bottom, flat-bottom or U-bottom containers, depending on the purpose they are used for.

Upon preparation of a mixed suspension one or more type of cells are added to a container within 18 hours, preferably within 16 hours, 14 hours, 12 hours, 10 hours, 8 hours, 6 hours, more preferably within 4 hours, 3 hours, 2 hours, highly preferably within 1 hour or 0.5 hours. Preferably each type of cell used is added within the period defined above.

In a preferred embodiment the pelleted suspension is incubated in the presence of $CO_2$ for a period not longer than 50 hours, 40 hours, 30 hours, 24 hours, 22 hours, 20 hours, 18 hours, 16 hours, 14 hours, 12 hours or 10 hours. In a preferred embodiment the pelleted suspension is incubated in the presence of $CO_2$ for a period not less than 2 hours, 4 hours, 6 hours, 8 hours, 10 hours, 12 hours.

In an embodiment of the invention further type of cells are added to the mixed suspension of the cells. In an embodiment of the invention further type of cells are at least endothelial cells. In an embodiment of the invention further type of cells are selected from endothelial cells, smooth muscle cells, nerve cells, granulocytes, dendritic cells, mast cells, T/B lymphocytes, macrophages. Granulocytes, dendritic cells, mast cells, T/B lymphocytes and macrophages can be added to the cultures either in inactive or in immunologically active state. Optionally, the method according to the invention comprises de-differentiation of one or more type of cells prior to preparation of a mixed suspension.

Optionally, the method according to the invention comprises a propagation of one or more type of cells prior to preparation of a mixed suspension. This step is particularly required if parallel testing of a large number of samples are required, for example in HTS (High Throughput Screening) solutions.

Method for Screening

The invention also relates to a method for screening of a drug for its effect on lung tissue, said method comprising the steps of
  providing an engineered three dimensional pulmonary model tissue culture as defined herein,
  taking at least a test sample and a reference sample of said model tissue culture,
  contacting the test sample with a drug while maintaining the test sample and the reference sample under the same conditions,
  detecting any alteration or modification of the test sample in comparison with the reference sample wherein if any alteration or modification of the test sample is detected it is considered as an indication of the effect of the drug.

In certain variant of the method only the direction of an alteration or modification is observed and no physiological values are calculated. In certain variants a predetermined threshold value is defined based on a calibration curve and comparison is made with this value.

In a preferred embodiment the model tissue culture is the model of a healthy lung tissue and an adverse effect of a drug is tested, wherein alteration or modification which is detrimental to the cells of test sample is considered as a toxic or adverse effect of said drug.

In a preferred embodiment the model tissue culture is a pulmonary disease model tissue culture comprising affected cells having a pathologic feature and the beneficial effect of a drug is tested, wherein
  an assay to measure or assess said pathologic feature is provided for said model tissue culture to obtain a measure of disease,
  a reference sample of a healthy lung tissue (healthy reference sample) and/or a reference sample of a diseased lung tissue (diseased reference sample) is provided,
  the pathologic feature is measured or assessed in the healthy reference sample and/or in the diseased reference sample and in said at least one test sample before and after contacting it with the drug, wherein any alteration or modification in the test sample which shifts the measure of disease in the test sample towards the measure of disease in the healthy reference sample and or away from the measure of disease in the diseased reference sample is considered as a beneficial effect of said drug. In other words, it is more similar to the state of the healthy reference sample than to the diseased reference sample.

In a preferred embodiment primary cells obtained from a patient are applied. In a preferred embodiment primary cells from a given patient are not or only partly de-differentiated and used within 5, 4, 3. 2 or 1 day(s) or within 12, 10, 8, 6, 4, 3, 2, 1 hour(s) after obtaining them from said patient to prepare the mixed suspension of the cells. In a model tissue culture made of primary cells, features of the disease state of the given patient can be studied and therapeutic drugs and/or regimens can be tested.

Kits

The invention also relates to an engineered three dimensional pulmonary model tissue kit comprising a test plate having an array of containers wherein at least two containers contain
  samples of one or more types of engineered three dimensional pulmonary model tissue cultures as defined in any of the previous claims, each sample placed in separate containers of said plate,
  an appropriate medium for culturing cells of the model tissue cultures.

Preferably a subset of the containers comprises one or more control samples. Control samples can be pure cultures of certain cell types, e.g. cultures of epithelium and fibroblasts only, and/or two dimensional (2D) cultures. In disease models controls can be cultures of healthy cells.

Preferably, the engineered three dimensional pulmonary model tissue kit has one or more of the following characteristics:
  the plate is a 96 well plate.
  the plate is a V-bottom plate or a flat bottom plate or a plate comprising both V-bottom and flat-bottom wells.
  U-bottom plates also can be applied.
  the culture samples in each container comprise cells in an amount of at least $10^3$, preferably at least $10^4$, more preferably at least $2*10^4, 3*10^4, 4*10^4, 5*10^4$ cells, and at most $10^6$, preferably at most $5*10^5, 4*10^5, 3*10^5, 2*10^5$, or at most $10^5$ cells,
  the containers are sealed, either separately or together and contain a $CO_2$ enriched environment or atmosphere suitable for a lung tissue culture.
  the $CO_2$ enriched environment or atmosphere comprises
  at least 2%, 3%, 4% $CO_2$ environment,
  at most 10%, 9%, 8% or 7% $CO_2$ environment,
  highly preferably about 5% $CO_2$.

In preferred embodiments the samples comprise test sample(s) and corresponding control sample(s).

In preferred embodiments the test samples are present on a V-bottom plate or in V-bottom wells on a plate and the control samples are present on a flat-bottom plate or in flat-bottom wells on a plate.

The invention also relates to a Wnt11 protein for use in tissue repair, preferably lung tissue injury repair, healing of scars, alveolar tissue regeneration or in the treatment of a condition selected from lung tissue injury; pulmonary fibrosis, e.g. airway and interstitial pulmonary fibrosis, chronic fibrosis including asbestosis, sarcoidosis and idiopathic pulmonary fibrosis; pneumonitis, diseases causing airflow obstruction; chronic obstructive pulmonary disease (COPD).

The invention also relates to a method for alveolar tissue regeneration, lung tissue injury repair or in the treatment of a condition as defined above, in an amphibian, a reptile, a bird or in a mammal as defined above, said method comprising the steps of
providing Wnt11,
contacting cells of said mammal affected by said condition with the Wnt11 in an amount effective for amelioration of said condition.

In an embodiment the Wnt11 protein is provided in the form of a protein preparation, e.g. in the form of a spray, preferably an inhalable spray, an injection, an ointment or other formulation suitable to target lung tissue.

In an embodiment the Wnt11 protein is provided in a form of a cell therapy and said protein is expressed by recombinant cells, preferably by mesenchymal cell, e.g. mesenchymal stem cells, fibroblasts, epithelial cells, endothelial cells or other cell types as defined herein.

The invention also relates to a mammalian pulmonary cell comprising an expression cassette carrying a gene encoding a Wnt11 protein,
said cell being capable of expressing said Wnt11 protein.

In an embodiment, said cell is a primary fibroblast and the gene is introduced by a lentivirus vector.

In a further embodiment, said cell is an epithelial cell and the gene is introduced by a lentivirus vector or by an adenovirus vector.

Preferably, the gene of the Wnt11 protein is under the control of an inducible promoter as well known in the art.

Preferably, said cell is for use in alveolar tissue regeneration, lung tissue injury repair or in the treatment of a condition as defined above.

The invention also relates to the diagnosis of a lung cancer or carcinoma, preferably an NSCLC, preferably adenocarcinoma, wherein
a sample is provided from a patient (patient sample)
the level of level of Wnt11 and/or the receptor thereof, i.e. Frizzled 7 is assessed either at mRNA or at protein level,
the level assessed in the patient sample is compared to the level typical of a healthy subject, said level typical of a healthy subject either being obtained from a parallel control sample obtained from a healthy subject (healthy sample) or being determined as an average or threshold value from a multiplicity of healthy samples, wherein if the level of Wnt11 and/or the receptor thereof, i.e. Frizzled 7 is down-regulated in the patient sample relative to a level typical of a healthy subject the patient is considered as subject having or possibly having or being susceptive of a lung cancer or carcinoma, preferably an NSCLC, preferably adenocarcinoma.

Definitions

The meaning of an "artificial tissue scaffold" in the context of the present description is a solid support material useful for cell attachment and/or for assisting the structural three dimensional arrangement of cells, in tissue or cell culture. The structure of the artificial tissue scaffold is specially designed for these purposes. Preferably, said artificial tissue scaffold is manufactured prior to culturing of the tissue or cells and contacted with the tissue or the cells before or during culturing said tissue or cells. Thus, an artificial tissue scaffold is typically a cell growth support structure or material which contributes to the structure of the tissue or cell culture, e.g. the three dimensional structure thereof, by affecting at least a part of cellular interactions (e.g. the cell-cell interactions) or the cellular environment itself. As a consequence, if a tissue scaffold is removed from the tissue or cell culture, the tissue or cell culture will disintegrate or become disorganized.

The artificial tissue scaffold may be made of a biodegradable material. A skilled person will understand that degradation of the biodegradable material is not a removal of the tissue scaffold. In other words, if the biodegradable material scaffold is degraded gradually, allowing cell-cell interactions to be formed, this is not to be considered as a removal of the tissue scaffold and in this process the tissue or cell culture may not become disintegrated or disorganized.

In a version the artificial tissue scaffold is a three dimensional matrix, preferably a three dimensional gel matrix or a porous three dimensional matrix, said matrix preferably having microspaces or pores in which the cells are located.

In a version the artificial tissue scaffold itself is a support on the surface of which the cells are attached, preferably a porous membrane support. In this version of the scaffold it has a structure specially designed for and useful for cell attachment, e.g. a porous or curved or engrailed or grooved surface to which the cells are attached so that this facilitates the formation of a 3 dimensional structure.

Preferably, an artificial tissue scaffold
has a defined three dimensional structure
is a porous, preferably a highly porous material or matrix,
is a porous membrane,
is a porous three dimensional matrix
is made of a biocompatible material, and/or
is made of a polymer.

Optionally, the "artificial tissue scaffold" is a polysaccharide-based matrix, e.g. it is a cellulose-based matrix, e.g. a methyl-cellulose matrix.

Optionally, the "artificial tissue scaffold" has a bead structure. The bead structure "artificial tissue scaffold" may be e.g. a macroporous or a microporous bead, a bead coated with a matrix, e.g. a collagen matrix, e.g. a cytodex bead.

A "three dimensional tissue culture free of any artificial tissue scaffold" is understood herein as a tissue culture having a three dimensional structure wherein the three dimensional structure of said tissue culture is formed or contributed by inherent cell-cell interactions and is not assisted by an artificial tissue scaffold.

Thus, a three dimensional tissue culture free of any artificial tissue scaffold does not disintegrate or become disorganized in lack of an artificial tissue scaffold but maintains its three dimensional structure. Even if said three dimensional tissue culture free of any artificial tissue scaffold is cultured and formed on a solid support material, the formation of the three dimensional structure is not assisted by and is not due to attachment of cells to this solid support and it can be separated without destruction of the three dimensional structure.

"Segregation of cells" as used herein relates to the spatial separation of at least two types of cells of a tissue or cell culture, whereby after this spatial separation i.e. segregation, a region of the culture, e.g. a (partial) volume or surface, can be defined or found in which the ratio of the two types of cells is different from both the ratio of the same types of cells in the same region of the culture before segregation and the ratio of the same types of cells in an other region of the culture. Preferably, a difference in the surface tension of at least two types of cells significantly contributes to their segregation in vitro.

"Enrichment" of a region, e.g. a volume or partial volume or surface or partial surface of a culture in a certain cell type is to be understood as a phenomenon when the ratio of a certain cell type is higher in that region than in a reference region, e.g. an other region of said culture. Typically "enrichment" of a region of a culture is the result of segregation of cells.

"Inflammation" is an adaptive response that is triggered by noxious stimuli and conditions, such as infection and tissue injury.

A number of cytokines, known collectively as "pro-inflammatory cytokines" because they accelerate inflammation, also regulate inflammatory reactions either directly or by their ability to induce the synthesis of cellular adhesion molecules or other cytokines in certain cell types. The major pro-inflammatory cytokines that are responsible for early responses are IL1-alpha, IL1-beta, IL6, and TNF-alpha. Other pro-inflammatory mediators include IFN-gamma, CNTF, TGF-beta, IL12, IL17, IL18, IL8 (CXCL8) and a variety of other chemokines that chemoattract inflammatory cells, and various neuromodulatory factors. The net effect of an inflammatory response is determined by the balance between pro-inflammatory cytokines and anti-inflammatory cytokines (for example IL4, IL10, and IL13, IL16, IFN-alpha, TGF-beta, IL1ra, G-CSF, soluble receptors for TNF or IL6). Activation of IL1-beta by various caspases proceeds in a large multiprotein complex that has been termed inflammasome.

LIF, GM-CSF, IL11 and OSM are further cytokines affecting inflammation processes and which are possibly useful in the preparation of disease models of the invention.

To the contrary, "anti-inflammatory cytokines", like IL10, regulate inflammation processes so that they are inhibited or alleviated.

The "average diameter" of three dimensional tissues is taken as the aritmetic mean of several measurements of three dimensional tissue diameters generated by the above described method.

The "typical diameter" (median diameter) is the diameter which marks the division of a given sediment sample into two equal parts by weight, one part containing all aggregates larger than that diameter and the other part containing all aggregates smaller.

An "array" of containers is to be understood as an arrangement of multiple containers of the same size, shape and material. The arrangement can be for example a sequence of container or a two dimensional matrix of the containers.

Viruses are obligate intra-cellular pathogens that infect cells, often with great specificity to a particular cell type. "Recombinant virus vectors" are modified viruses wherein certain genes are deleted and genes of interest added to the viral genome. The recombinant viral vectors can transduce the cell type they would normally infect. "Cancer" is a class of diseases in which a group of cells display uncontrolled growth, invasion (intrusion on and destruction of adjacent tissues), and sometimes metastasis (spread to other locations in the body via lymph or blood). These three malignant properties of cancers differentiate them from benign tumors, which are self-limited, do not invade or metastasize. 95% of lung tumors are bronchogenic carcinoma; also bronchial carcinoids, mesenchymal, miscellaneous neoplasms.

"Fibrosis" is the formation or development of excess fibrous connective tissue in an organ or tissue as a reparative or reactive process, as opposed to a formation of fibrous tissue as a normal constituent of an organ or tissue. Pulmonary fibrosis is a severe chronic disease characterized by a loss of elasticity and lung epithelial cells, replaced by interstitial myofibroblasts and deposition of extracellular matrix proteins in the lung interstitium leading to pulmonary structural remodelling.

"Cavity" is understood herein as space that is surrounded by something, in particular by cells or cellular tissue. In particular a cavity in accordance with the invention is a natural hollow or sinus or lumen within, i.e. inside or in the interior of an aggregate of the model tissue culture. The multiplicity of cavities provides as structure of the aggregate which may be considered as porous.

The term "walls of a cavity" is understood herein as tissue parts bordering and/or surrounding and/or, in their entirety, encompassing the lumen. Thickness of the wall can be defined in multiple ways as the context requires. For example it can be considered as composed of the surface layer or layers of the cells. Alternatively, it can be considered as a tissue part having a given finite thickness.

"Comprising" something is to be understood herein as including something and possibly further things as well. E.g. comprising a component does not exclude that further components or other materials are present.

If a composition, e.g. a tissue or tissue culture is "composed of" certain components it means that said components are essential, i.e. take part in forming said composition; preferably, they are structural components; it is possible, of course, that further components are present which are not mentioned after said term. For example, if a tissue or tissue culture is composed of one or more types of cells, these cells are essential in forming of said tissue, i.e. without any of these component cells the tissue or tissue culture would be a different type of tissue or tissue culture; however, this does not exclude that further cells or cell types may be present, even as components, in certain variants.

"Exposing the model tissue culture" or "exposing cells of the model tissue culture" to a substance is understood herein as providing conditions under which cells of the culture are contacted with said substance. Preferably, it is understood that the substance is added to the culture in any form, e.g. in isolated form, e.g. in a a supernatant or in a purified form, or that a cell recombinantly expressing said substance is added to the culture and optionally is co-cultured with the culture.

Panel A: mRNA levels of TTF-1 in 3D human lung microtissues. TTF1 transcription factor is a characteristic marker of alveolar epithelial cells. While 3D fibroblast cultures show no TTF1 expression, TTF1 is present in 3D SAEC monocultures and increased in 2D SAEC/NHLF co-cultures indicating the beneficial effect of fibroblasts. The highest level of TT1 expression was reached in 3D SAEC/NHLF tissues.

Panel B: mRNA levels of AQP-3 water transporter in 3D human lung micro-tissues. AQ3 is an ATII epithelial type marker in the lung. While 3D fibroblast cultures show no AQ3 expression, AQ3 is present in 3D SAEC monocultures and increased in 2D SAEC/NHLF co-cultures indicating the beneficial effect of fibroblasts, but the highest level of AQ3 was still observed in 3D SAEC/NHLF tissue cultures.

Panel C: Expression of Wnt11 and Surfactant Protein-A mRNA in various lung cell cultures. A gel image of a representative RT-PCR reaction is shown. Top panel: Wnt11 expression; Middle panel: Surfactant protein-A (SFTPA) expression; Bottom panel: beta-actin was used as internal control. Wnt11 is detected only when fibroblasts are present in the sample regardless of 2D or 3D culture conditions. However, Wnt11 levels are markedly higher in 3D mixed and NHLF-only cultures compared to respective 2D cultures. Note, that the presence of fibroblasts is required for SFTPA expression in epithelial cells and the level increases in 3D cultures.

Panel D: Relative mRNA expression level changes were measured in lung epithelium sorted from 2D and 3D cultures. Diagram bars represent fold changes of mRNA expression levels in 3D cultures compared to that of in 2D cultures. AQP3: Aquaporin 3; TTF-1: Thyroid transcription factor-1 (Nkx 2.1); E-cad: E-cadherin; N-cad: N-cadherin. Note the increased AQP3, TTF-1 and E-cad levels and the decreased N-cad levels in 3D cultures compared to that of in 2D cultures. One representative diagram is shown of three independent experiments.

Figure 5:
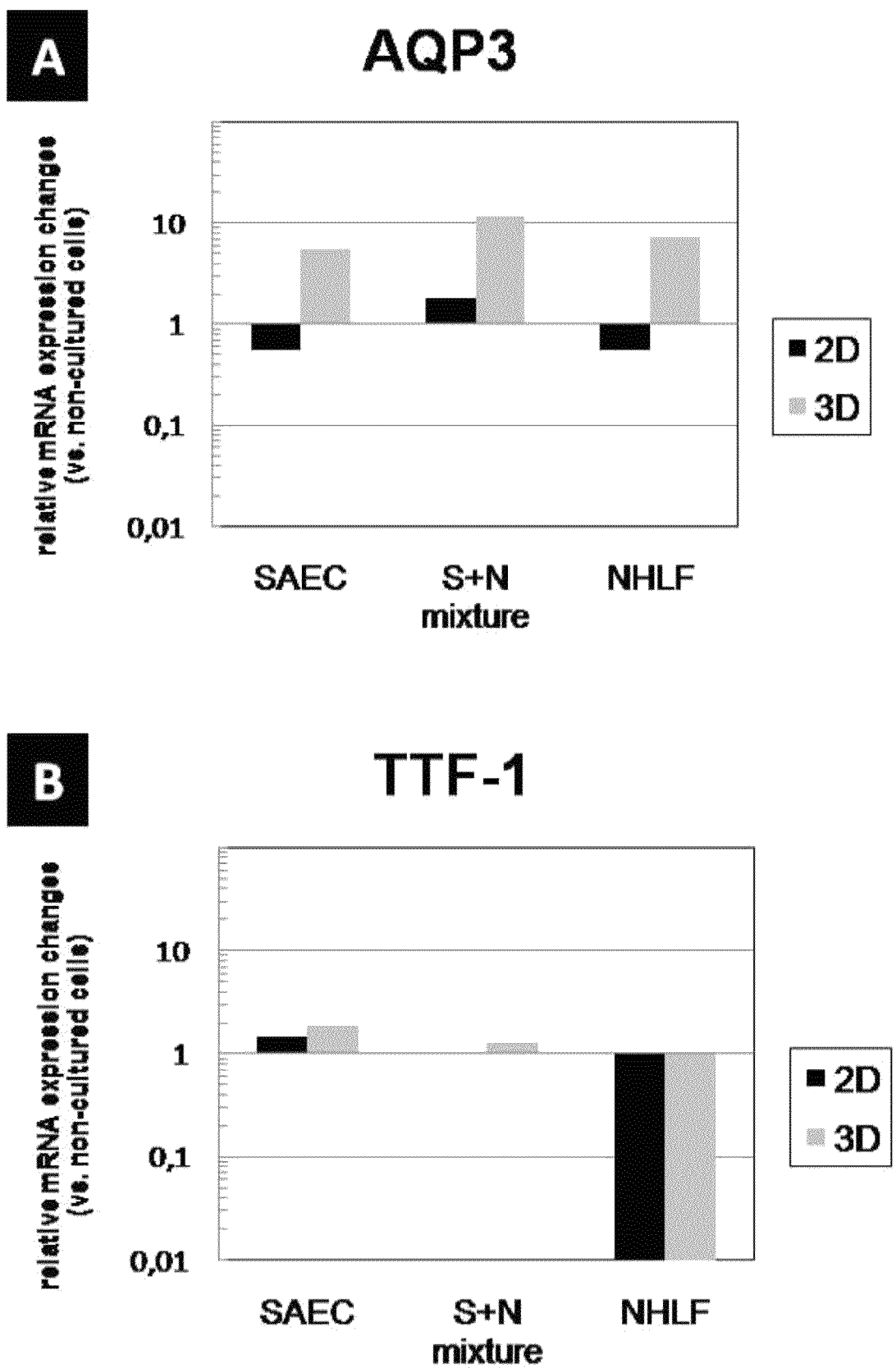
Figure 5:
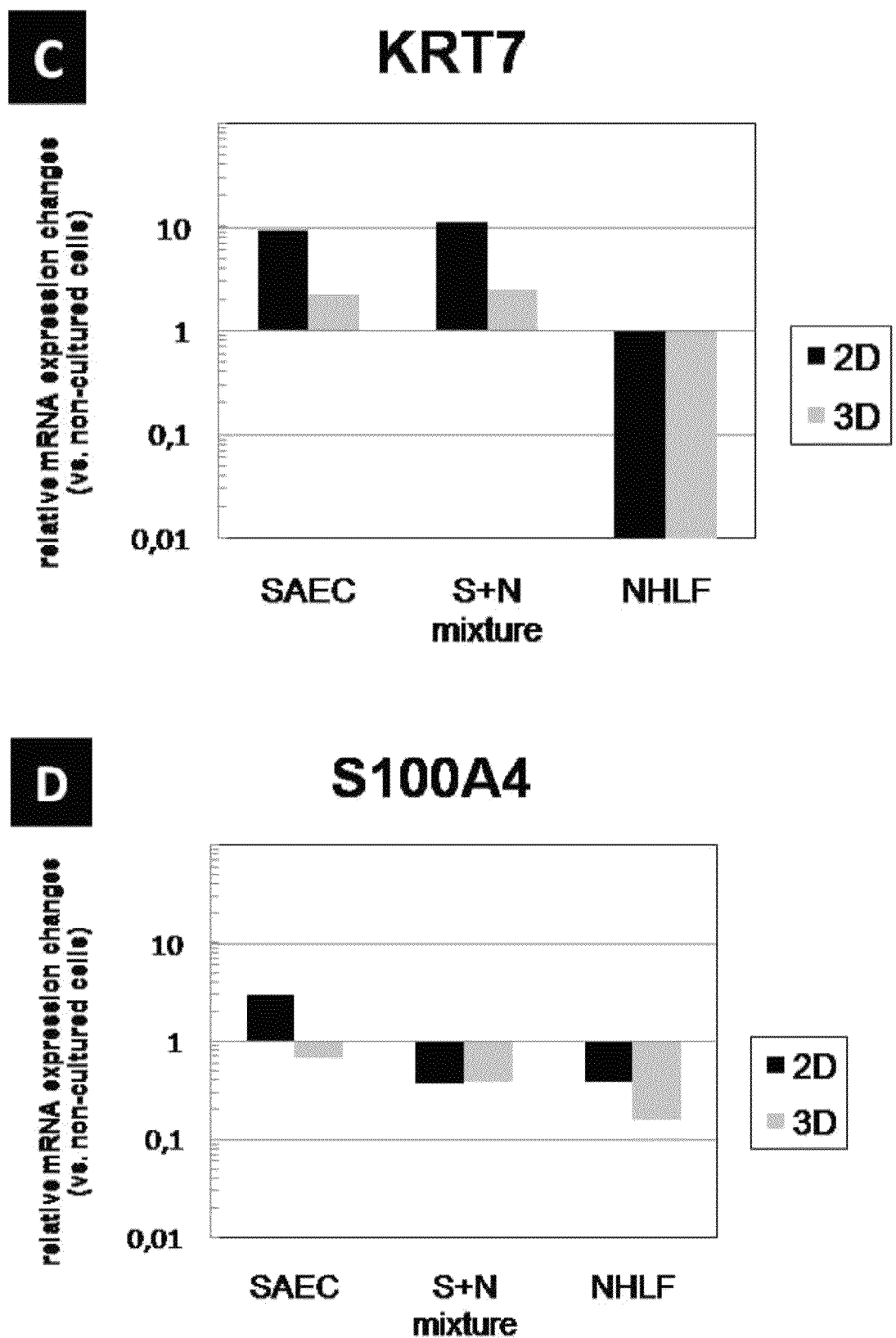
Figure 5:
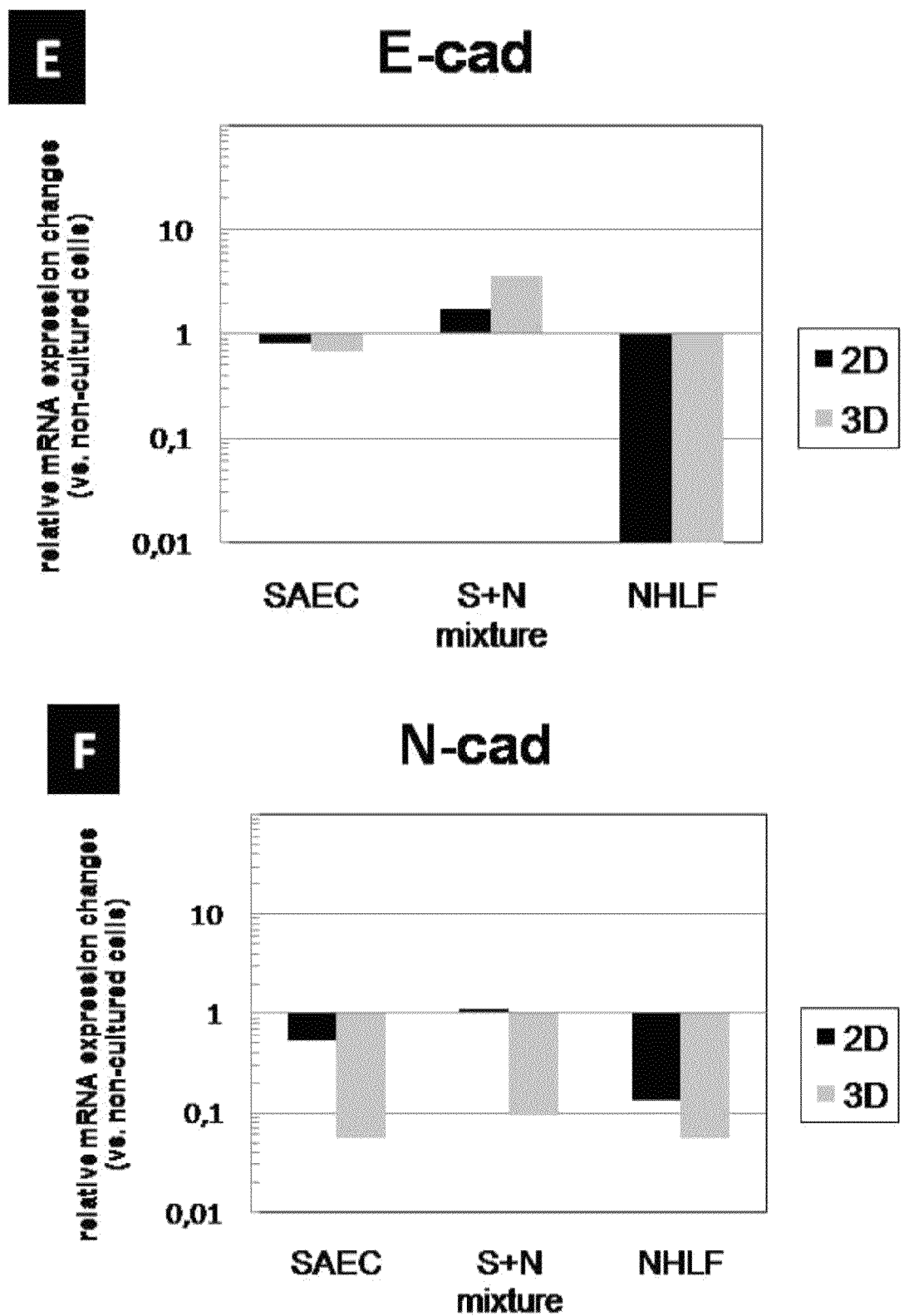

FIG. 5. Reative mRNA expression of different genes upon different culture conditions in lung cells.

Panels A-F: Pure or mixed Small Airway Epithelial cells (SAEC) and Normal Human Lung Fibroblasts (NHLF) were cultured as 2D monolayers or 3D micro-tissues for 72 hours, then cDNA were prepared for qRT-PCR. The gene expression levels are depicted on the diagrams as fold changes compared to "zero samples" representing pure or mixed cells at 0 hours, right before the set-up of 2D or 3D cultures. Abbreviations: S+N mix: 50-50% mixture of SAEC and NHLF cells; AQP3: Aquaporin 3; TTF -1: thyroid trancription factor-1 (Nkx2.1); KRT7: cytokeratin-7; S100A4: calcium-binding protein S100A4; E-cad: E-cadherin; N-cad: N-cadherin. Diagrams show representatives of 3 independent experiments with similar results. Primary lung cells used in cultures were originated from random donors of different sexes and ages in all samples.

AQP3 and KRT7 are SAEC differentiation markers (Panels A and C).

TTF1 transcription factor is a characteristic marker of alveolar epithelial cells (Panel B).

S100A4, E-cad and N-cad are EMT markers (Panels D, E and F).

Figure 6:
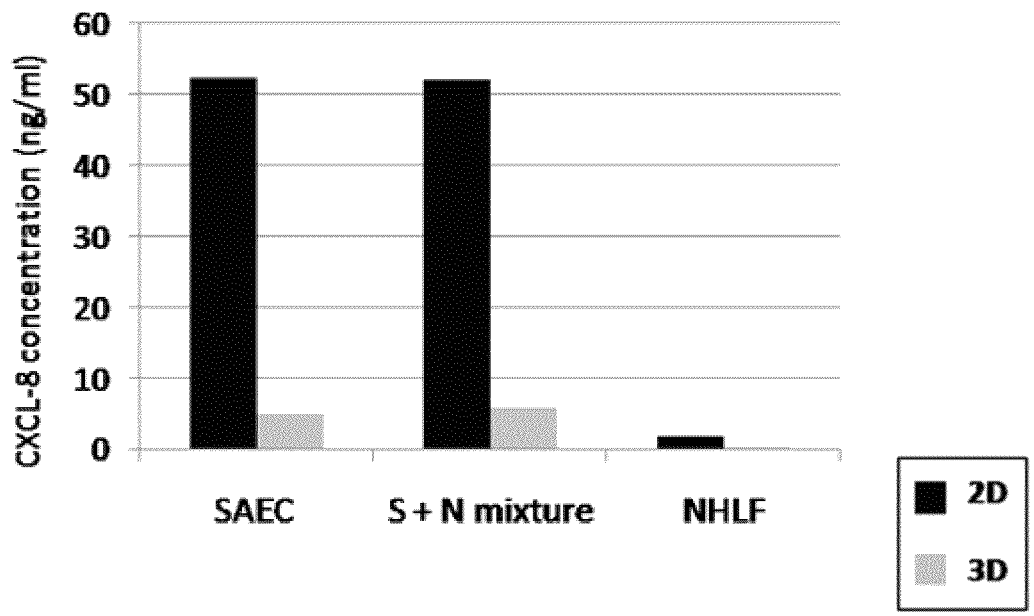
Figure 6:
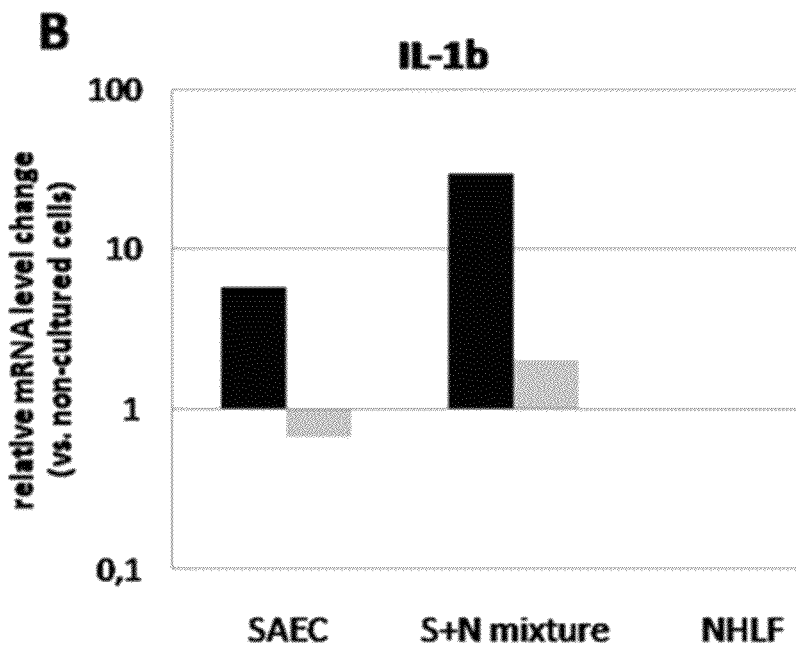
Figure 6:
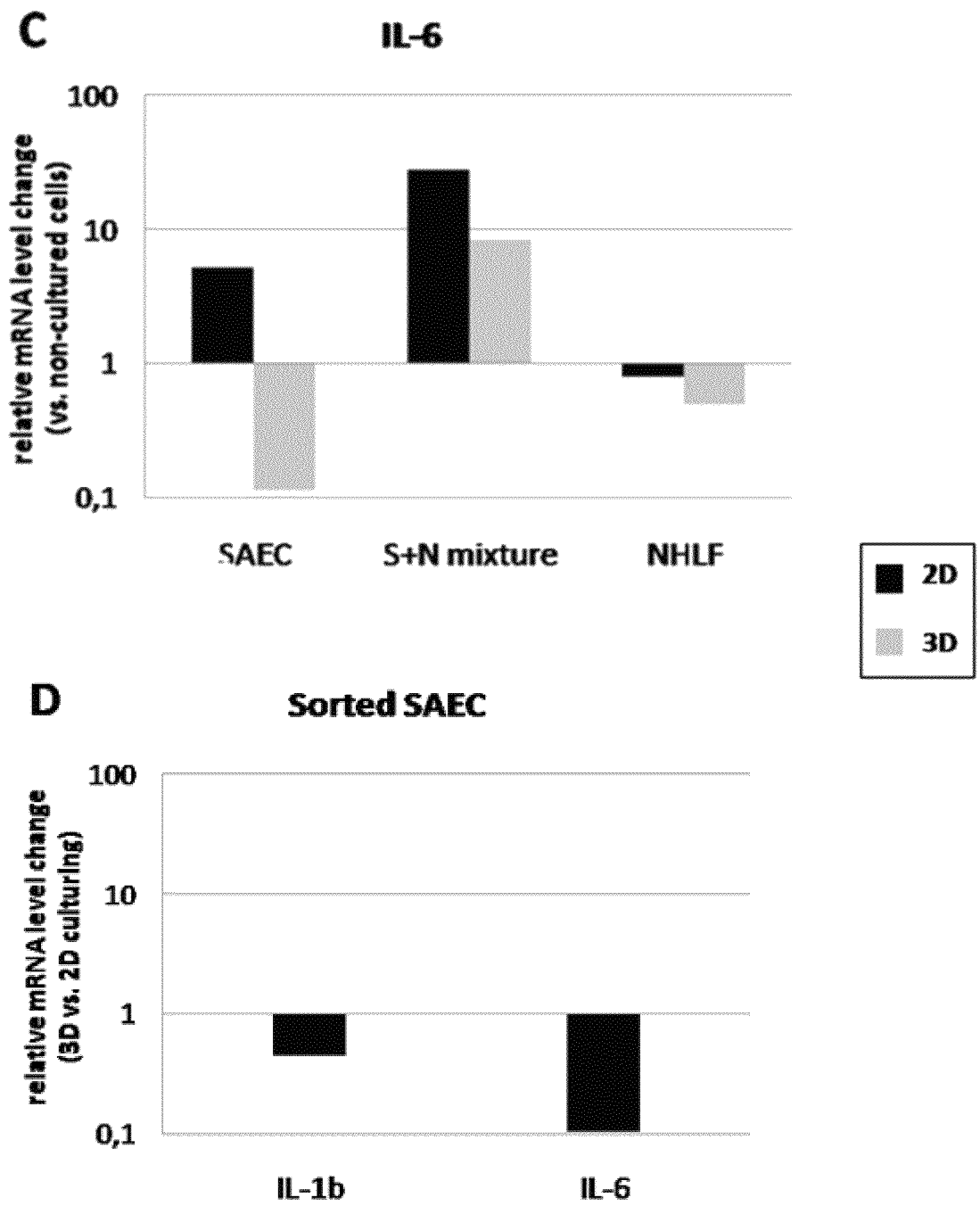

FIG. 6 Inflammatory cytokine and chemokine secretion in human primary lung cell cultures.

Panel A: CXCL-8 secretion of 2D and 3D NHLF monocultures was barely detectable in cell culture supernatants. 3D SAEC cultures still produced CXCL8, although to a lesser degree than 2D SAEC cultures. 2D co-cultures didn't significantly alter CXCL-8 expression, indicating, that the presence of fibroblasts cannot influence cytokine expression. CXCL-8 expression levels were significantly reduced in 3D tissue systems in both pure SAEC and SAEC-NHLF co-cultures.

Panels B and C: Expression levels of IL-1b and IL-6 mRNA in human primary lung cell cultures, respectively. Compared to 2D cultures, inflammatory mRNA levels of inflammatory cytokines IL-1b and IL-6 are consistently lower in 3D cultures. In pure fibroblast cultures IL-1b mRNA expression was not detectable, while IL-6 levels were much lower and the expression changes were also less prominent. (See also Table 2)

Panel D: Similarly to mixed cell culture samples, inflammatory cytokines IL-1b and IL-6 levels also decreased markedly in SAEC purified from 3D cultures, than that of 2D cultures. Data shown are means of three (Panels A-C) or two (Panel D) independent experiments. Purified primary lung cells used in all our experiments originated from random donors.

Figure 7:
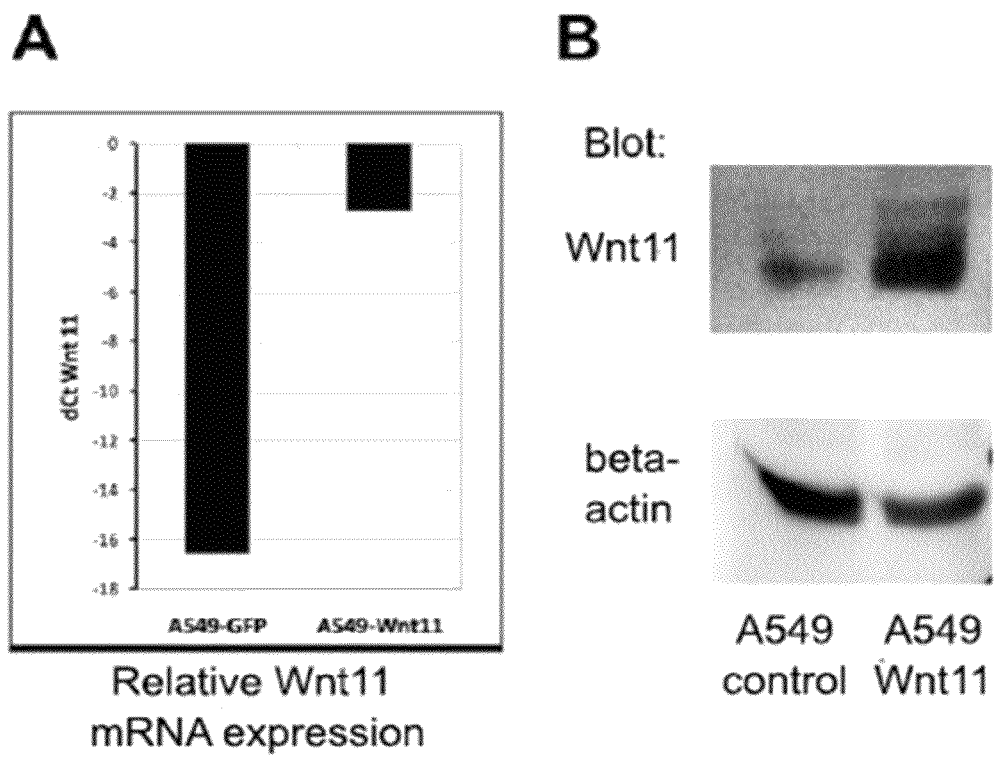
Figure 7:
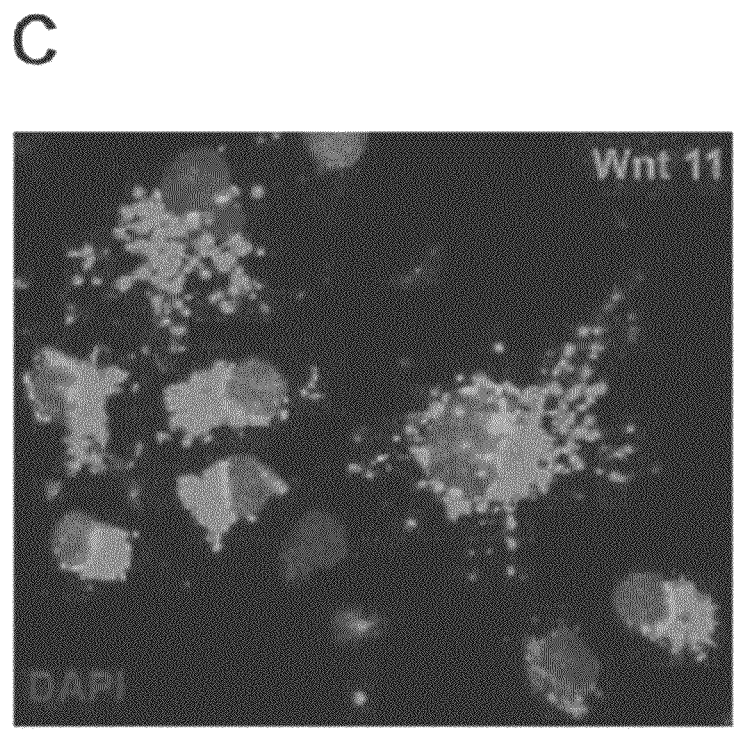

FIG. 7. Construction of Wnt11 overexpressing A549 cells. A549 pulmonary adenocarcinoma cells were transfected with a lentiviral bicistronic construct encoding full-length Wnt11-IRES-GFP. Control A549 cells were transfected with GFP only.

Panel A: Quantitative RT-PCR measurement of Wnt11 mRNA levels in A549-GFP and in A549-Wnt11 cells. dCt values shown on the diagram were calculated according to the formula $dCt = Ct_{Wnt11} - Ct_{b\text{-}actin}$.

Panel B: Detection of Wnt11 protein by Western blotting. Top: Wnt11 blots; Bottom: beta actin blots. Beta-actin was used as an internal loading control. Expression level in Wnt11 transgenic cells are markedly higher than in control cells.

Panel C: Wnt11 staining of Wnt11 over-expressing A549 cells. Wnt11 signal is shown in the red, DAPI nuclear staining in the blue channel.

Figure 8:
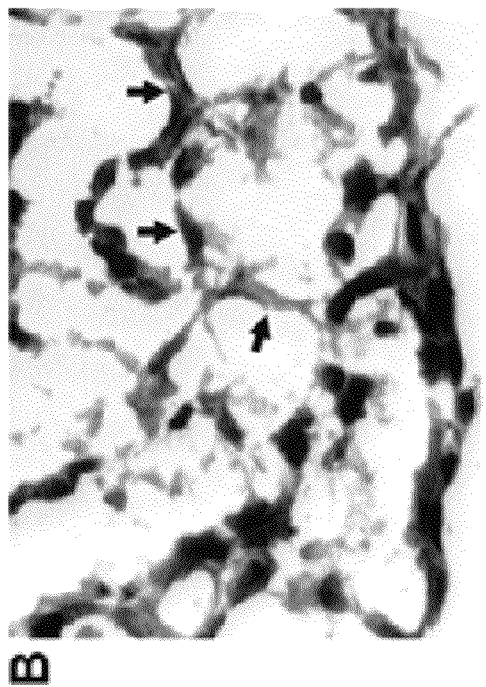
Figure 8:
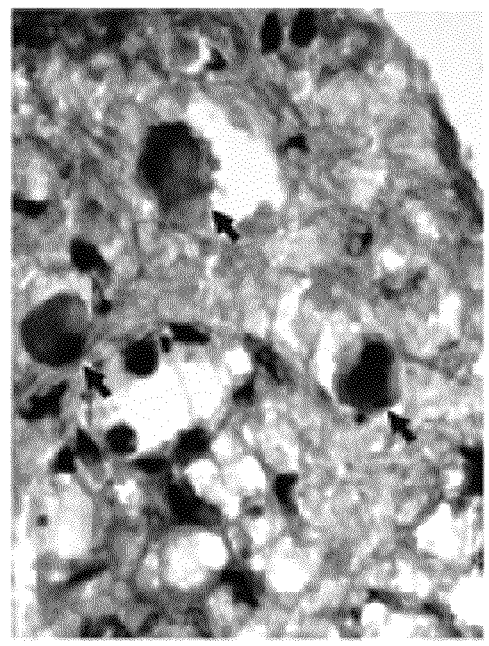
Figure 8:
Figure 8:
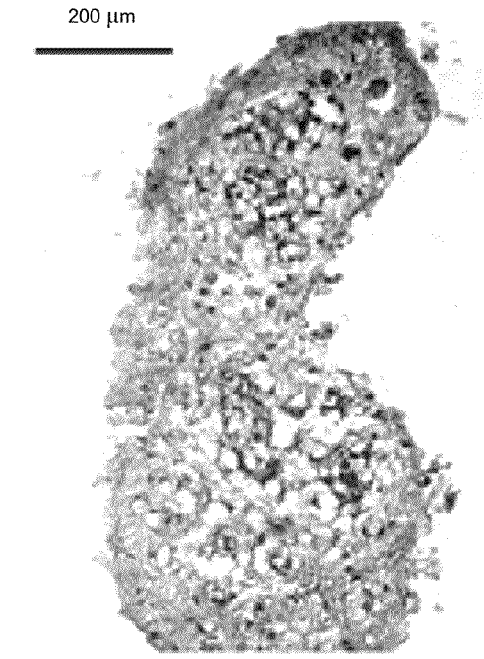
Figure 8:
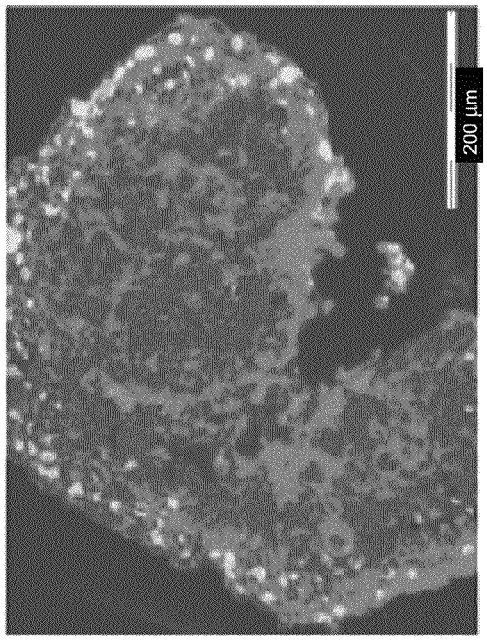
Figure 8:
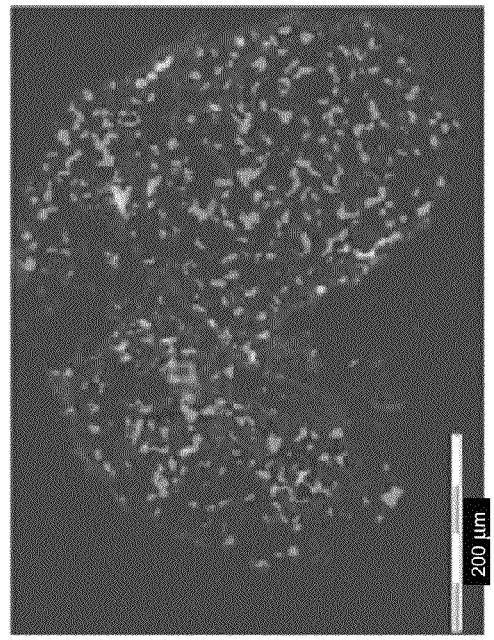
Figure 8:
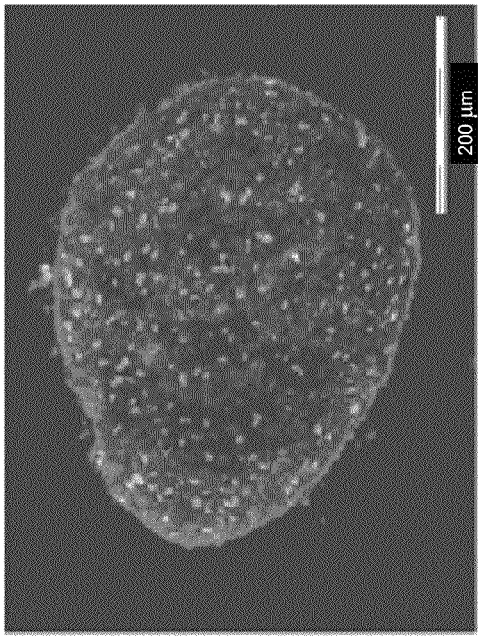
Figure 8:
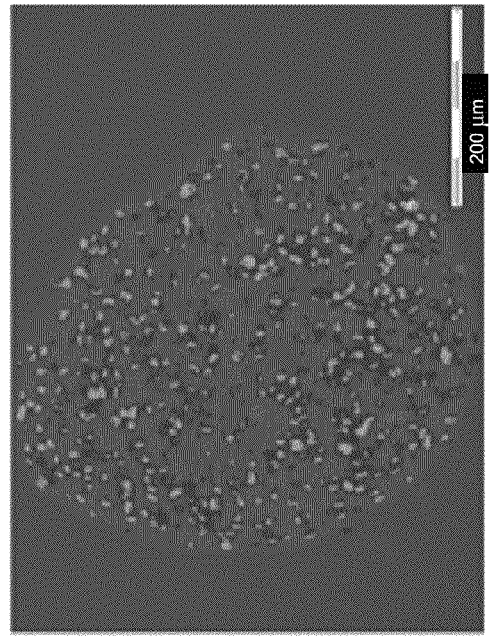
Figure 8:
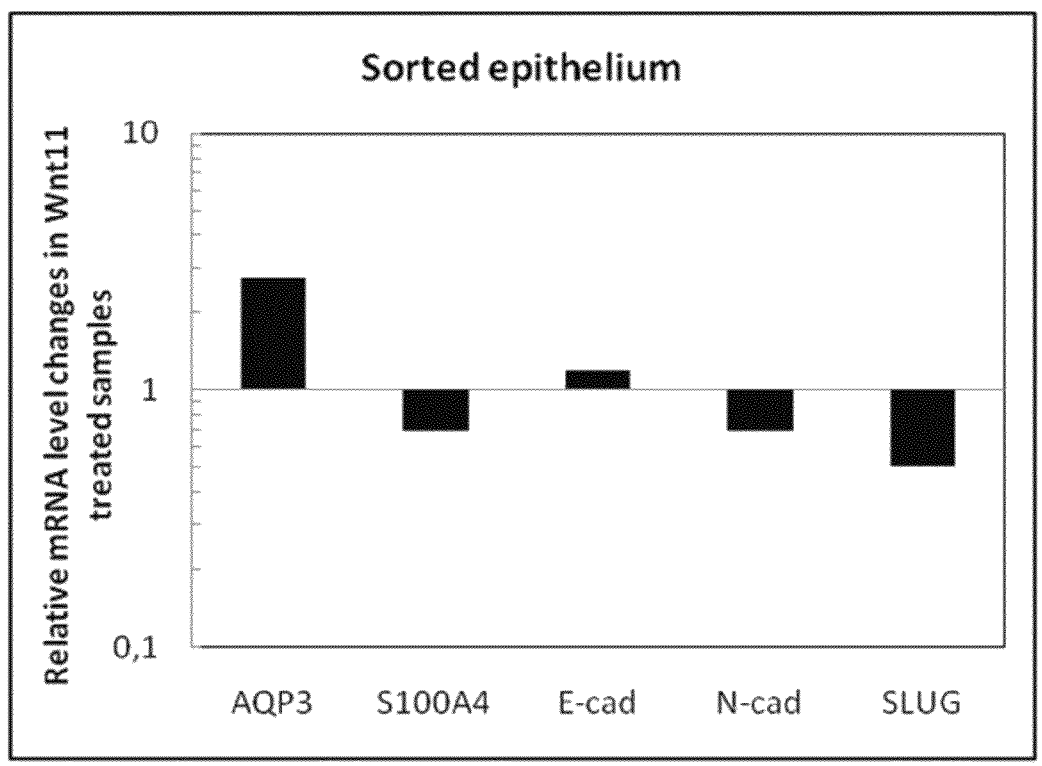

FIG. 8. Effects of Wnt11 treatment on lung micro-tissue model.

Panels A and B: Haematoxilin-eosin (HE)-stained sections of samples treated for 72 hours with control supernatant (SN). Panel A: 10× image, bar represents 200_m. Panel B: 40× HE stained image. Note the flat morphology of epithelial cells (arrows) and the porous structure.

Panels C and D: HE-stained sections of samples treated for 72 hours with Wnt11 SN. Panel C: 10× HE stained image, bar represents 200_m; Panel D: 40× HE stained image. Note the characteristic cuboid cells morphologically resembling ATII cells (arrows) and the cuboid epithelial cells.

Panels E and F: Immunofluorescent staining for ATII marker Pro-surfactant protein-C (pro-SFTPC) in control and Wnt11 SN-treated samples, respectively. Note the dramatic increase of pro-SFTPC expression in the Wnt11 SN treated sample (Panel F) compared to that of in the control SN treated sample (Panel E).

Panels G and H: Immunofluorescent staining for ATII marker Aquaporin-3 in control and Wnt11 SN-treated samples, respectively. Note the undetectably low expression of Aquaporin-3 (Panel G) in the control SN-treated sample compared to that of in Wnt11 SNtreated sample (Panel H).

Panel I: Relative mRNA level changes were measured in lung epithelium sorted from 3D cultures treated with control or Wnt11 SN. Diagram bars represent fold changes of mRNA expression levels in Wnt11 SN-treated samples compared to that of in control SN-treated samples. AQP3: Aquaporin 3; S100A4: calcium-binding protein S100A4; E-cad: E-cadherin; N-cad: N-cadherin; SLUG: SNAI2 transcription factor. Note the increased AQP3, and E-cad levels and the decreased S100A4, N-cad and SLUG levels in the presence of excessive Wnt11. One representative diagram is shown of three independent experiments.

Figure 9:
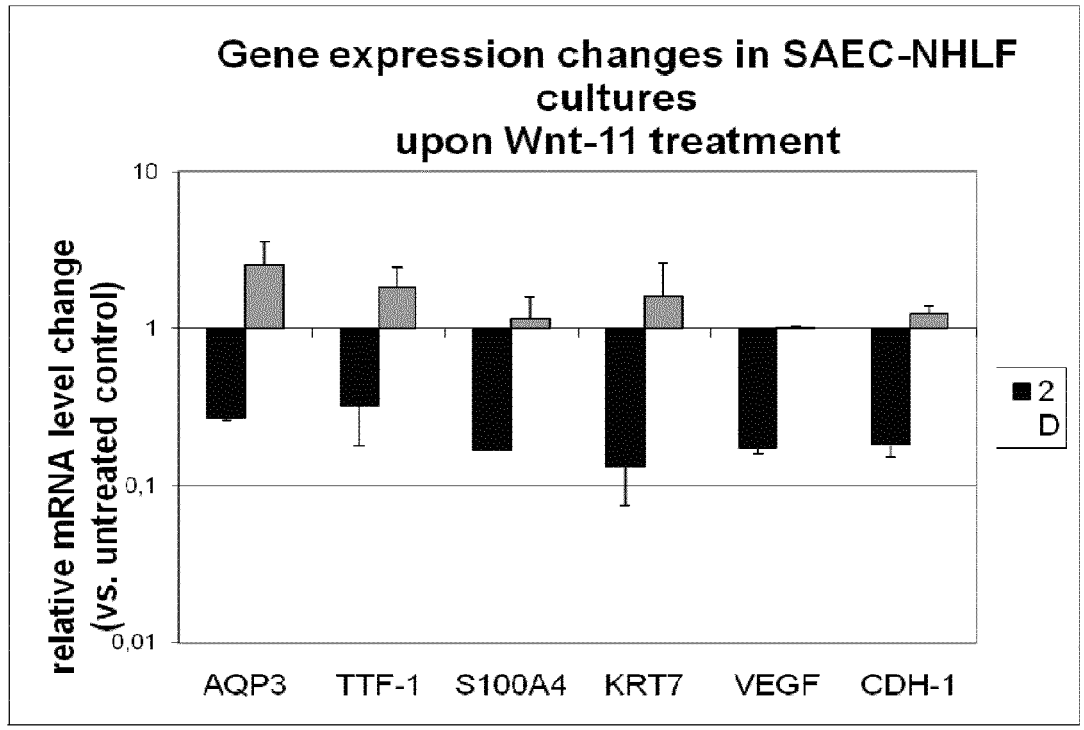

FIG. 9: Gene expression changes in SAEC-NHLF cultures upon Wnt-11 treatment. Change of mRNA levels were determined both in 2D and 3D cultures as compared to untreated control cultures.

Figure 10:
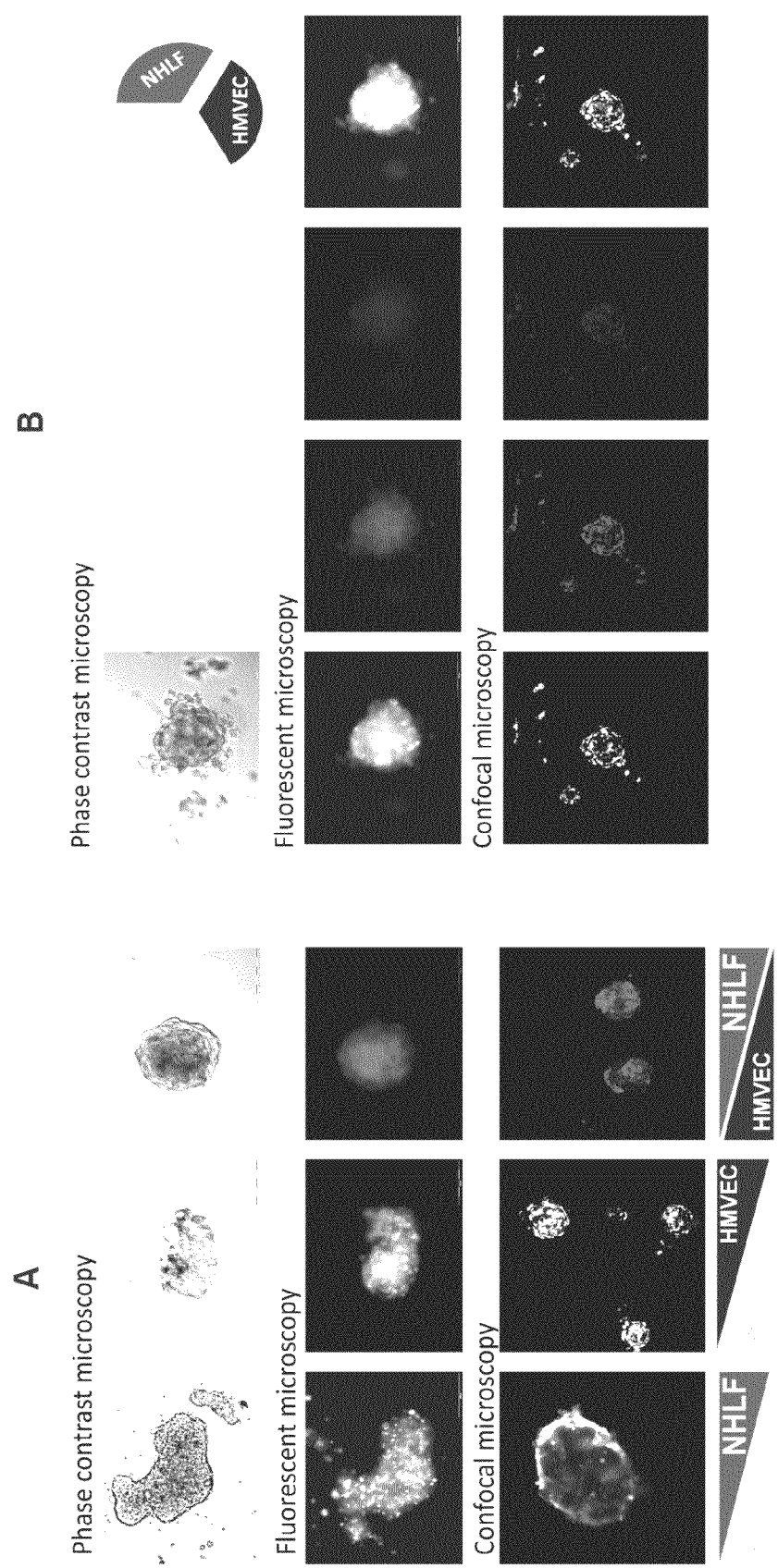

FIG. 10. Structure of 3D three-cell type microcultures consisting of SAEC, NHLF, and HMVECs. SAEC, NHLF and HMVECs were stained with the vital dyes CFSE, DiI, or DiD, respectively, then aggregated. After 24 hour incubation, the spontaneously rearranged two- or three-cell type microcultures were carefully transferred into 24 well cell culture plates for imaging. Panel A: two-cell type cultures; Panel B: three-cell type cultures. Top row: phase contrast microscopic images; Middle row: fluorescent microscopic images; Bottom row: confocal images. SAEC: green channel; NHLF: red channel; HMVEC: blue channel.

Figure 11:
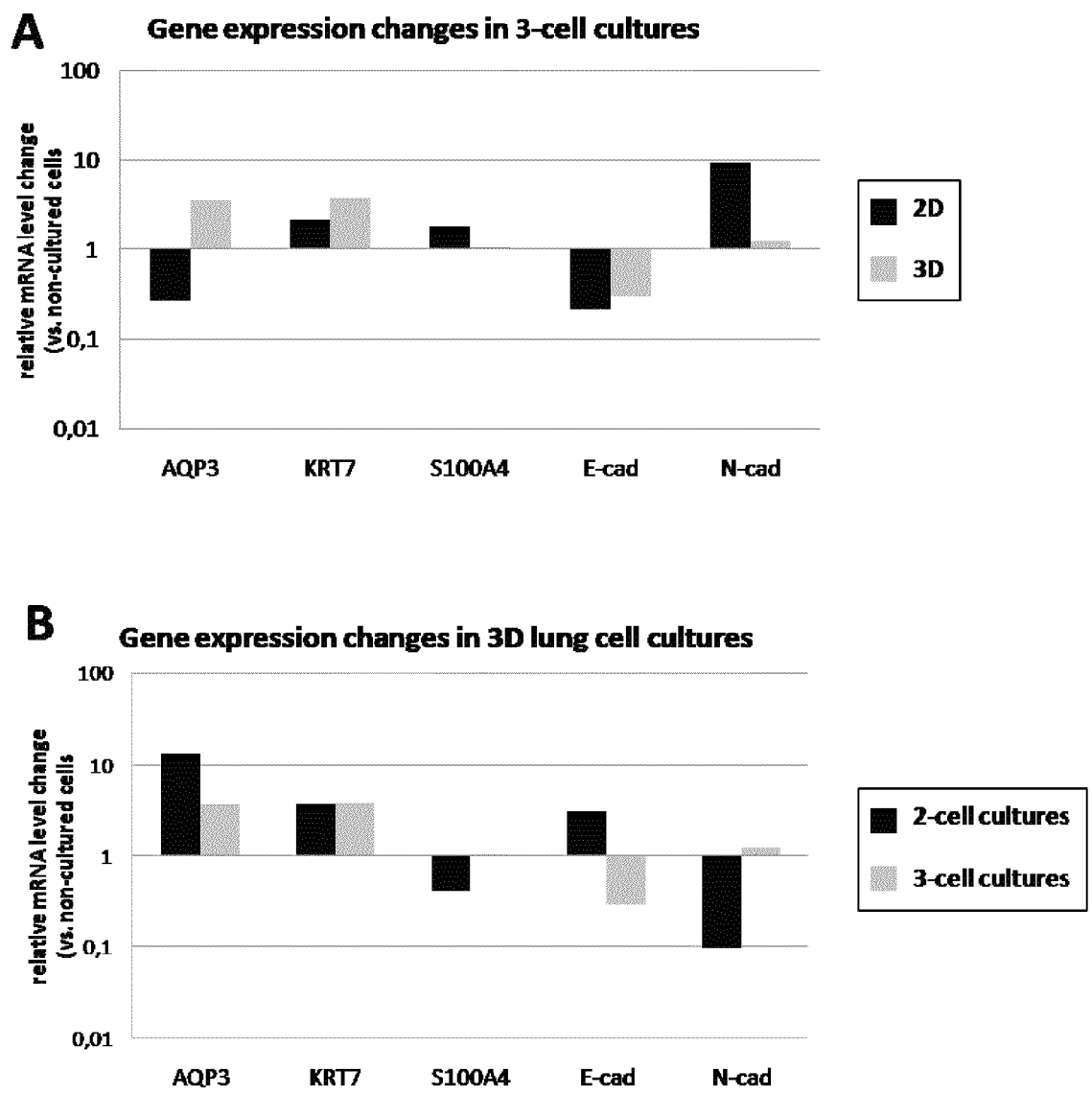

FIG. 11. Gene expression changes in three-cell type cultures. Panel A: The expression levels of AQP3 and KRT7 increased, S100A4 and N-cad decreased in 3D cultures compared to 2D cultures. Panel B: Comparison of expression changes of molecular markers in 3D SAEC-NHLF two-cell type cultures and SAEC-NHLF-HMVEC three-cell type cultures. AQP3 and E-cad mRNA levels are increased, S100A4 and N-cad are decreased in indicating that differentiation of the tissue was maintained in the three-cell type model. Purified primary lung cells used in all our experiments originated from random donors.

Figure 12:
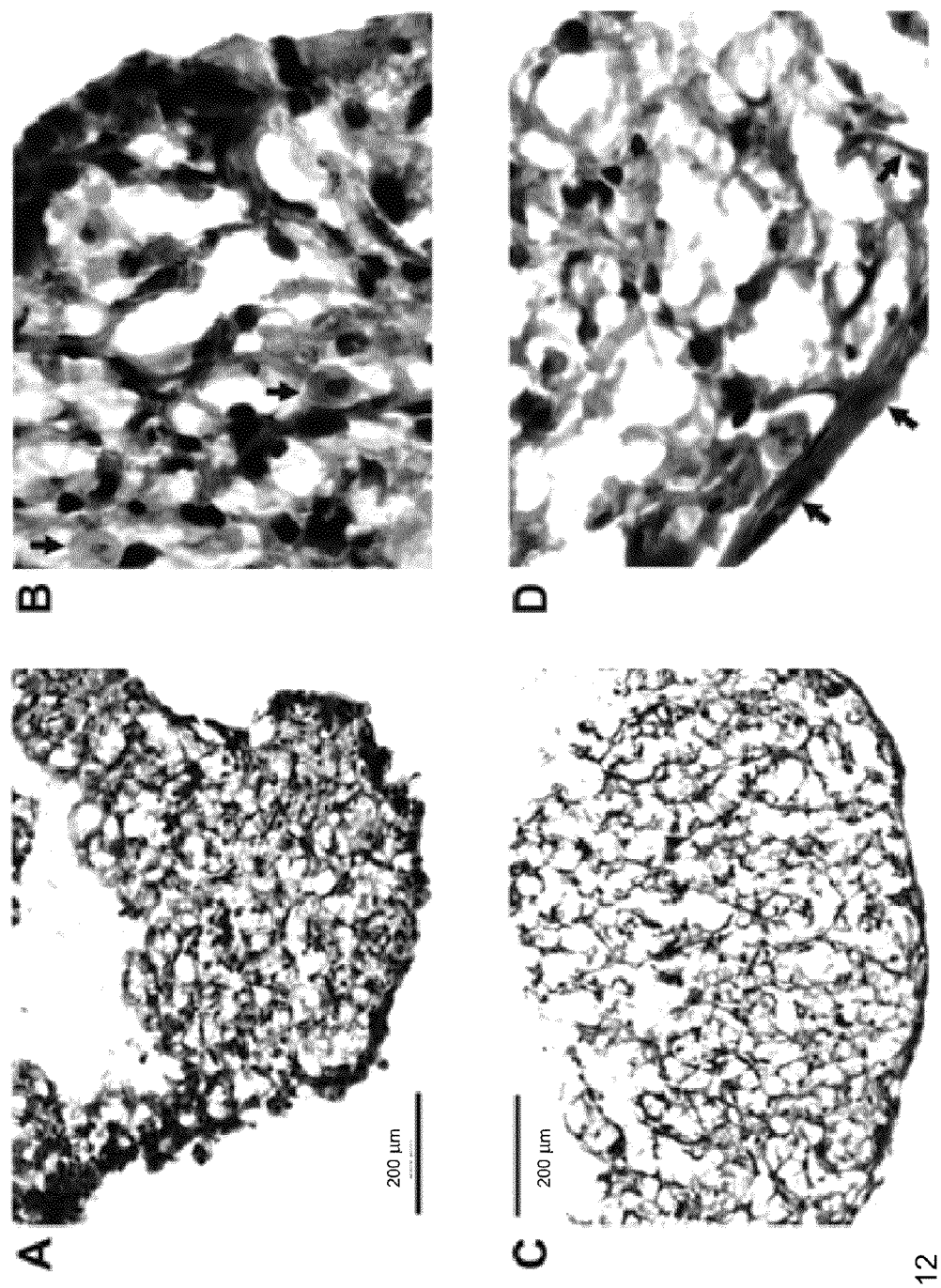
Figure 12:
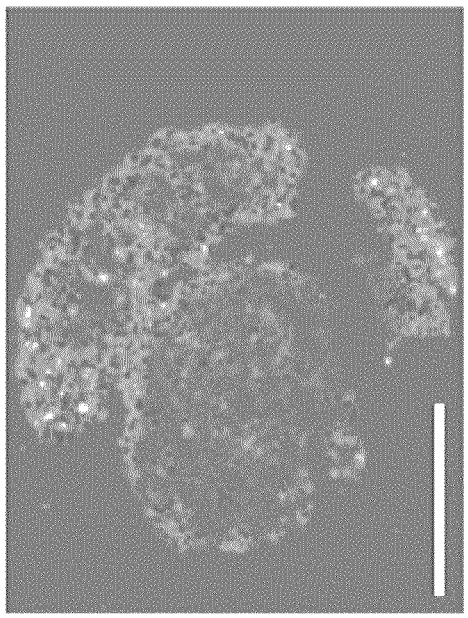
Figure 12:
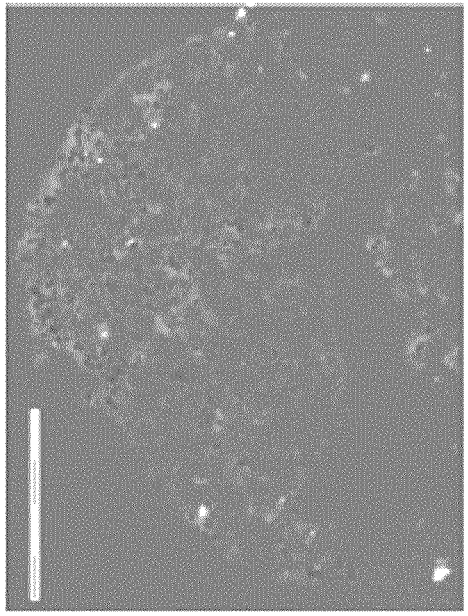
Figure 12:
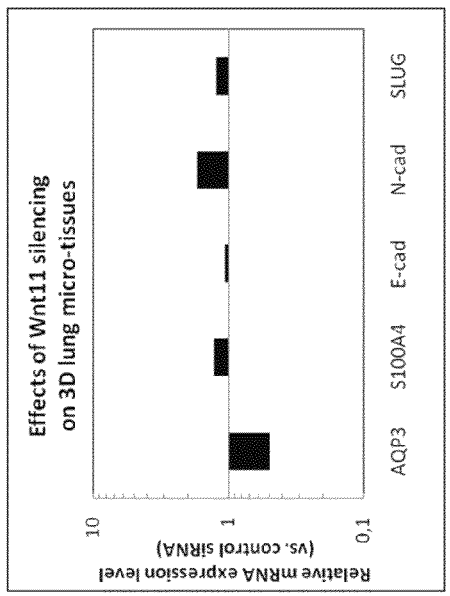
Figure 12:
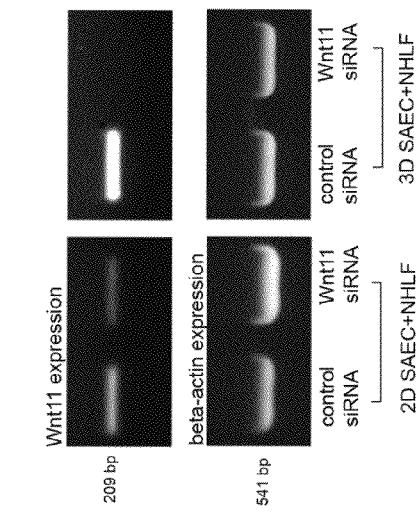

FIG. 12 Effects of Wnt11 silencing on lung micro-tissues. 3D micro-tissue cultures were set up for 72 hours using NHLF cells transfected with negative control or Wnt11-specific siRNA. Panels A and B: Haematoxilin-eosin (HE)-stained sections of samples transfected with negative control siRNA. Panel A: 10× HE stained image, bar represents 200_m; Panel B: 40× HE stained image. Note the morphologically characteristic cells resembling ATII cells (arrows) and the cuboid-like epithelial cells which are more abundant when Wnt11 is present. Panels C and D: HE-stained sections of samples transfected for 72 hours with Wnt11-specific siRNA. Panel C: 10× image, bar represents 200_m. Panel D: 40× HE stained image. Note the flat epithelium (arrows) and the porous structure. Panels E and F: Immunofluorescent staining for EMT marker N-cadherin (N-cad) in control siRNA and Wnt11 -specific siRNA transfected samples, respectively. N-cad fluorescence is shown in the red channel, nuclei are counterstained with DAPI, appearing in the blue channel. Note the increase of N-cad expression in the abscence of Wnt11 (Panel F) compared to that of in the control siRNA transfected micro-tissue (Panel E). Panel G: Efficacy of Wnt11 silencing in 2D and 3D SAEC-NHLF co-cultures. While Wnt11 level show a manifest decrease 72 hours after transfection in 2D cultures, its level remains undetectably low in 3D cultures. Panel H: Relative mRNA level changes were measured in 3D lung cell co-cultures transfected with control or Wnt11 siRNA. Diagram bars represent fold changes of mRNA expression levels in Wnt11 siRNA samples compared to that of in control siRNA samples. AQP3: Aquaporin 3; S100A4: calcium-binding protein S100A4; E-cad: E-cadherin; N-cad: N-cadherin, SLUG: SNAI2 transcription factor. Note the increased AQP3, and E-cad levels and the decreased S100A4, N-cad and SLUG levels in the presence of excessive Wnt11. One representative diagram is shown of three independent experiments.

Figure 13:
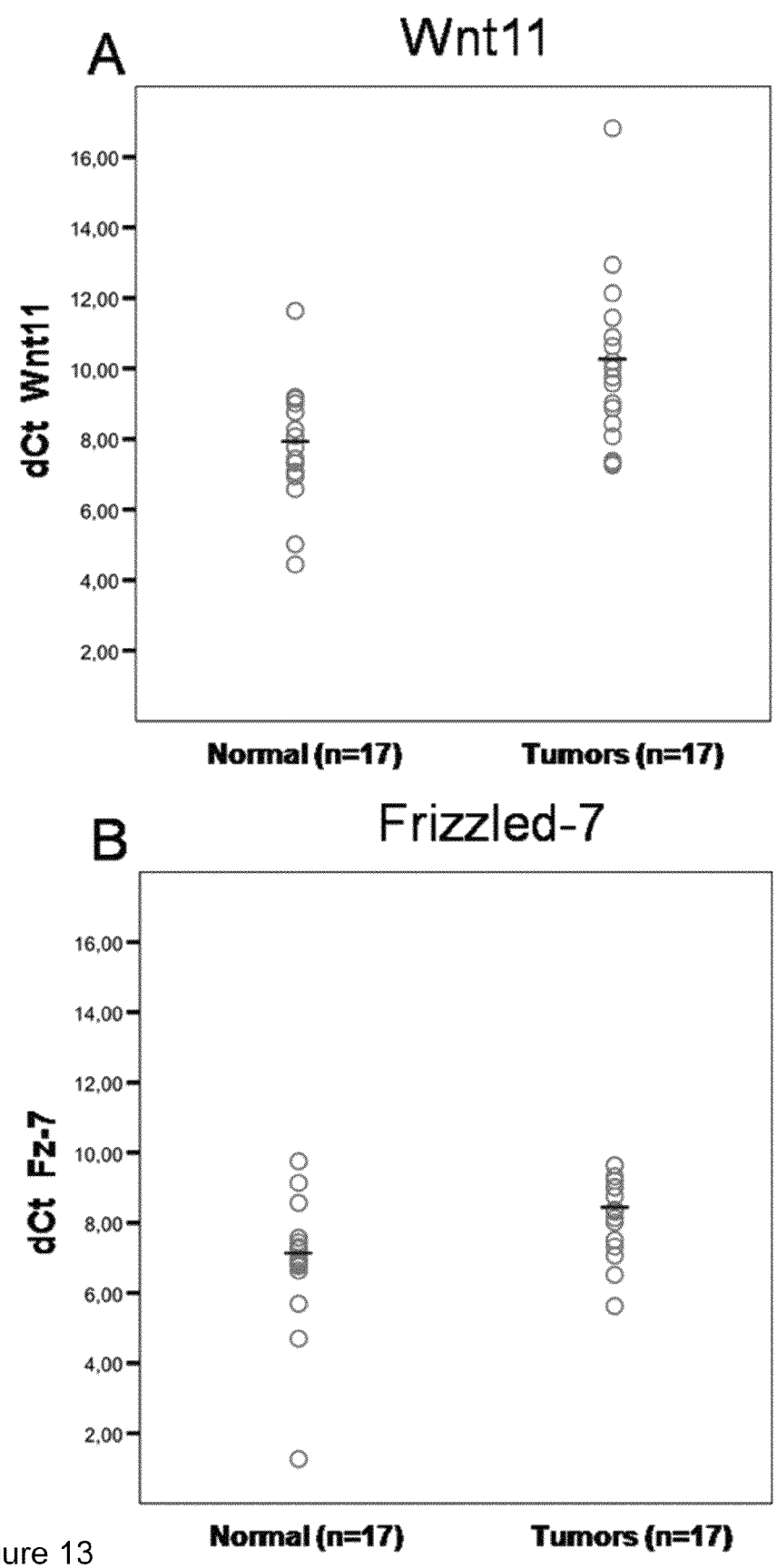

FIG. 13. Real-time quantitative PCR results from surgically obtained patient samples. Panels A and B: Levels of Wnt11 and Frizzled (Fz)-7 mRNA expression in NSCLC resection samples, respectively. Quantitative RT-PCR measurements of mRNA level in seventeen lung cancer (LC) samples (detailed clinical and pathological data of the patients are shown in Table 1.) Red circles represent dCt values calculated using the formula Cttarget gene−Ctb-actin, horizontal black lines show dCt means. Statistical comparisons were made using paired t test.

Panel A: Relative Wnt11 mRNA expression. Wnt11 was significantly under-expressed in NSCLC group compared to autologous normal lung tissue samples (p=0.007). Panel B: Relative level of Fz-7 mRNA expression. Fz-7 was significantly downregulated in NSCLC samples (p=0.001) compared to normal lung tissue.

Figure 14:
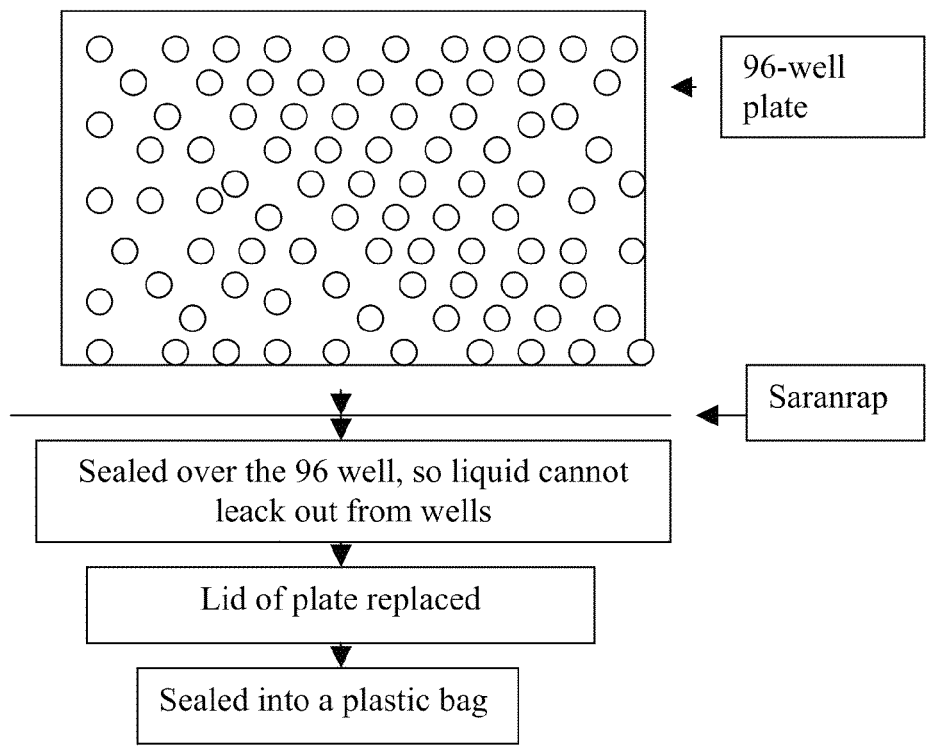

FIG. 14. Flow chart of the preparation of a test-ready lung tissue kit.

Figure 15:
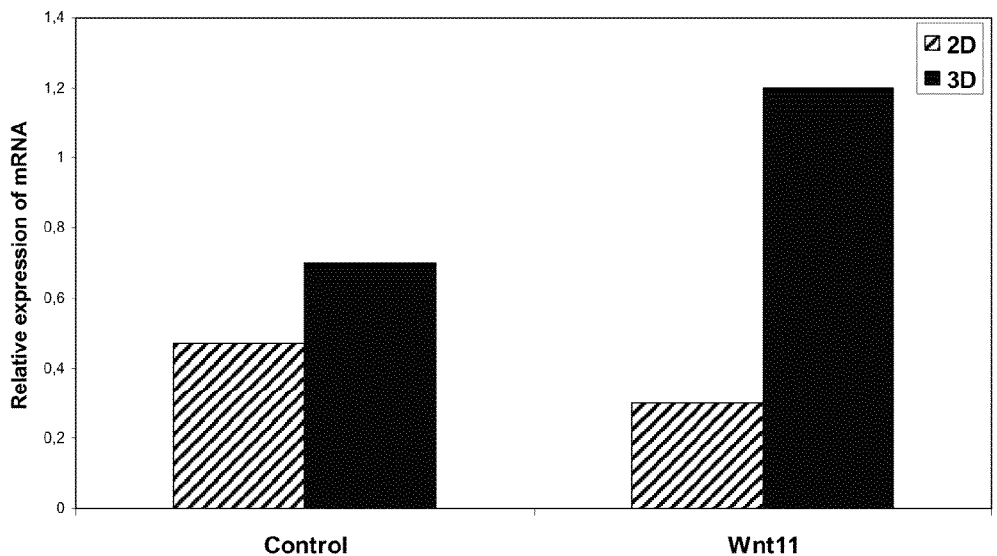

FIG. 15. Gene expression changes in SAEC-NHLF cultures upon Wnt-11 treatment. Change of mRNA levels of SFTPA were determined by PCR both in 2D and 3D cultures as compared to untreated control cultures.

DETAILED DESCRIPTION OF THE INVENTION

The present inventors created a simple engineered three dimensional pulmonary model tissue culture, useful as a lung tissue model and ready for use in various test methods.

The engineered three dimensional (3D) pulmonary model tissue culture of the invention is free of an artificial tissue scaffold, comprises cultured cells which are at least pulmonary epithelial cells and mesenchymal cells, preferably fibroblasts, and has morphological features typical of the pulmonary tissue, in particular, it is in the form of one or more cellular aggregate(s), wherein the aggregates comprise cavities or luminal structures.

In the model tissue culture of the invention typically the surface of the aggregate(s) is enriched in the pulmonary epithelial cells. Thus, the ratio of the epithelial cells as compared to the mesenchymal cell is higher on the surface of the aggregates than in other parts, e.g. in the inner or interior part of the aggregates.

The epithelial cells in the 3D culture express epithelial differentiation markers, typically, express such markers at a higher level than control non-cultured cells or control two dimensional (2D) cultures. In an embodiment the artificial tissue scaffold is a porous 3D matrix; a 3D gel matrix or a porous membrane support.

In a highly preferred embodiment of the invention the model tissue culture having an improved morphology and pulmonary marker expression profile is obtainable by treatment with Wnt11 protein as a further step. In an embodiment the model tissue culture is treated with supernatants of cells expressing or overexpressing the Wnt11 protein. In a further embodiment one or more types of cells of the tissue express or overexpress or recombinantly express the Wnt11 protein.

The engineered 3D pulmonary model tissue culture of the invention is prepared by a method comprising the steps of
  preparing a mixed suspension of at least pulmonary epithelial cells and mesenchymal cells
  pelleting the cells of the suspension,
  incubating the pelleted suspension in the presence of $CO_2$, for a time sufficient to the cells to form a 3D pulmonary model tissue comprising one or more cellular aggregate (s).

The cells are preferably fibroblast cells.

In an embodiment the model tissue is assayed for
a) expression of one or more epithelial differentiation markers characteristic to model tissue culture, and an increased expression level as compared to a reference culture is considered as indicative of the formation of a 3D pulmonary model tissue culture; and/or b) expression of one or more pro-inflammatory cytokine as defined above, and a decreased expression level as compared to a suitable reference culture is considered as indicative of the formation of a 3D pulmonary model tissue culture c) size and morphology of the one or more aggregate(s).

The reference culture may be a composition of non-cultured epithelial and mesenchymal cells or may be an analogous 2D culture.

In a preferred embodiment the culture is further treated with a Wnt11 protein and cultured in the presence of the Wnt11 protein so that an improved morphology and marker expression profile is obtained. In an embodiment the model tissue culture is treated with supernatants of cells expressing or overexpressing the Wnt11 protein. In a further embodiment it is provided that one or more types of cells of the tissue express or overexpress or recombinantly express the Wnt11 protein.

Both scaffold based and scaffold free systems were tested as described herein. The inventors have analyzed the present 3D scaffold free pulmonary model tissue culture and surprisingly found that it shows significant similarities with native lung tissue both in terms of lung tissue specific marker expression and morphology.

Without being bound by theory it appears that the present model avoids the problem of fibroblast overgrowth due to the formation of structured aggregates. In the prior art, fibroblast cells which are not in aggregates might have attached to the surface of the vessel, start propagation till contact inhibition is achieved by them.

It is to be understood that in certain systems the scaffold e.g. a matrix is biodegradable. However, these systems are not to be considered as scaffold free systems even after the scaffold is degraded because the scaffold affects or defines the structure or shape of the tissue culture. Besides, in in vitro systems like in the present invention generally it can not be expected that a degradable membrane will be dissolved.

Moreover, dissolution of a biodegradable scaffold takes a long time, much longer than the time for preparation and usage of the tissue culture of the present invention.

Cell which are not de-differentiated cells can also be applied in the present invention, however, the number of cells in an aggregate will be small. Therefore, this embodiment is useful mainly in cases when a small number of cells is sufficient to a projected test, e.g. when the test is sensitive enough. In a rapid test it is possible to start the preparation of the model tissue culture of the invention from purified, differentiated cells. Such cells can be freshly prepared from a subject. This version of the method is particularly useful e.g. in patient-specific testing of drugs or compounds or if the effect of an active agent is to be tested in a specific disease setting (for example for a potential manufacturer).

Primary cells can be obtained from commercial sources, too. For example Lonza Verviers, S.p.r.l. Parc Industriel de Petit-Rechain B-4800 Verviers, Belgium; Biocenter Ltd., Temesvari krt. 62 H-6726 Szeged, Invitrogen Corporation (part of Life Technologies Corporation 5791 Van Allen Way, Carlsbad, Calif. 92008 USA)

If large number of samples are needed, cells are to be propagated before preparing the model tissue culture samples. During this process de-differentiation may occur. This is the case in screening (e.g. HTS) applications. In patient-specific testing a smaller number of samples is sufficient.

When the cells are differentiated in an aggregate, propagation is slowed down or stopped and thereafter the aggregates do not increase significantly If a small number of samples are sufficient no preliminary propagation is needed. Typically, this may occur in patient sample testing for a few drugs or if certain phenomena, e.g. signaling processes are to be observed. However, in screening processes a large number of samples are needed and propagation of cells before the preparation of the model tissue culture should be performed.

In preferred embodiment of the invention adult, dedifferentiated epithelial cells are used. It was not known in the art that in adult, dedifferentiated epithelial cells, simply co-cultured in the presence of fibroblasts are capable of effecting differentiation that would further increase in 3D conditions, in particular in conditions appropriate for formation of 3D aggregates. Thus, in a preferred embodiment the model tissue culture preparation is started from de-differentiated cells.

Primary cells, kept in a culture, e.g. in a 2D tissue culture will exhibit certain dedifferentiation markers. Thus, such cell can be applied in the present invention, as well. Dedifferentiation markers include S100A4, N-cadherin and inflammatory markers. Thereby a larger number of cells can be applied.

Pluripotent or undifferentiated cells can be rendered capable of differentiation after addition of tissue component and/or factors.

Cellular Interactions Within Pulmonary Tissue

Cellular De-differentiation and Re-differentiation

Both stem cells and tissue specific progenitor cells can undergo directed steps of tissue specific differentiation and therefore represent an ideal source for generating organ specific tissue culture material. Unfortunately, both cell types are only available in limited numbers in differentiated tissues.

As tissue models need to be set up on a regular basis according to experimental and/or testing requirements, tissue specific differentiated cells represent a better source of primary material, simply as there are more of them. The present model system utilizes, at least in part, the phenomenon that differentiated cells in 2D culture conditions can de-differentiate and can be forced to re-differentiate using the right culture conditions in 3D conditions.

Cellular Interactions

Lung development, as well as epithelial injury repair, is tightly coordinated by a fine balance between stimulatory versus inhibitory genes that appear to co-regulate the function of stem and adult progenitor cells in the lung. For example, FGF receptor tyrosine kinase signaling is essential for respiratory organogenesis and is negatively regulated by a family of inducible FGF pathway inhibitors (Zhang, Stappenbeck et al. 2005). Additionally, FGF signaling is required for formation of new alveoli, protection of alveolar epithelial cells from injury, as well as migration and proliferation of putative alveolar stem/progenitor cells during lung repair. Conversely, TGF beta receptor serine-threonine kinase signaling via Smads 2, 3 and 4 inhibits lung morphogenesis and can inhibit postnatal alveolar development, while excessive TGF beta signaling via Smad3 causes interstitial fibrosis.

As we currently understand, maintenance of the overall structure and function of the lung,distal airways depends on type II cells (ATII). ATIIs, which are responsible for the synthesis and secretion of pulmonary surfactants as well as generation of alveolar type I (ATI) cells. Finely tuned proportion of these cells in the lung epithelium during both development and post injury regeneration following therefore is a decisive issue. Still, while engraftment by circulating pluripotent cells seems to occur more frequently in the lung injury is particularly important parenchyma than in other tissues (Krause D S, 2001), factors that determine and regulate type II differentiation remain largely unknown.

The use of primary human tissues was particularly important as shortcomings of non-human models have often compromised the success of understanding molecular interactions within human tissue types and organs. Application of a 3D structure is advisable as primary human cells that are frequently used in molecular studies and cultured in traditional two dimensional (2D) cell culture conditions loose their characteristic differentiation markers.

Thus, there is a requirement for reciprocal, albeit rather complex system of interactions between the mesenchyme and the epithelium. The present inventors hypothesized that a basic lung model can be created by using a mix of purified alveolar epithelium and fibroblasts.

Therefore, initially only two cell types were used by the inventors: primary human fibroblasts (NHLF) and small airways epithelial cells (SAEC with ATII characteristics) that are both commercially available (Lonza). It has been surprisingly found that these two cell types sufficiently provides the necessary factors to form a 3D pulmonary tissue model. The skilled person will understand that by addition of further cell types, for example of cell types listed herein, the model can be further developed.

The 3D lung model was set up without externally pre-constructed scaffold material or extracellular matrix (ECM), matrigel or other ECM-derived hydrogels to allow fibroblasts and epithelial cells to secrete ECM and create their own scaffold.

Marker Expression in 3D Cultures

Molecular characterization of the model was based on epithelial differentiation markers using real-time PCR analysis. mRNA was purified from the cell aggregates and cDNA was generated. The marker expression profile indicated an inducible increase in ATII type differentiation that was further supported by no increase in ATI type marker expressions. Once epithelial cells were co-cultured with fibroblast cells, S100A4 and N-cadherin levels decreased significantly, while the E-cadherin levels increased. The "cadherin-switch" [Zeisberg M and E. G. Neilson (2009)] was more prominent in 3D than in 2D culture conditions indicating that apart from the presence of fibroblast cells, the 3D structure was also necessary to decrease dedifferentiation of SAEC.

As triggered by pulmonary infection or alveolar epithelial injury (disruption of continuous epithelial cell layer) pro-inflammatory cytokines are produced by the alveolar epithelium to attract inflammatory cells, including neutrophils.

Decreased expression of pro-inflammatory and inflammatory markers is SAEC cultured in 3D conditions was significant.

Immunofluorescent staining of fibroblast (VIM) and AEC (KRT7, SFTPA and SFTPC) markers disclosed overlaps of different marker expressions indicating that segregation of the two cell types is far from complete. The re-created distal airway-like structure using merely adult SAEC and NHLF cells proved that not only embryonic cells but purified and differentiated adult primary cells retain their ability to form tissue structures resembling their tissue of origin in vitro.

Using qRT-PCR both in Wnt11 treated and non-treated model tissue cultures, lung epithelial differentiation markers including Thyroid transcription factor (TTF-1), Aquaporins (AQP) and Surfactant proteins (SFTP) were analyzed in alveolar epithelial cells (AECs) purified from the 3D model and were compared with AECs cultured in traditional two-dimensional (2D) SAEC, 3D SAEC and 2D SAEC-NHLF co-cultures. Progressive de-differentiation from type II characteristics of purified SAEC was detected in 2D and even in 3D but not in 3D co-cultures. As type II marker Surfactant Protein A (SFTPA) (FIG. 1H) was already regained in SAEC purified from 2D SAEC-NHLF co-cultures, the presence of NHLF was confirmed as an important component of type II differentiation.

A marked increase in type II differentiation markers was detected, when epithelial cells were incubated in the presence of mesenchymal cells (fibroblasts) in a 3D system. Moreover, a down-regulation of de-differentiation markers showed a suppression of EMT was in the 3D model. Upon examination, fibroblasts turned out to be the primary source of Wnt11 in the 3D model (FIG. 4.C) indicating involvement of Wnt11 in AEC differentiation in adult, similarly to embryonic pulmonary tissue.

In conclusion, Wnt11 in all studied culture conditions was able to increase ATII type differentiation of the alveolar epithelium, marked by a drastic boost of surfactant expression. Wnt11, however, was only able to up-regulate surfactants in the presence of fibroblasts upon direct interaction with epithelial cells indicating the importance of reciprocal interactions in the maintenance of primary adult pulmonary tissues.

Surprisingly, it was found that the effect of Wnt11 was the opposite on 3D and 2D tissue cultures (see FIG. 9 and FIG. 15).

In a preferred embodiment one or more the following marker levels, preferably mRNA levels are changed:
  AQP3 level is increased at least 1.5, 2, 2.5 or 3 fold,
  TTF-1 level is increased at least 1.5, 2 or 2.5 fold,
  KRT7 level is increased at least 1.2, 1.5 or 2 fold,
  pro-SFTPC level is increased at least 1.2, 1.5, 2, 2.5 or 3 fold
  SFTPA level is increased at least 1.2, 1.5, 2, 2.5 or 3 fold
  in comparison with a control 3D tissue culture not exposed to Wnt11.
  AQP3 level is increased at least 2.5, 3, 4, 5, 6, 7 or 8 fold,
  TTF-1 level is increased at least 2, 2.5, 3, 4, 5 or 6, fold,
  KRT7 level is increased at least 2.5, 3, 4, 5, 6, 7 or 8 fold,
  pro-SFTPC level is increased at least 1.2, 1.5, 2, 2.5, 3, 4, 5, 6, 7 or 8 fold
  SFTPA level is increased at least 1.2, 1.5, 2, 2.5, 3, 4, 5, 6, 7 or 8 fold
  in comparison with a control 2D tissue culture exposed to Wnt11.

Thus Wnt11 caused a more differentiated tissue with an increased ATII characteristic and reduced EMT features, This fact indicates that Wnt11 is suitable for tissue injury repair and useful in the treatment of diseases causing lung tissue injury and scars.

Segregation of Cell Types in Mixed Culture (Sorting)

Our microscopic examinations demonstrate that spontaneous tissue reorganization—"sorting"—occurs in 3D lung primary cell cultures. The present inventors used herein a simple centrifugation method to aggregate cells similarly to that of the preparation of fetal thymic organ cultures [Hare, K. J. et al. (1999)]. Evidence is provided herein that 3D co-culturing of primary pulmonary epithelial cells with fibroblasts is more advantageous for SAEC to maintain a more differentiated status than in either 2D or 3D in vitro monocultures. Inclusion of NHLFs not only facilitated epithelial differentiation but the cohesion and structure of the 3D micro-tissues were much more firm and compact compared to SAEC-only (FIG. 2) or SAEC-HMVEC (FIG. 10.a) cultures.

Figure 2:
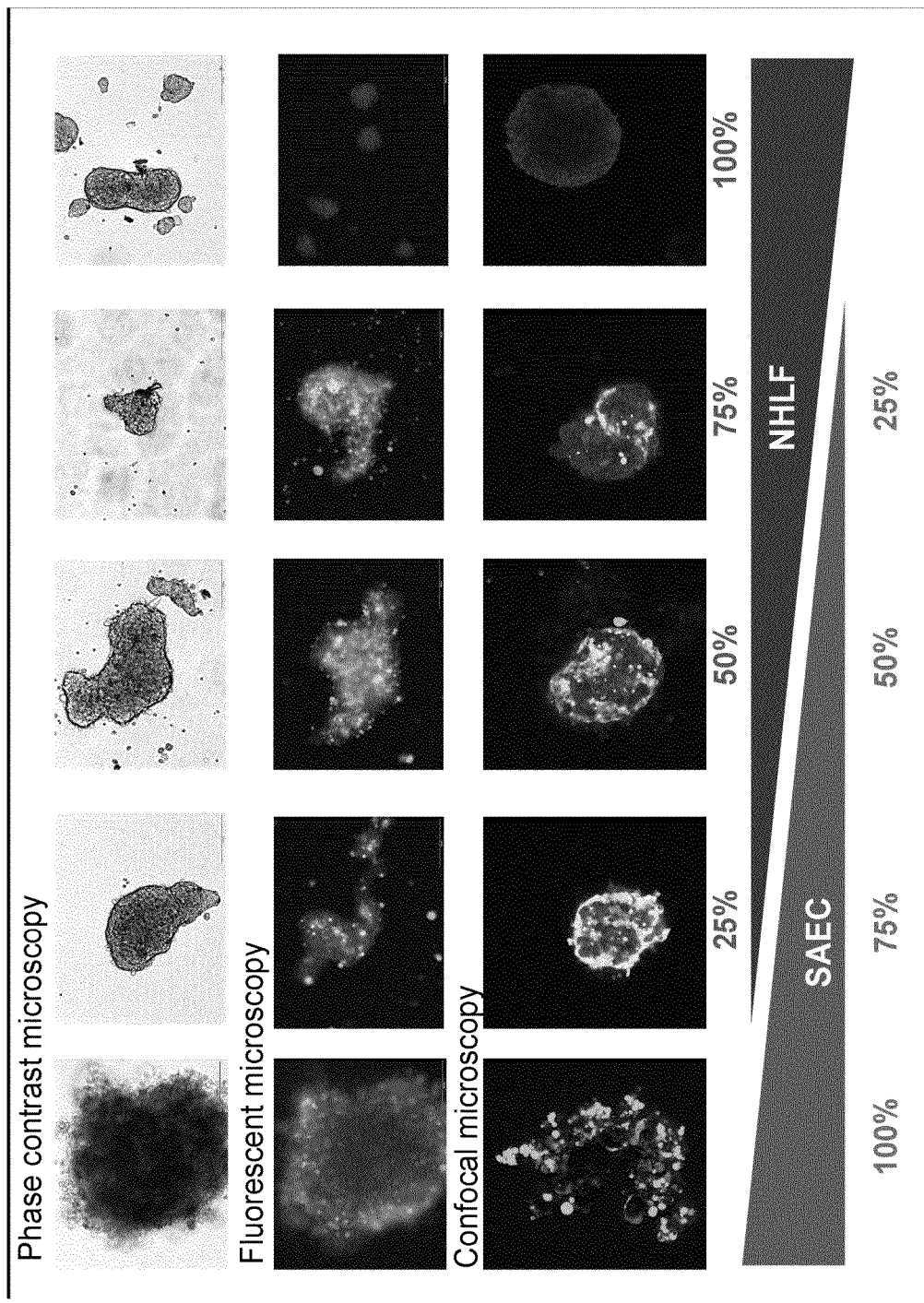
FIG. 2. Pelleted micro-tissue cultures containing different ratios of SAEC and NHLF. SAEC and NHLF cells were stained with the vital dyes of CFSE or DiI, respectively. Due to physiological fluorescent markers SAEC cells are green or light grey on black and white copies whereas NHLF cells are red or dark gray. Cell populations either pure or mixed at various ratios were pelleted and aggregates were formed after 24 hour incubation, then transferred into 24 well cell culture plates for imaging. Top row: phase contrast microscopic images; Middle row: fluorescent microscopic images; Bottom row: confocal images. SAEC: green channel; NHLF: red channel.

The present two-cell type co-culture system, consisting of human small airway epithelial cells (SAEC) and normal human lung fibroblasts (NHLF) did not require the presence of externally added extracellular matrix (ECM) for the formation and maintenance of 3D structure (FIG. 2). Pelleting SAEC and NHLF cell suspensions of single cell type and cell mixtures of various ratios revealed that creation of pulmonary micro-tissues require the presence of fibroblasts to maintain a compact and stable 3D structure (FIG. 2). Morphologic examinations of 3D micro-tissues revealed that segregation of the two cell types in mixed cultures was a feature of 3D micro-tissues, fibroblasts forming the inner, core part, while epithelial cells were covering the outer layer (FIG. 2). The phenomenon of segregation or "sorting" is based on different adhesive energy characteristics of cell types and has not been described for primary human pulmonary tissue before. The spontaneous cell "sorting" is based upon the disparity of the cohesive forces between different cell types: the most cohesive core or central region of the pulmonary micro-tissue is formed by the NHLF population being surrounded by the less cohesive SAEC. The process of segregation in primary, differentiated human pulmonary tissues is particularly interesting, as underlies the notion that even differentiated, human adult cells maintain their ability to actively explore their own microenvironment. The cells in the 3D co-cultures are capable of exchanging position with adjacent cells thus structurally reorganizing the tissue. This process also requires reorganization of the extracellular matrix. Studies of the models of various SAEC/NHLF ratios in the 3D micro-tissue models revealed that 1:1 ratio is sufficient for the epithelial cells to cover the inner core of fibroblasts therefore further analysis of the model was performed using the 1:1 setting. The model can be useful, however, at other epithelial-mesenchymal cell ratios. The ratio sufficient for full coverage may vary to some extent depending on cell type.

Without being bound by theory, the present inventors think that segregation of cells in the present model is due to different cohesivity of the cell types in which a difference in their surface tension plays a major role.

Cells explore actively their own microenvironment, are able to exchange position with adjacent cells or to reorganize the extracellular matrix in their vicinity. The latter process is known to involve both mechanical traction forces and enzymatic activity by matrix metalloproteases (MMPs). Based on different adhesive energy characteristics, it is a known experimental fact that certain cell compositions of mixed cell types can segregate in an aggregate.

In segregated cell aggregates of hanging drop cultures the most cohesive population occupies the central region, being surrounded by the less cohesive one. A measure of tissue cohesivity is the surface tension of the cells. Thus, surface tension, which is an experimentally detectable quantity, can predict the sorting hierarchy. Therefore there early attempts have been made in the art to by this sorting hierarchy can be predicted to a certain extent if a new cell type is to be involved (Neagu 2006).

However, surface tension factors are not known for specific cell types of the human lung. The prior art was fully silent as to whether the phenomenon of tissue sorting would happen in other cultures or only in hanging drop cultures. The present inventors experimentally determined show herein for the first time that, surprisingly, segregation of epithelial and fibroblast cells happens in pelleted mixed alveolar epithelium and fibroblast cultures.

Structure of the Microaggregates

Figure 3:
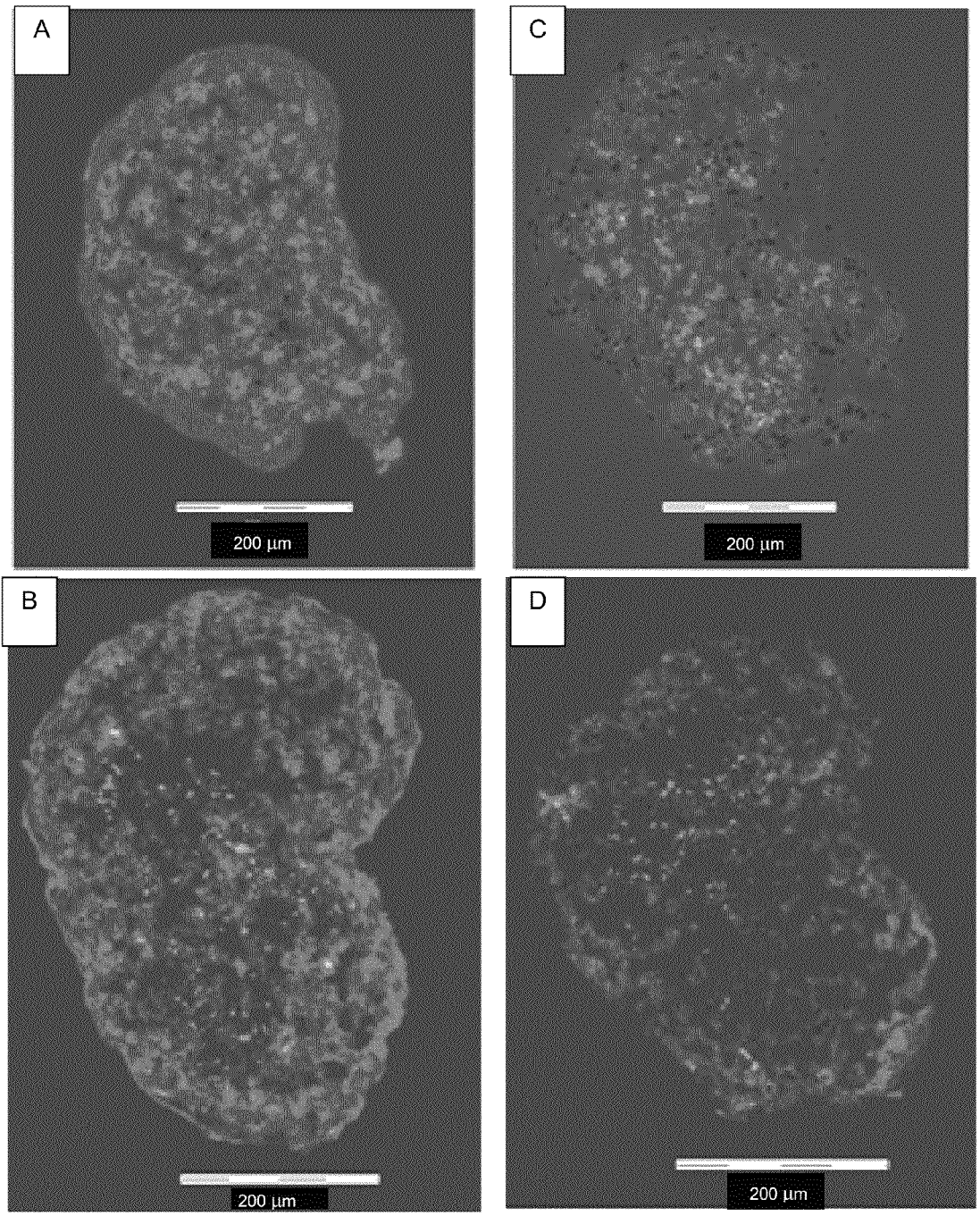
FIG. 3 Immunofluorescent images of cryostate sections of 3D micro-tissues. SAEC-NHLF micro-tissues were cultured for 72 hours in V-bottom plates, bar represents 200 µm, nuclei were stained with DAPI, shown in the blue channel. Panel A: Lung epithelial marker Cytokeratin-7 labeling of a lung micro-tissue section. Note the porous structure and the largely even distribution of Cytokeratin-7. Panel B: Vimentin labeling of a lung microtissue section. Note that the expression of the mesenchymal marker Vimentin is mainly confined to the central region, coinciding with fibroblast localisation as suggested also by confocal microscopy (FIG. 2, bottom row). Panels C and D: Surfactant Protein-A and Pro-surfactant Protein-C labeling of lung microtissue sections, respectively. Note the peripheral expression of the Surfactant proteins, and also the more intensive staining of Surfactant Protein-A (Panel C).

It was unexpectedly found by the present inventors that according to the invention 3D pulmonary model tissue aggregates could be formed which show certain features of lung tissue as to morphology and marker expression. Further histological analysis revealed a complex structure of the model. Although the 3D lung model was set up without externally added scaffold material or extracellular matrix (ECM), matrigel or other ECM-derived hydrogels to allow fibroblasts and epithelial cells to secrete ECM and create their own scaffold, hematoxylin eosin (HE) staining revealed an organized network of cells, strongly resembling the structural complexity of the distal airways (FIGS. 3 and 8). It is found that not only embryonic cells but purified and differentiated adult primary cells retain their ability in culture to form tissue structures similar to their tissue of origin.

The alveolus-like cavities of the aggregates are composed of both fibroblasts and epithelial cells. The diameter of the cavities vary between 2-100 υm (nanometer).

Moreover, HE staining of Wnt11 SN-treated samples exposed, however, an increased number of cells with cuboid-like morphology resembling ATII cells. In contrast, micro-tissues incubated with control A549 SN harbored only flat epithelium (FIGS. 8D and 8B).

Size of the Microaggregates

It has been shown that even very small but structured aggregates exhibit tissue features and thus are appropriate for studying interactions, and testing compounds or environmental effects.

Small aggregates have several advantages, for example, no special reaction vessels are needed, their size and ratio of different cell types are reproducible and thereby interactions are more easyly controlled. In small aggregates practically no necrotization of the inner parts of the tissue aggregates can be expected. Furthermore, a surprisingly uniform size distribution can be achieved which renders them quite appropriate for parallel testing.

Thus, preferably, according to the invention the size of the aggregates should be kept small provided that tissue features appear and thereby interactions can be examined.

If the aggregates are too small, a correct morphology as disclosed herein may not take form and the aggregate may not have a tissue like characteristic. If the aggregates are too large, their size may largely deviate from the average. Moreover, necrotization may occur inside the aggregates, due to a longer culturing time and less perfusion of the aggregates.

In lack of special additives, for example receiving only cell culture media the growth of aggregates is controlled by contact inhibition of the cells.

The size depends, however, on the number of cells in an aggregate. The skilled person will understand that the size and cell number of the aggregates can vary within the limits given herein provided that the above-described requirements are met.

It has been found that addition of endothelial cell did not change significantly the size of the aggregates.

Cell Types Useful in the Present Invention

Fibroblast Cells

Fibroblasts are the most versatile of the connective tissue cell family and they are in fact the most ubiquitous cell type. Fibroblasts are important structural elements of tissue integrity. They participate in repair and regenerative processes in almost every human tissue and organ, including the lung. Their primary function is to secrete extra cellular matrix (ECM) proteins that provide a tissue scaffold for normal repair events such as epithelial cell migration.

Fibroblasts, or distinct subpopulations thereof, perform tissue-specific functions as immunoregulatory cell, secrete chemokines and cytokines, which are able to trigger immune responses by attracting inflammatory cells and immune cells. Fibroblasts from different anatomical locations show an array of common phenotypic attributes. Fibroblasts, however, show distinct phenotypes in different anatomical locations. Characteristic expression of fibroblast growth factors and receptors are also a feature of pulmonary fibroblasts [De Moerlooze, Spencer-Dene et al (2000)].

The present inventors have found that it is possible to rely on fibroblast physiology to create an artificial tissue scaffold-free tissue system to mimic some aspects of distal pulmonary tissue and an artificial matrix based model not necessarily the only way to create 3D pulmonary cultures. Without being bound by theory, the present inventors assume that the fact that fibroblasts in the lung secrete ECM significantly contributes to this result.

Pulmonary Epithelial Cells (Pneuomocytes)

Pneumocytes (pulmonary or alveolar epithelial cells or AECs) are epithelial cells that line the normal alveolar basement membrane, i.e. the peripheral gas exchange region within the distal airways of the lungs. Pneumocytes or AECs can be subdivided into type I and type II pneumocytes.

Characteristic markers for the two alveolar epithelial cell types are easily traceable and can be monitored during experiments e.g. using RT-PCR reactions or immuno-histochemistry.

Type 1 Pneumocytes

Type 1 pneumocytes [alveolar type 1 pneumocytes, type 1 alveolocytes, alveolar type 1 cells (abbr. ATI cells), also called small alveolar cells, squamous alveolar cells, membranous pneumocytes, or type 1 alveolar epithelial cells], are complex branched cells with multiple cytoplasmic plates that represent the gas exchange surface in the alveolus of the lung. These cells are metabolically active and harbour cell surface receptors for a variety of substances, including extracellular matrix (ECM) proteins, growth factors, and cytokines. About ninety-five per cent of the alveolar surface is covered with type I pneumocytes.

Type 2 Pneumocytes

Type 2 pneumocytes (alveolar type 2 pneumocytes, alveolar type 2 cells; abbr. ATII cells, T2P) are cuboidal epithelial cells also being referred to as type 2 alveolar epithelial cells (abbr. AEC, also EPII cells), type 2 granular pneumocytes, type 2 cells, type 2 alveolocytes, septal cells, or great alveolar cells, large alveolar cells, or granular pneumocytes. These cells arise from immature epithelial cell progenitors. Alveolar type 2 pneumocytes are thought to be progenitor cells of the alveolar epithelium. They are capable of self-renewal and differentiation into squamous type 1 pneumocytes. Type II cells are cuboidal cell, which comprise only 4% of the alveolar surface area, but constitute 60% of alveolar epithelial cells and 10-15% of all lung cells (Crapo et al, 1982).

Type 3 Alveolar Epithelial Cells

Type 3 alveolar epithelial cells differ from flat type 1 cells and cuboidal type 2 cells by the presence of an apical tuft of microvilli and the absence of lamellar type secretory granules. These cells are being referred to also as alveolar brush cells.

Endothelial Cells

Endothelial cells are oblong shaped cells that line the lumen of all blood vessels as a single squamous epithelial cell layer. They are derived from angioblasts and hemangioblasts.

Macrophages

Macrophages are cells derived from bone marrow-derived monocytes (bone marrow-derived macrophages) that have homed in to tissues. The differentiation of macrophages from uni- and bipotential progenitor cells in the bone marrow is controlled by a variety of cytokines. Further differentiation takes place in tissues and the resulting macrophage populations are being referred to as resident macrophages.

Mast Cells

Mast cells arise from a multipotent CD34(+) precursor in the bone marrow (Nakahata and Tom 2002; Austen and Boyce, 2001). Immature mast cells assume their typical granular morphology when they have migrated into tissues. These cells also express Fc-epsilon R1 and stop expressing CD34 and Fc-gamma R2. Most mast cells in the lung and intestinal mucosa produce only tryptase (designated MCT) or only chymase. Mast cells play a central role in immediate allergic reactions by releasing potent mediators.

Smooth Muscle Cells

Smooth muscle cells are highly specialized multifunctional contractile cells that regulate the lumen of hollow organs transiently (reversible contraction), or chronically (due to fibrosis and muscle hypertrophy). Smooth muscle cells play an important role in vasculogenesis and shape the wall of blood vessels and maintain vascular tone.

Observations with Further Cells

Addition of endothelial cells resulted in stable aggregates comprising differentiated cells. The degree of differentiation is not reduced if endothelial cells are included into the model tissue culture, as found based on the markers expressed. It appears that these aggregates maintain a layered structure, wherein the endothelial cells are located inside.

Embodiments

Preparation of a 3D Model Tissue Culture

In the method of the present invention at least pulmonary epithelial cells and mesenchymal cells, preferably fibroblasts are used. The cells are cultured separately in order to obtain viable cultures, then mixed in an appropriate ratio and cocultured in the presence of $CO_2$ under appropriate conditions as will be understood based on the present disclosure and art methods. By setting ratio of the cells and selecting conditions overgrowth of one cell type by another can be avoided.

In a preferred embodiment said cells are obtained from human subject as primary cells and either de-differentiated or used immediately. De-differentiation can be carried out e.g. by known methods (passages, removing other type of cells, addition of growth factors). If the cells are capable of confluence, they are considered as dedifferentiated.

Pelleting the cocultured cell mixture is an important step to establish cell-cell contacts and to result in an appropriate distance between the cells. The most convenient way to pellet the cells is to apply centrifugation. To select suitable means for pelleting is well within the skills of a skilled person based on the teaching provided herein.

In the present models in principle any of the cells listed above can be used to obtain a lung model tissue close to a native lung tissue. Each cell type applied have to be capable of growth under conditions useful to obtain the 3D model tissue as disclosed herein and being capable of association with other cell types of the model. These factors should be tested in preliminary experiments. Expediently a relatively small ratio of further cells should be initially applied then the ratio of the further cell type can be increased, typically till a ratio similar to in vivo ratios is achieved.

In preferred embodiments additional cell types that can be included in the model are e.g. endothelial cells and smooth muscle cells.

Disease Models

Based on the above model and using various gene delivery methods and variable target genes, the above system is easily adaptable to study genetic changes during pulmonary diseases that can lead to identification of novel drug targets and development of novel therapies:

wherein the disease involves inflammation, the affected cells, preferably the epithelial cells, express inflammatory cytokines (above normal level) and the model is an inflammatory model, wherein the disease is a tumor, the cells are transformed, e.g. malignantly transformed or immortal cells and the model is a tumor model, wherein the disease involves fibrosis and the model is a fibrosis model, wherein the disease involves injury of the tissue and the model is a regeneration model.

Disease models can be utilized in drug testing.

Cells Obtained from Patients

In an embodiment, pulmonary cells are obtained from patients and cultured in accordance with the present invention. In this embodiment preferably no or only partial de-differentiation is allowed. Thereafter, in a rapid preparation method 3D model tissue culture is formed and drugs proposed for treating said patient are tested or a projected therapeutic regime can be tested. The advantage of this embodiment among others is that pure and parallel sample cultures with uniform composition and size can be prepared. Said samples are also free of any pathogens and may be purified as needed.

Models Prepared from Healthy Cells

In a preferred embodiment, disease models are prepared by starting from healthy cells and factors effecting disease features (symptoms) in the cells are added later.

For example, tumor models are prepared from healthy cells and factors effecting malignous transformation are added and/or genes causing malignous transformation are expressed therein. It has been observed that the level of Wnt proteins, e.g. Wnt5 has increased in a pulmonary tumor tissue. It is thus contemplated that tumor models can be prepared by addition of tumorogenic factors, like EGF (epithelial growth factor), IGF (insulin-like growth factor), insulin, Wnt factors e.g. Wnt5 or a cocktail thereof to the cell mixture or culture of the invention.

In an alternative of this method tumorous cells are added to the medium in which the model culture according to the invention is present but are separated by a semi-permeable membrane. Thereby the factors produced by the tumorous cell induce tumorous (malignus) transition of the cultured cells of the invention.

Lung Tumor Models Made of Lung Tumor Cell Lines

Lung tumor models can be prepared from lung tumor cell lines. Such cell lines are readily available at the American Type Culture Collection (ATCC; Rockville, Md.), upon searching for tumor cell lines.

Advisably, experiments are to be performed to find appropriate conditions for culturing the cells and optimize the ratio of the cell types used in a cell mixture.

Tumor Model by Suppression of Wnt11 Expression

In an embodiment an improved tumor model can be prepared according to the invention by suppression of Wnt11 expression in the pulmonary model. This can be achieved e.g. by transduction of the mesenchymal, e.g. fibroblast cell with Wnt11 specific siRNA (FIG. 12.G). Surprisingly, down-regulation of Wnt11 coincided with up-regulation of one or more EMT markers and down-regulation of alveolar differentiation markers. Moreover, in the absence of Wnt11, the morphology of epithelial cells appeared more flattened and cuboid-like cells were no longer abundant (FIG. 12A-12D).

This suppression of Wnt11 expression can be applied both in tumor cell lines and in models prepared from healthy cells, e.g. in primary cells.

Inflammation Models

For inflammation models monocytes and/or macrophages can be added to the model culture of the invention preferably during the preparation process.

In this model pretreatment with LPS or WNT5A is advisable.

Cytokine production of activated macrophages as well as production of other factors like Wnt5 affects the tissue culture and enable an inflammation model.

If an inflammation model system is to be examined, neutrophyl cells can be provided separated from the pulmonary aggregates by a membrane in an appropriate chamber. In this case neutrophyl migration and MMP production can be measured as well.

In an alternative embodiment disease model pulmonary cell lines a cultured in accordance with the invention. In this embodiment drugs can be tested for efficiency against said disease.

In the disease models use of an overexpressing gene is to be avoided, rather an inducible promoter is to be applied.

Inflammatory Models from Native 3D Pulmonary Cell Aggregates

To mimic inflammatory conditions, native 3D pulmonary cell aggregates can be treated with various materials eliciting inflammatory reactions.

Such materials are for example:
chemical substances causing acute inflammation, such as vasoactive amines, eicosanoids, etc.
proinflammatory polypeptides, such as growth factors, hydrolytic enzymes etc.
reactive oxygen species,
proinflammatory cytokines, e.g. IFN-γ and other cytokines,
bacterial cell wall extracts.

Inflammatory conditions are tested by detecting cytokine expression e.g. by biochemical assays, immunological assays, such as ELISA, by a PCR-based method, e.g. real time PCR, or by expression analysis e.g. by applying a gene chip.

Genetic Modification of Primary Cells

Both epithelial and mesenchymal cells can be genetically modified using recombinant viral delivery vectors (rAdenoviral and rLentiviral vectors) and these gene delivery methods do not harm the ability of cells to aggregate. Characteristic genes for inflammation, tumor, fibrosis and regeneration can be constitutively or inducibly overexpressed or silenced and tissue morphology, cellular responses, gene and protein expression changes can be studied in a 3D microenvironment.

For example, one or more genes known to promote tumor formation can be introduced into a pulmonary cell line, e.g. an alveolar type I or type II cell line, preferably type II cell line or into a fibroblast cell line. Such a gene can be e.g. an oncogene, e.g. a ras gene or a gene or a set of genes typical of expression pattern of a tumor, e.g. a COX-2 gene It may happen that the expression of a ras gene alone is insufficient to transform the cells, preferably immortal cells, but proliferation is likely to be increased [Wang, X Q, Li, H et al. (2009)], which may provide a disease feature for the model.

Modification of Secreted Factor Composition in Primary Cell Aggregates Using Genetically Modified and Sub-lethally Irradiated Cell Lines In this embodiment all cell types are left non-infected, gene expressions therefore are as normal as in any given 3D lung tissue model. Cellular composition of the aggregates however contains sub-lethally irradiated cells (5-10% of total cell number of the aggregate), either fibroblast (WI-38) or alveolar epithelial (A549) cell lines or both, that are genetically modified and produce secreted factors (Wnt-s, Bone Morphogenic Protein (BMP)-s, inflammatory and pro-inflammatory cytokines, growth factors, etc) that modify the cellular microenvironment within the aggregates. Sub-lethal irradiation can reduce propagation of cells and prevent overgrowth of one cell type by the other.

Products

The invention also provides for a kit comprising multiple samples of a 3D model tissue culture.

Preferably, the containers are wells of a plate, e.g. a 96 well plate or a 384 well plate.

The 3D model tissue can be a model of a healthy tissue or a disease model (disease model kit).

The plate expediently comprises an array of containers or wells wherein a multiplicity of containers contain samples of one or more types of engineered 3D pulmonary model tissue cultures in an appropriate medium.

The container can be e.g. flat bottom, an U-bottom or, preferably, a V-bottom container, on a plate allowing parallel testing of multiple samples.

Preferably, the containers are non-tissue culture treated containers so as to avoid sticking of the cells to the container wall.

In a preferred embodiment, each container comprises a single aggregate. In a preferred embodiment, the culture samples in each container comprise cells in an amount as defined in the brief description of the invention.

Preferably, the containers are sealed, either separately or together and contain a $CO_2$ enriched environment or atmosphere suitable for a lung tissue culture as defined in the brief description of the invention.

Typically, disease models require the same environment.

Preferably, the cells are stained with a biocompatible dye suitable to report on one or more of the following cellular features: cellular state for example cell phase, cellular viability, apoptosis or moribund state of the cell; cell type; cell location; malignous transformation; inflammation.

Controls

As control samples the kit contains cultures of epithelium and fibroblasts only. On a plate, preferably at least 3-3 wells of controls (epithelium and fibroblasts, respectively) are present.

Preferably, a further control which is a 2D lung tissue is used to identify or assess features specific to the 3D tissue.

An alternative control is a culture non-treated with Wnt11.

Thus, on request, a 2D control plate (preferably a flat-bottom, adhesive tissue culture plate) can be included to accompany the 3D tissue. Alternatively, the plate may also contains wells of 2D lung tissue as a control, preferably in a flat bottom wells.

Thus, in an embodiment of the invention a plate is used which contains both V-bottom wells for 3D tissue and flat or U-bottom wells for 2D tissue.

EXAMPLES

Example 1

Materials and Methods

Primary SAEC, NHLF and pulmonary HMVEC cells were purchased from Lonza. All cell types were isolated from the lungs of multiple random donors of different sexes and ages. We used SAGM, FGM or EGM-2 medium for the initial expansion of SAEC, NHLF or pulmonary HMVEC, respectively, as recommended by the manufacturer. All types of cell cultures were incubated in an atmosphere containing 5% $CO_2$, at 37° C. For 2D and 3D culturing, pure or mixed cell populations were cultured in a 50-50% mixture of SAGM (Small Airway Growth Medium, Lonza) and complete DMEM. For two and three-cell cultures containing HMVEC cells, the appropriate growth factor supplements for HMVEC cells were added to the 50-50% mixture of SAGM and DMEM. The compositions of cell culture media were prepared in accordance with instructions of the manufacturer. For 2D and 3D culturing, cells were mixed at the indicated ratios and dispensed onto flat-bottom 6 well plates or 96-well V-bottom plates (Sarstedt), respectively. V-bottom plates were immediately centrifuged after cell seeding at 600×g for 10 minutes at room temperature.

SAECs and NHLFs were stained with the following fluorescent physiological dyes: DiI [Honig, M. G. and R. I. Hume (1989)] and CFSE [Wang, X. Q., X. M. Duan, et al. (2005)] to be able to follow cellular movements in culture. Cells with or without matrigel were pipetted into V-bottom, 96-well, non-tissue culture treated plates and were incubated for one hour in a $CO_2$ incubator at 37° C. Following incubation, cells were pelleted with 2000 rpm, 5 min, room temperature, then the resulting cell pellets were incubated overnight (5% $CO_2$, 37° C.).

The A549 line was initiated in 1972 by D. J. Giard et al. (1973) through explant culture of lung carcinomatous tissue from a 58-year-old male. A549 cells are adenocarcinomic human alveolar basal epithelial cells. A549 cells fall under the squamous subdivision of epithelial cells. Cells seeded at a concentration of $2 \times 10^4$ cells/cm$^2$ in the above culture medium will be 100% confluent in 5 days.

A549 cells are available at the American Type Culture Collection (ATCC; Rockville, Md.) as CCL-185 and can be grown in Ham's F-12 medium (GIBCO BRL, Grand Island, N.Y.) with 10% fetal calf serum (FCS; GIBCO BRL) or according to recommendations of the supplier.

The WI-38 cell line was developed in 1962 from lung tissue taken from a therapeutically aborted fetus of about 3 months gestational age. Cells released by trypsin digestion of the lung tissue were used for the primary culture. The cell morphology is fibroblast-like. The karyotype is 46,XX; normal diploid female. A maximum lifespan of 50 population doublings for this culture was obtained at the Repository. A thymidine labelling index of 86% was obtained after recovery. G6PD is isoenzyme type B. This culture of WI-38 is an expansion from passage 9 frozen cells obtained from the submitter.

WI-38 cells available at http://www.atcc.org/ATCCAdvancedCatalogSearch/tabid/112/Default.aspx American Type Culture Collection (ATCC; Rockville, Md.) as CCL-75 are grown according to recommendations of the supplier.

CL13 or CL30 cells (Wardlaw et al., 2002) were cultured in Dulbecco's modified Eagles/F12 medium containing 5% fetal calf serum and 25% microg/ml gentamicin.

Human cells are preferably maintained at 37° C. in a humid atmosphere containing $CO_2$ as needed.

Lung Tissue Samples.

Lung tissue samples were collected during routine surgery (lung resections) at the Department of Surgery, University of Pécs, Hungary. Prior to surgery, patients had given informed consent and the project was approved by the Ethical Committee of the University of Pécs. Culturing lung tissue samples in Wnt11 -SN is described in detail in Supplementary methods. Patient data is summarized in table 1)

TABLE 1

| Characteristic | Number of Patients (%) |
| --- | --- |
| Total Number of Patients | 17 (100) |
| Age, years | |
| Mean ± SD | 63.0 ± 9.2 |
| Range | 40-75 |
| Sex | |
| Male | 8 (47.1) |

TABLE 1-continued

| Characteristic | Number of Patients (%) |
|---|---|
| Female | 9 (52.9) |
| Smoking status | |
| Nonsmoker | 11 (64.7) |
| Male | 6 (35.3) |
| Female | 5 (29.4) |
| Smoker | 6 (35.3) |
| Male | 2 (11.8) |
| Female | 4 (23.5) |
| Chronic obstructive pulmonary disease (COPD) | 12 (70.6) |
| Histology | |
| Adenocarcinoma | 9 (52.9) |
| Large-cell carcinoma | 4 (23.5) |
| Planocellular carcinoma | 2 (11.8) |
| Other NSCLC | 2 (11.8) |
| Pathologic stage | |
| I | 8 (47.1) |
| II | 8 (47.1) |
| III | 1 (5.9) |
| Invasion | |
| Vascular invasion | 0 (0.0) |
| Pleural invasion | 2 (11.8) |

Fluorescent and Confocal Microscopy

Prior to 2D and 3D culturing, SAECs, NHLFs and HMVECs were stained with fluorescent physiological dyes CFSE, DiI and DiD, respectively (all from Molecular Probes). Cells were washed twice in PBS and incubated with CFSE, DiI or DiD at the concentration of 0.5 µg/ml at 37° C. for 10 minutes. The excess dyes were removed by washing the cells with DMEM+10% FCS. 2D and 3D cultures were prepared using the fluorescent-labeled cells, as indicated before. After overnight incubation, 3D cell cultures were removed carefully from the V-bottom plates and transferred to coverslip-bottom dishes (MatTek). Lung tissue microcultures were investigated by fluorescent microscopy (Olympus IX-81 microscope) or confocal microscopy (Olympus FV1000 confocal imaging system)

Cell Sorting

SAEC and NHLF were stained with CFSE and DiI according to manufacturers instructions (Molecular probes). Cells were mixed and cultured for 72 hours in 2D and 3D systems. Stained cells were dissociated by mild trypsin treatment followed by PBS+EDTA treatment. Dissociated cells were sorted using a BD FACSVantage cell sorter into tubes with lysis buffer for mRNA preparation (Miltenyi Biotech).

Immunofluorescence

After culturing cells in 3D for 3 days, micro-tissues were carefully removed from the V-bottom plates and fixed in 4% formaline for 10 minutes at room temperature. Fixed samples were covered with TissueTech cryostate embedding medium and 8 µm thick frozen sections were made. Sections were permeabilized in PBS buffer containing 0.1% saponine and 5% BSA for 30 minutes. Primary and secondary antibodies were diluted in the same buffer and incubated with the samples for 1-1 hour. Antibody list is shown in Table 2. Fluorescent images were acquired using an Olympus IX-81 fluorescent microscope. To ensure the comparability of expression levels of SFTPC, AQP3 and N-cad in Wnt11-SN— or Wnt11 siRNA-treated samples to their matched untreated controls, all images were captured with the same exposition settings.

TABLE 2

List of antibodies

| Antigen | Host | type | Manufacturer | Application |
|---|---|---|---|---|
| human Aquaporin 3 | rabbit | polyclonal | Santa Cruz Biotechnology | I.F. |
| human beta-actin | mouse | monoclonal | Sigma-Aldrich | WB |
| human Keratin-7 | mouse | monoclonal | DAKO | I.F. |
| human N-cadherin | mouse | monoclonal | Santa Cruz | I.F. |
| human Pro-surfactant Protein-C | rabbit | polyclonal | Millipore | I.F. |
| human Surfactant Protein-A | rabbit | polyclonal | Millipore | I.F. |
| human Vimentin | mouse | monoclonal | DAKO | I.F. |
| human Wnt11 | rabbit | polyclonal | Abcam | I.F., WB |
| Murine IgG* | donkey | polyclonal | R&D Systems | I.F. |
| Murine IgG* | donkey | polyclonal | R&D Systems | I.F. |
| Rabbit IgG* | donkey | polyclonal | R&D Systems | I.F. |

*NorthernLight NL575 conjugate;
I.F. = Immunofluorescence

Recombinant Adenoviral Vectors

The full gene-of-interest or GFP only sequence was amplified by PCR reaction using Forward (5'): 5'- -3', Reverse (3'): 5'- -3' primer sequences and cloned into the Shuttle vector, then by homologous recombination into the adenoviral vector. Adenovirus was produced by transfecting the linearised plasmid DNA into the 293 packaging cell line (American Type Culture Collection, Rockville, Md.) using Lipofectamine 2000 (Invitrogen). The resulting plaques were amplified, the adenovirus purified and concentrated using the adenoviral purification kit (BD Biosciences).

Adenoviral Infection of Epithelial Cells

Adenovirus containing GFP or gene-of-interest-GFP were added to SAEC in 2D or 3D. $1\times10^6$ cells were resuspended in 250 µl of cell culture medium and 50 µl of virus for 90 minutes at 37° C.

Lentiviral Vectors and Cloning of Wnt11

Constructs. Lentiviral vectors: Lv-CMV-IRES-GFP, Lv-CMV-Wnt11-IRES-GFP

Retrovirus was produced by transfecting the plasmid DNA into the 293A packaging cell line (American Type Culture Collection, Rockville, Md.) using Lipofectamine 2000 (Invitrogen).

Cloning Primers:

```
Wnt11:
Forward: 5'-gaagatcttc atgcgcaccatcgtgcac-3'
(BglII)

Reverse: 5'-gcgtcgacgt tcacttgcagacgtagcg-3'
(SalI)
```

Retroviral infection. Retroviral supernatants were generated from retroviral vectors containing Wnt11-GFP, or green fluorescence protein (GFP) only, in 293 cells. Epithelial cell line A549 was transformed using the above viruses in 24-well-plates, in 250 µl of viral supernatant and 50 µl of DMEM polybrene mix (final conc.: 8 µg/ml)/well, and then centrifuged for 60 min at 2100 rpm at room temperature. The cells were incubated for 3 days in fresh DMEM containing 10% FCS, then sorted based on GFP expression using FACSVantage cell sorter (BD Biosciences). GFP positive cells were then cultured as described above. The presence of Wnt11 protein were verified by immunoblotting and immunofluorescence using Wnt11 specific polyclonal antibody (AbCam) (FIG. 7).

CXCL-8 Assay

CXCL-8 (IL-8) content of 2D and 3D cell culture supernatants was measured with Quantikine CXCL-8/IL-8 ELISA kit (R&D Systems). The sandwich ELISA assay was performed according to the manufacturer's instructions. Briefly, identically diluted cell culture supernatant samples and CXCL-8 standards were dispensed onto the wells pre-coated with anti-CXCL-8 monoclonal antibody. After 2 hours incubation at room temperature, the plate was washed 4 times with the provided washing buffer. Then HRPO-conjugated polyclonal anti-CXCL-8 antibody was added for one hour. After a final washing step, TMB substrate solution was added to the wells. The optical density was determined with an iEMS Reader MF (Thermo Labsystems) at 450 and 570 nm and data were analyzed using Ascent software.

Data Quantitation

Quantitative real-time RT-PCR data were analyzed by the delta Ct (dCt) and Relative Quantity (RQ) methods as suggested by Applied Biosystems using 7500 System SDS Software. All samples were set up in duplicates. Briefly, Ct values were determined for each sample using an automatic threshold level determined by the 7500 SDS Software. Delta Ct (dCt) values were determined according to the following formula: dCt(target gene)=Ct(target gene)–Ct(housekeeping gene). Changes in gene expression are shown as RQ values calculated using the next formula: $RQ=2^{-ddCt}$, where ddCt values were calculated as $ddCt=dCt(sample)-dCt(reference\ sample)$.

CXCL-8 content of the cell culture supernatants were determinded by comparing the OD to a standard curve calculated from 7 different concentrations in the range of 31.2-2000 pg/ml CXCL-8. Samples were dispensed in duplicates and the means were used for further data analysis.

Statistical Analysis

Statistical comparisons were made using paired t test where it was applicable.

TABLE 3

| Abbr. | Official gene name | Accesion No. | No[1] | Forward primer sequence | No[1] | Reverse primer sequence | Length[4] |
|---|---|---|---|---|---|---|---|
| AQP3 | H. sapiens aquaporin 3 | NM_004925 | 1 | AGCCCCTTCAGGATTTCCA | 2 | GACCCAAATTCCGGTTCCA | 86 |
| AQP4 | H. sapiens aquaporin 4 | NM_001650 | 3 | GCGAGGACAGCTCCTATGAT | 4 | ACTGGTGCCAGCATGAATC | 110 |
| AQP5 | H. sapiens aquaporin 5 | NM_001651 | 5 | CCTTGCGGTGGTCATGA | 6 | ATGGGGCCCTACCCAGAAAAC | 61 |
| b-act1[2] | H. sapiens beta actin | NM_001101 | 7 | CTGTGCTATCCCTGTACGCCTCTG | 8 | GTGATCTCCTTCTGCATCCTGTCG | 541 |
| b-act2[3] | H. sapiens beta actin | NM_001101 | 9 | GCGCGGCTACAGCTTCA | 10 | CTTAATGTCACGCACGATTTCC | 55 |
| E-cad | H. sapiens cadherin 1 | NM_004360 | 11 | GACCGGTGCAATCTTCAAA | 12 | TTGACGCCGAGAGCTACAC | 93 |
| IL-1b | H. sapiens interleukin 1, beta | NM_000576 | 13 | TCAGCCAATCTTCATTGCTCAA | 14 | TGGCGAGCTCAGGTACTTCTG | 62 |
| IL-6 | H. sapiens interleukin 6 | NM_000600 | 15 | AGGGCTCTTCGGCAAATGTA | 16 | GAAGGAATGCCCATTAACAACAA | 62 |
| KRT7 | H. sapiens keratin 7 | NM_005556 | 17 | CCACCCACAATCACAAGAAGATT | 18 | TCACTTTCCAGACTGTCTCACTGTCT | 78 |
| N-cad | H. sapiens cadherin 2 | NM_001792 | 19 | AGCTTCTCACGGCATACACC | 20 | GTGCATGAAGGACAGCCTCT | 133 |
| S100A4 | H. sapiens S100 Ca binding protein A4 | NM_002961 | 21 | TGGAGAAGGCCCTG | 22 | CCCTCTTTGCCCGAGTACTTG | 58 |
| SFTPA1 | H. sapiens surfactant protein A1 | NM_005411 | 23 | CCCCTTGTCTGCAGGATTT | 24 | ATCCCTGGAGAGTGTGGAGA | 128 |
| SFTPB | H. sapiens surfactant protein B | NM_198843 | 25 | GCACTTTAAAGGACGGTGTCTT | 26 | GATGCCCACACCACCTG | 128 |
| SFTPC | H. sapiens surfactant protein C | NM_003018 | 27 | AAAGTCCACAACTTCCAGATGGA | 28 | CCTGGCCCAGCTTAGACGTA | 73 |
| SLUG | H. sapiens snail homolog 2 | NM_003068 | 29 | CAGACCCTGGTTGCTTCAA | 30 | TGACCTGTCTGCAAATGCTC | 121 |
| TTF-1 | H. sapiens NK2 homeobox 1 (NKX2.1) | NM_003317 | 31 | CATGTCGATGAGTCCAAAGCA | 32 | GCCCACTTTCTTGTAGCTTTCC | 85 |

TABLE 3-continued

| Abbr. | Official gene name | Accession No. | No[1] | Forward primer sequence | No[1] | Reverse primer sequence | Length[4] |
|---|---|---|---|---|---|---|---|
| Wnt11 | H. sapiens wingless-type MMTV integration site family, member 11 | NM_004626 | 33 | CGTTGGATGTCTTGTTGCAC | 34 | TGACCTCAAGACCCGATACC | 209 |

[1]SEQ ID NO:
[2]beta-actin1
[3]beta-actin2
[4]Product length

Example 2

Experiments for Development of a 3D Lung Tissue Model

Hanging Drop Model

To simulate human lung structure, we started with a 3D cell aggregate of 100 000 cells, in roughly equal amounts of distinct fibroblast (NHLF) and small airway epithelial cell populations (SAEC), randomly intermixed. Within a day of incubation in a hanging drop assay, the cells generated loose tissue structures. The formation, however, was not stable and was not possible to transfer the generated micro-tissues from the initial culture conditions to another test plate without irrecoverable damage to the tissue structure.

Pelleted, Matrigel Containing Model

To improve the stability of mixed lung micro-tissues, 1:1 ratio of SAEC and NHLF were pelleted and grown in the presence of matrigel. Many 3D lung and other tissue models use matrigel to create a 3D structure where various cell types can grow and interact with one another. SAECs and NHLFs were stained with a fluorescent physiological dyes DiI (Honig and Hume 1989) and CFSE (Wang, Duan et al. 2005) to be able to follow cellular movements in culture. Cells and matrigel were pipetted into V-bottom, 96-well, non-tissue culture treated plates and left for one hour in a $CO_2$ incubator at 37° C. Following incubation, cells were pelleted with 2000 rpm, 5 min, room temperature, then the resulting cell pellets were incubated overnight (5% $CO_2$, 37° C.).

Figure 1:
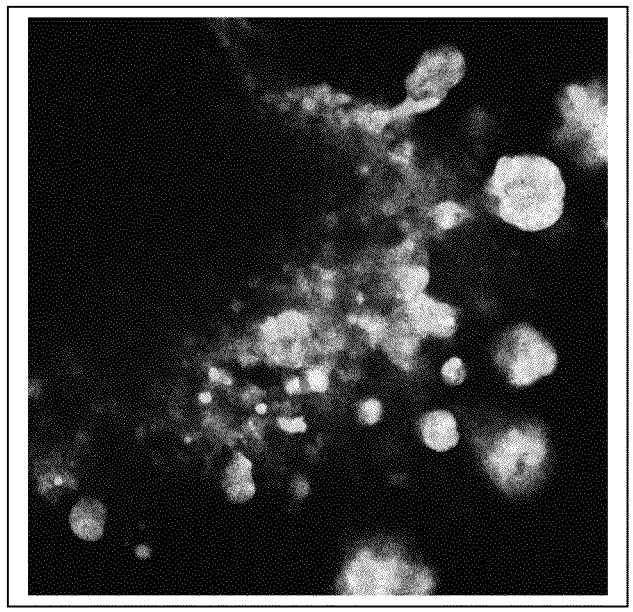
FIG. 1. Matrigel based culture of 50% SAEC and 50% NHLF mix

On FIG. 1 a matrigel based culture of 50% SAEC and 50% NHLF mix is shown. It is apparent that, despite the presence of matrigel, SAEC and NHLF were unable to form stable 3D structures. Furthermore, it appeared that small spherical tissue structures containing mostly epithelial cells were leaving the tissue/matrigel mass.

Example 3

Pelleted, Artificial Tissue Scaffold Free Model

As a next step in simulating 3D culture conditions of the human lung, the random mix of equal number of epithelial cells (SAEC) and fibroblasts (NHLF) were pelleted without matrigel in two stages. Cells were pipetted into V-bottom, 96-well, non-tissue culture treated plates and left for one hour in a $CO_2$ incubator at 37° C. Following incubation, cells were pelleted with 2000 rpm, 5 min, room temperature, then the resulting cell pellets were incubated overnight (5% $CO_2$, 37° C.). Cells prior to mixed culturing were stained using 1:1000 dilutions in PBS (phosphate buffer saline pH 7.2) of physiological fluorescent dyes of DiI (1 mg/ml stock in DMSO) and CFSE (1 mg/ml stock in DMSO). In these culture conditions cells formed a stable aggregate, where the most adhesive fibroblast (red or dark gray) were surrounded by those of the less adhesive epithelial cell type (green or light grey) (FIG. 2). The aggregate diameter is about 200 µm.

In a further experiment, the ratio of SAEC and NHLF cells was systematically changed and cultures were prepared using the following SAEC:NHLF ratios, respectively: 0/100%; 25/75%, 50/50%, 75/25, 100/0%, otherwise as described above. On FIG. 2 the pelleted micro-tissue cultures containing different ratios of SAEC and NHLF are shown. As evidenced by the figure, the most pronounced 3D structure aggregates with a surface epithelial cell lining were formed when equal amount of epithelial and fibroblasts cells were applied, aggregates have a fair epithelial cell lining albeit are somewhat smaller and less convincing in morphology at a ratio of 25/75%, whereas a much more even epithelial lining is formed at an excess of SAEC cells, i.e. when the ratio of cell epithelial cells and fibroblasts is 75/25%. Pure cultures either do not form aggregates of 3D structure (epithelial cells) or the aggregates are much smaller in size (fibroblast cells).

Example 4

Characterization of the Two Cell Type Tissue Scaffold-Free 3D Pulmonary Tissue Model Differentiation Markers Molecular characterization of the model was based on epithelial differentiation markers using real-time PCR analysis. mRNA was purified from the cell aggregates and cDNA was generated. Using TTF1 (FIG. 4a), AQ3 (FIG. 4b) and AQ5 specific primers, results were analysed relative to beta-actin as internal control.

On FIG. 4a. mRNA levels of TTF-1 in 3D human lung micro-tissues are indicated. TTF1 transcription factor is a characteristic marker of alveolar epithelial cells. While 3D fibroblast cultures show no TTF1 expression, TTF1 is present in 3D SAEC monocultures and increased in 2D SAEC/NHLF co-cultures indicating the beneficial effect of fibroblasts. The highest level of TT1 expression was reached in 3D SAEC/NHLF tissues.

Figure 4:
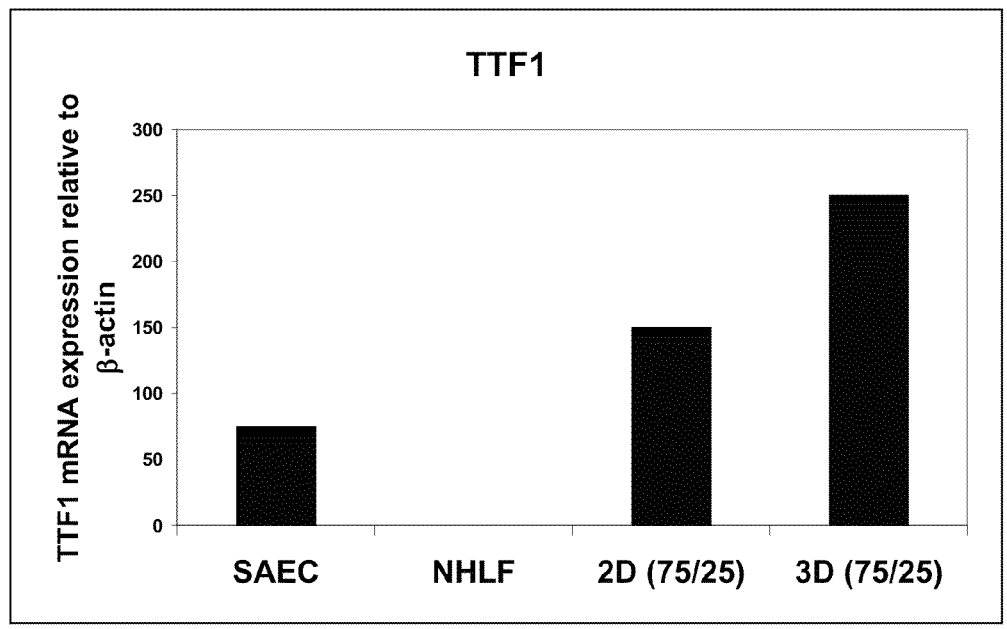
FIG. 4. mRNA expression levels of marker proteins in human lung microtissue cultures.
Figure 4:
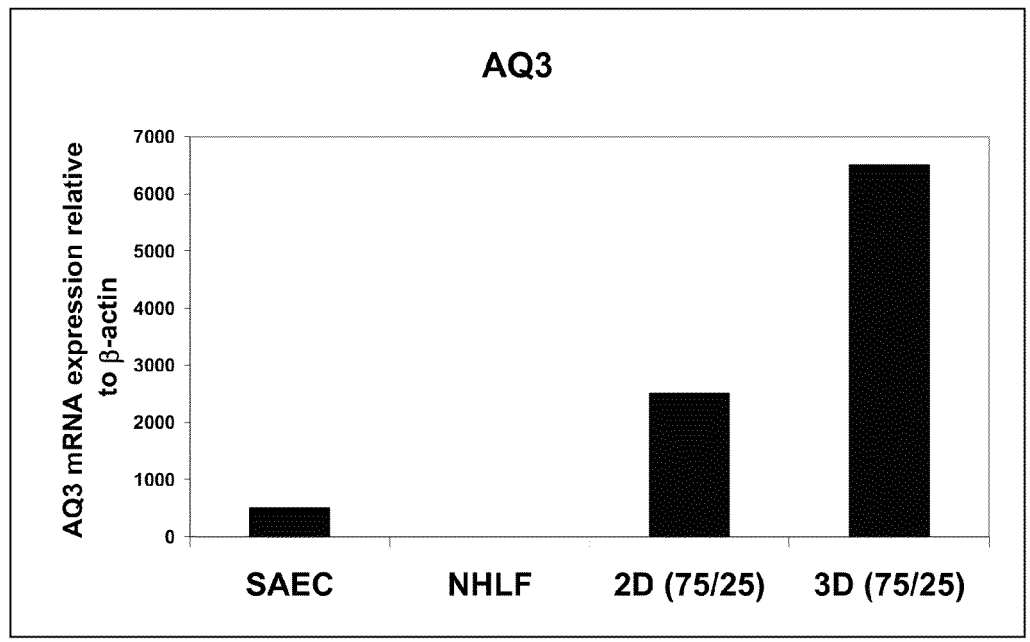
Figure 4:
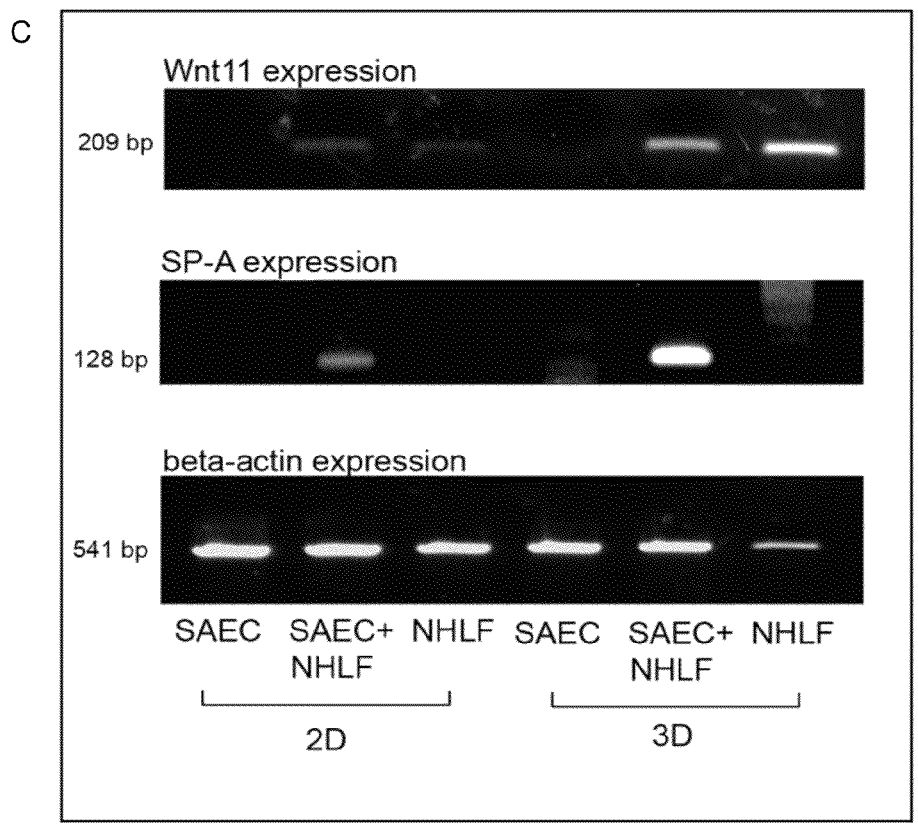
Figure 4:
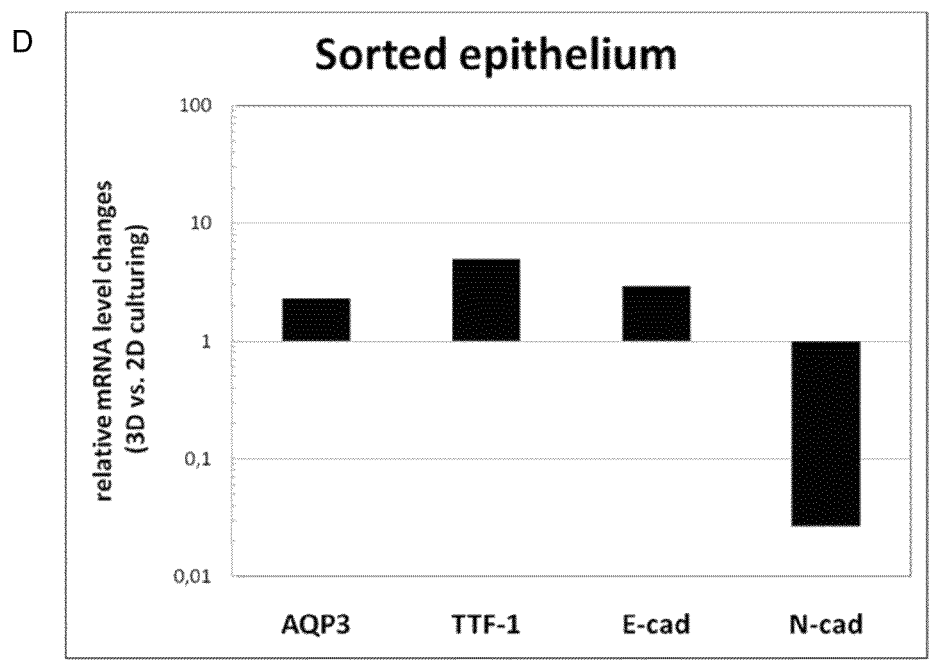

FIG. 4b. shows mRNA levels of AQP-3 water transporter in 3D human lung micro-tissues. AQ3 is an ATII epithelial type marker in the lung. While 3D fibroblast cultures show no AQ3 expression, AQ3 is present in 3D SAEC monocultures and increased in 2D SAEC/NHLF co-cultures indicating the beneficial effect of fibroblasts, but the highest level of AQ3 was still observed in 3D SAEC/NHLF tissue cultures. Thus, the above markers indicated an inducible increase in ATII type differentiation that was further supported by no increase in ATI type marker expressions. The purified differentiated cell types we used in the experiments were obtained from commercial sources. Although these cell types originated from differentiated tissues, once they were purified and kept in 2D culture conditions the cells have shown almost immediate signs of dedifferentiation indicated by increased level of S100A4 (FIG. 5.d and Table 2). Once SAEC was co-cultured with NHLF, S100A4 and N-cadherin levels decreased significantly, while the E-cadherin levels increased. The "cadherin-switch" [Zeisberg M and E. G. Neilson (2009)] was more prominent in 3D than in 2D culture conditions (FIG. 4.d and FIGS. 5.e and f) indicating that apart from the presence of NHLF, the 3D structure was also necessary to decrease dedifferentiation of SAEC. These changes are also a feature of epithelial-mesenchymal transition (EMT), characteristic for the epithelial dedifferentiation process.

Pro-inflammatory Cytokine Expression

As triggered by pulmonary infection or alveolar epithelial injury (disruption of continuous epithelial cell layer) pro-inflammatory cytokines are produced by the alveolar epithelium to attract inflammatory cells, including neutrophils. To test CXCL-8 pro-inflammatory cytokine expression, CXCL-8 protein levels were tested from cellular supernatants of 2D mono and co-cultures and 3D tissue co-cultures, set up as seen in FIG. 2. Using a commercially available ELISA test kit (R&D Laboratories) it has become apparent that CXCL-8 expression levels were significantly reduced in 3D tissue systems compared to conventional 2D tissue cultures (FIG. 6.a) and the lowest levels were detected where epithelial cell ratios were the highest, implicating that CXCL-8 expression is triggered by discontinuation in epithelial cell layers.

On the diagram on FIG. 6.a CXCL-8 secretion is shown in a human, in vitro, 3D lung model. It was found that 3D monocultures of fibroblasts secreted no CXCL-8, while 3D SAEC still produced the cytokine, (although to a lesser degree than 2D SAEC cultures—data not shown). 2D co-cultures didn't significantly alter CXCL-8 expression, indicating, that the presence of fibroblasts cannot influence cytokine expression. CXCL-8 expression levels were significantly reduced in 3D tissue system where 75/25% was the epithelial-fibroblast ratio, where epithelial cells essentially fully covered the fibroblast sphere, implicating that CXCL-8 expression can be triggered by discontinuation in the alveolar epithelial cell layer. This reduction in CXCL-8 expression was somewhat less pronounced at a ration of 50/50% and 25/75%.

Inflammatory cytokines IL-1beta and IL-6 mRNA levels were also investigated using quantitative real time RT-PCR analysis. In 3D cultures compared to the respective 2D cultures, both IL-1beta and IL-6 mRNA levels were significantly down-regulated (FIGS. 6B and 6C, respectively), when the PCR was performed from the mix of SAEC-NHLF mRNA. Once SAEC cells were sorted out from 2D and 3D NHLF co-cultures, decreased expression of IL-1beta and IL-6 in SAEC cultured in 3D conditions was even more striking (FIG. 6D).

Example 5

Effect of Wnt11 on Marker Expression of the 3D Model

Using qRT-PCR, lung epithelial differentiation markers including Thyroid transcription factor (TTF-1) [Ikeda K. et al., (1995)], Aquaporins (AQP) [Kreda S. M. and Gynn M. C., (2001)] and Surfactant proteins (SFTP) [Dobbs, L. G. (1989)] were analyzed in AECs purified from the 3D model and were compared with AECs cultured in traditional two-dimensional (2D) SAEC, 3D SAEC and 2D co-cultures. Progressive de-differentiation from type II characteristics of purified SAEC was detected in 2D and 3D but not in 3D co-cultures. As type II marker Surfactant Protein A (SFTPA) (FIG. 4.C) was regained in 2D co-culture models, the presence of NHLF was confirmed as an important component of type II differentiation. Marked increase in other type II differentiation markers was only detected, when SAECs were incubated in the presence of NHLF in a 3D system (FIG. 4) highlighting the importance of the 3D structure.

In contrast to traditional 2D cultures where de-differentiation manifests by up-regulation of EMT10 markers, suppression of EMT was found in the 3D model, as down-regulation of de-differentiation markers were detected by testing S100A4, E- and N-cadherin mRNA levels by qRT-PCR and/or histology (FIG. 4.D and FIG. 5).

Moreover, immuno-fluorescence analysis demonstrated a radical increase in pro-SFTPC protein (FIGS. 12E and 12F) expression with additional up-regulation of AQP3 and E-cadherin and the parallel down-regulation of EMT markers11 (S100A4, N-cadherin and SLUG) in the Wnt11 treated cultures (FIG. 5.D-F and FIG. 8.E-I). PCR studies demonstrated a significant increase in SFTPA mRNA levels (FIG. 15).

Example 5

Three-cell Type Model with Epithelial, Endothelial and Fibroblast Components

To further improve the complexity our lung tissue culture model we added primary human lung-derived microvascular endothelial cells (HMVEC) to SAEC and NHLF cells and set up 2D and 3D tissue micro-cultures similarly to the SAEC and NHLF co-cultures.

Morphological examination of the micro-tissues by fluorescent and confocal microscopy revealed, that HMVECs could successfully be co-cultured with both SAEC and NHLF cells in 3D conditions (FIG. 10.a). Interestingly, in co-cultures with either SAEC or NHLF, HMVECs formed the inner, compact core of the micro-cultures. When the three cell types (1:1:1) were cultured together in 3D conditions, they adhered together and formed a markedly compact and stable 3D structure (FIG. 10.b).

Molecular characterization of three-cell cultures revealed that the level of AQP3 and KRT7 expression increased remarkably in 3D cultures compared to that of measured in 2D culture conditions (FIG. 10.a and Table 2). The level of EMT markers S100A4 and N-cad were increasing when cells were kept in 2D cultures, but stabilized in 3D cultures. The slight decrease of E-cad in 3D cultures was less than detected in 2D culture conditions (FIG. 10.a and Table 2). As the quantitative RT-PCR was performed from the mixed mRNA of the three cell types, further analysis of the three cell type 3D cultures is required, however, to discover the optimal proportions of the three cell types that would aid tissue building from purified tissue elements.

Table 4 shows gene expression changes in human primary lung cell cultures. Numbers are RQ values, calculated according to the formula $RQ = 2^{-ddCt}$, where ddCt values were calculated as ddCt=dCt(sample) dCt(reference sample). Except for Sorted SAEC, where data are presented as dCt values, calculated as follows: dCt=Ct(target gene)−Ct(housekeeping gene). A part of collected cells before the set-up of the various cultures were used always as reference samples. Delta Ct (dCt) values were calculated as follows: dCt(target gene)=Ct (target gene)−Ct(housekeeping gene). 18S ribosomal RNA was used as housekeeping gene, except in case of Sorted SAEC saples, where actin was used as housekeeping gene.

TABLE 4

| | 2 dimensional cultures | | | | |
|---|---|---|---|---|---|
| Gene | SAEC only | SAEC-NHLF | SAEC-NHLF-HMVEC | NHLF only | Sorted SAEC** |
| AQP3 | 6.890182077 | 11.40487803 | 0.271602751 | 0.674274063 | 9.771933 |
| AQP4 | N.D. | N.D. | N.A. | N.D. | N.C. |
| AQP5 | N.C. | N.C. | N.A. | N.C. | N.C. |
| E-cad | 2.409657267 | 1.772261436 | 0.215508996 | N.D. | 7.976 |
| IL-1b | 5.728006854 | 29.60546927 | N.A. | N.D. | 4.6346 |
| IL-6 | 5.189026016 | 28.09596712 | N.A. | 0.807285548 | 7.425867 |
| KRT7 | 4.851098336 | 7.462934362 | 2.181196885 | N.D. | −1.46075 |
| N-cad | 0.527520842 | 1.111301286 | 9.374683602 | 0.132931047 | 6.17955 |
| S100A4 | 2.536012377 | 0.421634905 | 1.860860619 | 0.380836664 | 8.929833 |
| SFTPA1 | N.D.* | Low* | N.D.* | N.D.* | N.A. |
| SFTPB | N.D. | N.C. | N.D. | N.D. | N.A. |
| SFTPC | N.D. | N.C. | N.D. | N.D. | N.A. |
| TTF-1 | 1.023345722 | 0.863026227 | N.A. | N.D. | 10.351 |

| | 3 dimensional cultures | | | | |
|---|---|---|---|---|---|
| Gene | SAEC only | SAEC-NHLF | SAEC-NHLF-HMVEC | NHLF only | Sorted SAEC** |
| AQP3 | 5.78456172 | 13.31255896 | 3.62800556 | 2.854211675 | 8.571433 |
| AQP4 | N.C. | N.C. | N.A. | N.D. | N.C. |
| AQP5 | N.C. | N.C. | N.A. | N.C. | N.C. |
| E-cad | 0.644138229 | 3.016491578 | 0.296617715 | N.D. | 6.4226 |
| IL-1b | 0.667615932 | 2.016755678 | N.A. | N.D. | 5.7802 |
| IL-6 | 0.114404135 | 8.323721329 | N.A. | 0.498089943 | 10.67543 |
| KRT7 | 1.34235123 | 3.684848466 | 3.765852951 | N.D. | 0.4287 |
| N-cad | 0.05583254 | 0.095682573 | 1.244810959 | 0.056255969 | 11.4096 |
| S100A4 | 2.03353463 | 0.415210465 | 1.050573185 | 0.157182738 | 6.653067 |
| SFTPA1 | N.D.* | High* | N.D.* | N.D.* | N.A. |
| SFTPB | N.C. | N.C. | N.D. | N.D. | N.A. |
| SFTPC | N.C. | N.C. | N.D. | N.D. | N.A. |
| TTF-1 | 0.926426355 | 1.059201358 | N.A. | N.D. | 8.034067 |

Abbreviations: N.A.: data are not available, expression level was not determined.
N.D.: No specific PCR product was detected with real-time QPCR.
N.D.*: No specific PCR product was detected with conventional PCR.
N.C.: Specific expression levels were not consequent in parallel wells or samples with real-time QPCR.
Low*: Relatively low expression levels were detected by conventional PCR.
High*: Relatively high expression levels were detected with conventional PCR.

Summary of Results with Cellular Markers and Factors Secreted by the Cells

Here we provide evidence that 3D co-culturing of primary pulmonary epithelial cells with fibroblasts is more advantageous for SAEC to maintain a more differentiated status than in either 2D or 3D in vitro monocultures. Inclusion of NHLFs not only facilitated epithelial differentiation but the cohesion and structure of the 3D micro-tissues were much more firm and compact compared to SAEC-only (FIG. 2) or SAEC-HMVEC (FIG. 10.a) cultures.

TTF1 transcription factor is a characteristic general marker of alveolar epithelial cells during embryonic development and after birth in ATII cells. Cytokeratins are components of the intermediate filaments of the cytoskeleton and their expression patterns are important in cell lineage identification. In our experiments, lung epithelial markers TTF-1 and cytokeratin 7 KRT7 showed elevated expression levels in 3D co-cultures.

Type II pneumocytes facilitate transepithelial movement of water (via members of the aquaporin protein (AQP) family). ATII marker Aquaporin 3 show elevated levels in the presence of fibroblasts (FIG. 5) Secretion of surfactant proteins is a unique feature of ATII lung epithelial cells. [Dobbs, L. G. (1989), Alcorn, J. L., et al., (1997) ] In our experiments, SAEC cells in monocultures failed to express surfactant proteins, while surfactant protein A1 mRNA was consequently expressed in 3D and at a lesser amount in 2D co-cultures. (FIG. 4.c) However, surfactant proteins B and C were not consequently detectable in our 3D co-culture systems (data not shown). We also examined the expression of ATI markers Aquaporin 4 and 5 in both 2-cell and 3-cell cultures, but the expression of these molecules was not consequently detectable, either, presumably because the cells (SAEC) used herein are rather of the ATII type. Moreover, a considerable amount of time is needed for ATI differentiation (data not shown). During a somewhat longer culturing time, if cells with ATI type characteristics are used, ATI markers would appear.

Thus, except of SFPC, differentiation markers AQP3, KRT7, TTF1 and SFPA were up-regulated in the presence of fibroblasts. Levels of AQP3 and SFTPA but not KRT7 or TTF1 differentiation markers were further increased in 3D culture conditions.

S100A4 is a well-known molecular marker for epithelial-mesenchymal transition and the level of its expression is often high in metastatic carcinomas [Sherbet, G. V et al. 2009] as well as in lung fibrosis [Guarino, M. et al., 2009]. Up-regulation of S100A4 and N-cadherin and parallel down-regulation of E-cadherin [Zeisberg, M. and E. G. Neilson, (2009), Seike, M., et al., (2009)] are also features of epithelial-mesenchymal transition (EMT), that is characteristic for the epithelial dedifferentiation process and is characterized by loss of cell adhesion, repression of E-cadherin expression, and increased cell mobility.

De-differentiation markers S100A4 and N-cadherin appeared in purified primary cells in 2D culture conditions.

The above de-differentiation markers decreased in the presence of fibroblasts and further decreased in 3D conditions.

Decrease of inflammatory markers including IL1b, IL6 and CXCL8 could be observed in 3D cultures in comparison with 2D cultures. Said markers were significantly down-regulated in 3D culture conditions; the mere presence of fibroblasts, e.g. in 2D cultures, were not sufficient to decrease their levels.

SFTPA1 expression was observed in 2-cell but not in 3-cell cultures. (FIG. 4.c and data not shown).

Example 6

Disease Models

Lung Tumor Models from Lung Tumor Cell Lines.

Artificial 3D lung tissue culture is prepared as described in Example 3 with the following modification.

Instead of epithelial cells (SAEC) a combination of type II alveolar epithelial cells (A549) and 5-20% of CL13 or CL30 cells (Wardlaw et al., Molecular Pharmacology, 62, 326-333 2002), derived from NNK [4-(methylnitrosamino)-1-(3-pyridal)-1-butanone] treated A/J mouse, a model of lung adenocarcinoma [Belinsky et al. (1992)] is used. CL13 or CL30 cells carry mutations of the Ki-ras gene.

A series of experiment is performed to find appropriate ratio of A549 cells and CL13 or CL30 cells. A ratio when tumor is spontaneously formed is used to prepare a 3D lung model tissue, which is used as a lung tumor disease model.

In an alternative of the above method patient tumor cells are used.

Lung Tumor Model Prepared by Suppression of Wnt11 Expression

Suppression of Wnt11 expression in the pulmonary model was achieved by transduction of NHLF with Wnt11 specific siRNA.

2×105 NHLF cells per well were cultured overnight in FGM-2 serum free medium (Lonza) in 6-well plates before transfection. 100 ng of Cy3-conjugated negative control siRNA or Wnt11 siRNA (Negative control siRNA No. 1 and Wnt11-specific siRNA No. 15011, both from Ambion) were transfected per well using Lipofectamine 2000 reagent according to the manufacturer's recommendations (Invitrogen). After 4 hours, the efficiency of siRNA transfection was checked by visualizing Cy3 fluorescence of the cells using a fluorescent microscope (Olympus IX81). Then cells were trypsinized and 2D and 3D cultures were set up as described previously.

Down-regulation of Wnt11 coincided with up-regulation of S100A4, N-cadherin and SLUG as EMT and down-regulation of alveolar differentiation marker AQP3 (FIG. 12). The epithelial cells appeared more flattened and cuboid-like cells were no longer abundant (FIG. 12.A-12.D).

To confirm the theory behind this model, primary cancer tissues were also examined for Wnt11 expression. We theorized that if Wnt11 was able to inhibit EMT marker up-regulation in lung model studies, Wnt11 levels might decrease as EMT markers increase as the disease progresses. To investigate, a cohort of NSCLCs samples (n=17) was collected during lung surgery, then levels of Wnt11 and its receptor Frizzled (Fz)-7 were screened using qRT-PCR. In NSCLC samples both Wnt11 and Fz-7 were down-regulated compared to their autologous controls obtained from non-malignant lung parenchyma (FIG. 13.A, FIG. 13.B).

Modification of Secreted Factor Composition in Primary Cell Aggregates Using Genetically Modified and Sub-Lethally Irradiated Cell Lines All cell types are left non-infected, gene expressions therefore are as normal as in any given 3D lung tissue model. Cellular composition of the aggregates however contains sub-lethally irradiated cells (5-10% of total cell number of the aggregate)—either fibroblast (WI-38) or alveolar epithelial (A549) cell lines that are genetically modified and produce secreted factors (Wnt-s, Bone Morphogenic Protein (BMP)-s, inflammatory and pro-inflammatory cytokines, growth factors, etc) that modify the cellular microenvironment within the aggregates.

Native 3D Pulmonary Cell Aggregates

To mimic inflammatory conditions, native 3D pulmonary cell aggregates are treated with various concentrations of bacterial cell wall extracts. Cytokine production is determined using cytokine specific ELISA techniques from tissue culture media, gene expression changes both in epithelial and fibroblasts can be quantified by real-time PCR reactions.

Example 7

3D Lung Tissue Kit

In this example a test-ready 3C lung tissue kit of the following features is prepared (FIG. 14):
1. Test-ready lung tissue is delivered in 96 well plates.
2. Small (80 000 cells/well) samples of lung model tissue, ready for experiments or tests, are present in the wells.
3. Each tissue consists of a mixed culture of human primary alveolar epithelium and fibroblasts (25, 50 and 75% epithelium respectively).
4. The plate contains 3-3 wells of controls (epithelium and fibroblasts only).
5. The plates are sealed with a transparent, preferably adhesive, plastic foil, e.g. with Saranrap.

The quality of tissue is guaranteed for three days, including delivery.

The plate itself is a 96, V-bottom well, non-adhesive tissue culture plate.

The model tissue is prepared as described in EXAMPLE 3. Each tissue is submerged in 200 microliter of tissue culture medium, optimal for lung culture in 5% $CO_2$ environment, sealed and delivered at room temperature or on ice. Quality control: one tissue is taken from each well and viability is tested. The differentiation markers are tested by real-time PCR. On request, a 2D control plate (tissue grown in 96-well, flat-bottom, adhesive tissue culture plate) can be included to accompany the 3D tissue.

Example 8

Treatment

An animal model with acute lung tissue injury [Matute-Bello, G et al. (2008)] is treated with an inhalable aerosol composition of purified Wnt11 prepared in accordance with usual formulation methods. A concentration series of Wnt11 protein is applied and tissue injury healing is studied ad disclosed by Matute-Bello, G, above.

Industrial Applicability

Above, basic parameters and culture conditions are established for an ATII-type tissue scaffold free lung model, where spontaneous self-assembly of cells and cellular interactions can be studied. The model allows easy handling and genetic manipulation of complex tissue systems in both theoretical and applied research and in pharmaceutical testing. The model is also easily expanded by additional cell types to include endothelial cell for vascularization and even smooth muscle cells, where further reciprocal tissue and cellular interactions can be studied. Treatment by an ATII differentiation marker renders the model very similar to distal airways.

The scaffold-free 3D culturing allows trouble-free genetic manipulation of simple or more complex tissue systems in either theoretical or applied research and in pharmaceutical testing. Based on the above model and using various gene delivery methods and variable target genes, our 3D human pulmonary micro-tissue model system is easily adaptable to study genetic changes during pulmonary diseases that can lead to identification of novel drug targets and development of novel therapies. These disease models may include inflammatory models, tumor model, lung fibrosis model, or a regeneration model.

3D models of healthy lung tissue as well as disease tissues are available. The product according to the invention can be marketed e.g. in the form of tissue cultures, plates or arrays comprising such cultures or kits.

The model presented herein allows easy handling, and a simple experimental setup and a relatively short culturing time are sufficient. Moreover, no complex laboratory equipment is required. The present system is appropriate for use with human cells, including human primary cells and non-transformed human cells.

REFERENCES

Akiri, G. et al. (2009) Wnt pathway aberrations including autocrine Wnt activation occur at high frequency in human non-small-cell lung carcinoma. Oncogene 28, 2163-2172

Alcorn, J.L., et al., (1997). Primary Cell Culture of Human Type II Pneumonocytes: Maintenance of a Differentiated Phenotype and Transfection with Recombinant Adenoviruses. Am. J. Respir. Cell Mol. Biol., 17(6): p. 672-682.

Belinsky et al., (1992). Role of the alveolar type II cell in the development and progression of pulmonary tumors induced by 4-(methylnitrosamino)- 1 -(3 -pyridyl)- 1 -butanone in the A/J mouse. Cancer Res. 52 3164-3173

Bellusci, S., J. Grindley, et al. (1997). "Fibroblast growth factor 10 (FGF10) and branching morphogenesis in the embryonic mouse lung."Development. 124(23): 4867-4878.

Bruno, M. D., R. J. Bohinski, et al. (1995). "Lung cell-specific expression of the murine surfactant protein A (SP-A) gene is mediated by interactions between the SP-A promoter and thyroid transcription factor-i."J.Biol.Chem. 270: 653 1-6536.

Cardoso, W. V. (2001). "Molecular regulation of lung development."Annu Rev Physiol. 63: 47 1-494.

Colvin, J. S., A. C. White, et al. (2001). "Lung hypoplasia and neonatal death in Fgf9-null mice identify this gene as an essential regulator of lung mesenchyme."Development 128(11): 2095-2106.

Colvin, J. S., B. Feldman, et al. (1999). "Genomic organization and embryonic expression of the mouse fibroblast growth factor 9 gene."Dcv Dyn. 216W: 72-88.

Dc Moerlooze, L., B. Spencer-Dene, et al. (2000). "An important role for the 11Th isoform of fibroblast growth factor receptor 2 (FGFR2) in mesenchymal-epithelial signalling during mouse organogenesis."Development 127(3): 483-492.

Dobbs, L.G. (1989) Pulmonary Surfactant. Annual Review of Medicine 40, 43 1-446

Giard D. J. et al. (1973). In vitro cultivation of human tumors: establishment of cell lines derived from a series of solid tumors. J. NatI. Cancer Inst. [Bethesda] 51: 1417-1423

Guarino, M., A. Tosoni, and M. Nebuloni, (2009). Direct contribution of epithelium to organ fibrosis: epithelial-mesenchymal transition. Human Pathology, 40(10): p. 1365-1376.

Hare, K.J., E. J. Jenicinson, and G. Anderson, (1999). In vitro models of T cell development. Seminars in Immunology, 11(1): p. 3-12.

Honig, M. G. and R. I. Hume (1989). "Dil and diO: versatile fluorescent dyes for neuronal labelling and pathway tracing."Trends Neurosci. 12(9): 333-335.

Hughes Tracy et al., a poster presented at National Center for Replacement, Refinement and Reduction of animals in Research, Showcasing the 3Rs Portcullis House, 28 February 2007

Ikeda, A., J. C. Clark, et al. (1995). "Gene structure and expression of human thyroid transcription factor-i in respiratory epithelial cells."J. Biol.Chem. 270: 8108-8114.

Innovative Medicine Research Initiative Strategic Research Agenda. 2008, European Technology Platform.

Königshoff, M., et al., (2008). Functional Wnt Signaling Is Increased in Idiopathic Pulmonary Fibrosis. PLoS ONE, 3(5): p. e2142.

Kramer, J.A., J.E. Sagartz, and DL. Morris, (2007). The application of discovery toxicology and pathology towards the design of safer pharmaceutical lead candidates. Nat Rev Drug Discov, 6(8): p. 636-b649.

Krause DS, (2001) Cell, 105:369-377

Kreda, SM., Gynn, MC., Fenstermacher, D.A., Boucher, R.C. & Gabriel, SE. (2001) Expression and localization of epithelial aquaporins in the adult human lung. Am. J. Respir. Cell. Mol. Biol. 24, 224 -234

Lazzaro, D., M. Price, et al. (1991). "The transcription factor, TTF-1, is expressed at the onset of thyroid and lung morphogenesis and in restricted regions of the foetal brain-."Development 113: 1093-1104.

Matute-Bello, G et al. (2008) Animal models of acute lung injury Am J Physiol Lung Cell Mol Physiol 295: L379-L399

Min, H., D. M. Danilenko, et al. (1998). "Fgf-lO is required for both limb and lung development and exhibits striking functional similarity to Drosophila branchless."Genes Dcv. 12(20): 3156-3161.

Napolitano, AP, Chai, P et al. (2007). "Dynamics of the self-assembly of complex cellular aggregates on micromolded nonadhesive hydrogels."Tissue Eng. 13(8): 2087-94.

Neagu, A. (2006). "Computational Modeling Of Tissue Self-Assembly."Modern Physics Letters B 20: 1207-123 1.

Nichols, J.E. and J. Cortiella, (2008). Engineering of a Complex Organ: Progress Toward Development of a Tissue-engineered Lung. Proc Am Thorac Soc,. 5(6): p. 723 -730.

Ornitz, D. M. and N. Itoh (2001). "Fibroblast growth factors-."Genome Biol. 2(3): 3005.

Seike, M., et al., (2009). Epithelial to Mesenchymal Transition of Lung Cancer Cells. Journal of Nippon Medical Scool, 76(4): p. 181-181.

Sekine, K., H. Ohuchi, et al. (1999). "FgflO is essential for limb and lung formation."Nat Genet. 21(1): 138-141.

Shannon, J. M. and B. A. Hyatt (2004). "Epithelial-Mesenchymal Interactions in the Developing Lung."Annual Review of Physiology 66: 625-645.

Sherbet, G.V., (2009). Metastasis promoter 5100A4 is a potentially valuable molecular target for cancer therapy. Cancer Letters, 280(1): p. 15-30.

Vertrees, RA, Zwischenberger, JB et al. (2008) "Cellular differentiation in three-dimensional lung cell cultures-."Cancer Biol Ther. Mar; 7(3): 404-12.

Voulgari, A. & Pintzas, (2009).A. Epithelial-mesenchymal transition in cancer metastasis: Mechanisms, markers and strategies to overcome drug resistance in the clinic. Biochimica et Biophysica Acta (BBA) -Reviews on Cancer 1796, 75-90

Wang, X. Q., H. Li, et al. (2009) "Oncogenic K-Ras Regulates Proliferation and Cell Junctions in Lung Epithelial Cells through Induction of Cyclooxygenase-2 and Activation of Metalloproteinase-9"Molecular Biology of the Cell 20, 791-800.

Wang, X. Q., X. M. Duan, et al. (2005). "Carboxyfluorescein Diacetate Succinimidyl Ester Fluorescent Dye for Cell Labeling."Acta Biochimica Biophysica Sinica 37(6): 379-385.

Wardlaw et al., (2002). Transcriptional regulation of basal cyclooxygenase-2 expression... Molecular Pharmacology, 62, 326-333

Yang, M. C., Y. Guo, et al. (2006). "The TTF-1/TAP26 complex differentially modulates surfactant protein-B (SP-B) and -C (SP-C) promoters in lung cells."Biochem Biophys Res Commun. 344(2): 484-490.

Zeisberg, M. & Neilson, E.G. (2009) Biomarkers for epithelial-mesenchymal transitions. The Journal of Clinical Investigation 119, 1429-143 7

Zhang, X., T. S. Stappenbeck, et al. (2005). "Reciprocal epithelial-mesenchymal FGF signaling is required for cecal development."Development. 133: 173-180.

The invention claimed is:

1. An engineered three dimensional pulmonary model tissue culture, wherein said model tissue culture
   a) is free of any artificial tissue scaffold,
   b) comprises cultured pulmonary fibroblasts,
   c) comprises cultured pulmonary small airway epithelial cells, and
   d) has a morphology of one or more cellular aggregate(s), each aggregates comprising a multiplicity of cavities,
   wherein the pulmonary small airway epithelial cells express at least one alveolar type II (ATII) epithelial differentiation marker and wherein the cells are in direct cell-cell contact with cells of one or more other types of the tissue culture, and
   wherein said pulmonary small airway epithelial cells and pulmonary fibroblasts comprise cultured primary cells obtained from a subject.

2. The engineered three dimensional pulmonary model tissue culture according to claim 1 wherein the pulmonary small airway epithelial cells and pulmonary fibroblasts are connected by increased adhesion as compared to a control two dimensional single cell culture or a control two dimensional co-culture and wherein the ratio of the pulmonary small airways epithelial cells and the pulmonary fibroblasts in the model tissue is at least 1:6 and at most 6:1.

3. The engineered three dimensional pulmonary model tissue culture according to claim 1, wherein
   said model tissue culture comprises cells de-differentiated before culturing and re-differentiated upon culturing.

4. The engineered three dimensional pulmonary model tissue culture according to claim 1, wherein said model tissue culture is obtained by
   preparing a mixed suspension of at least pulmonary small airway epithelial cells and pulmonary fibroblast cells, pelleting the cells of the suspension,
incubating the pelleted suspension in the presence of $CO_2$, and
exposing the model tissue culture to a regulator of ATII type differentiation, and wherein
the model tissue culture comprises cuboid-like epithelial pulmonary cells.

5. The engineered three dimensional pulmonary model tissue culture according to claim 4 wherein the regulator of ATII type differentiation is Wnt11.

6. The engineered three dimensional pulmonary model tissue culture according to claim 1, wherein
   a) at least one alveolar epithelial cell (AEC) marker is up-regulated, and/or
   b) at least one inflammation marker is down-regulated, and/or
   c) epithelial-mesenchymal transition (EMT) is inhibited, and/or
   d) at least one EMT marker is down-regulated.

7. The engineered three dimensional pulmonary model tissue culture according to claim 1, wherein in said model tissue culture
   at least one of the following ATII markers are up-regulated:
   a surfactant protein,
   aquaporin 3 (AQP3),
   thyroid transcription factor-1 (TTF1).

8. The engineered three dimensional pulmonary model tissue culture according to claim 1, wherein said model tissue culture comprises affected cells having a pathologic feature of a diseased lung tissue.

9. The engineered three dimensional pulmonary model tissue culture according to claim 8, wherein Wnt11 is silenced, down-regulated or knocked-out in the cells of said model tissue culture and thereby the model tissue culture shows EMT features typical of a tumor.

10. The engineered three dimensional pulmonary model tissue culture according to claim 8, wherein the model is an inflammatory model and the disease involves inflammation and the affected cells express inflammatory cytokines above normal level.

11. The engineered three dimensional pulmonary model tissue culture according to claim 10 wherein the cytokines, expressed by the cells, determine an inflammatory response.

12. The engineered three dimensional pulmonary model tissue culture according to claim 8, wherein
   the disease is a tumor and the cells are transformed or immortal cells and the model is a tumor model,
   the disease involves fibrosis and the model is a fibrosis model, or
   the disease involves injury of the tissue and the model is a regeneration model.

13. The engineered three dimensional pulmonary model tissue culture according to claim 8, wherein the model is a tumor model, wherein said tumor model is a non-small cell lung cancer model.

14. The engineered three dimensional pulmonary model tissue culture according to claim 8, wherein the affected cells are obtained from a patient donor.

15. The engineered three dimensional pulmonary model tissue culture according to claim 8, wherein the affected cells are tumorous cells obtained from a patient.

16. The engineered three dimensional pulmonary model tissue culture according to claim 1 said model tissue culture also comprising a mammalian pulmonary cell comprising an expression cassette carrying a gene encoding a Wnt11 protein, said cell being capable of expressing said Wnt11 protein for use in alveolar tissue regeneration, lung tissue injury repair or in the treatment of a condition selected from lung tissue injury, acute lung injury, pulmonary fibrosis, airway and interstitial pulmonary fibrosis, chronic fibrosis including asbestosis, sarcoidosis and idiopathic pulmonary fibrosis, pneumonitis, diseases causing airflow obstruction, and chronic obstructive pulmonary disease (COPD).

17. The engineered three dimensional pulmonary model tissue culture according to claim 1 wherein at least one type of cells of said model tissue culture express Wnt11.

18. The engineered three dimensional pulmonary model tissue culture according to claim 1 wherein the surface of the aggregates is enriched in the pulmonary small airway epithelial cells, and wherein the pulmonary small airway epithelial cells and the pulmonary fibroblast cells are at least partially segregated in said aggregates.

19. The engineered three dimensional pulmonary model tissue culture according to claim 1, wherein
   the ATII differentiation marker is a surfactant protein selected from surfactant protein C (SFPC), pro surfactant protein C (pro-SFTPC), and surfactant protein A (SFPA);
   at least one of the following EMT markers is down-regulated: S 100 Ca binding protein A4 (S 100A4), N-cadherin, and snail homolog 2 (SLUG); and
   E-cadherin is up-regulated.

20. The engineered three dimensional pulmonary model tissue culture according to claim 1 wherein the pulmonary epithelial cells and/or the fibroblasts are obtained from a patient donor.

21. An engineered three dimensional pulmonary model tissue kit comprising a test plate having an array of containers wherein at least two containers contain
   samples of one or more types of engineered three dimensional pulmonary model tissue cultures as defined in claim 1, each sample placed in separate containers of said plate,
   an appropriate medium for culturing cells of the model tissue cultures.

22. A method for the preparation of the engineered three dimensional pulmonary model tissue culture of claim 1, said method comprising the steps of
   preparing a mixed suspension of at least pulmonary small airway epithelial cells and pulmonary fibroblast cells, wherein said pulmonary epithelial cells and pulmonary fibroblasts comprise cultured primary cells obtained from a subject,
   pelleting the cells of the suspension, and
   incubating the pelleted suspension in the presence of $CO_2$, for a time sufficient for the cells to form a three dimensional pulmonary model tissue culture comprising one or more cellular aggregate(s),
   wherein each of said aggregates comprises a multiplicity of cavities and is free of any artificial tissue scaffold,
   and wherein in the aggregates the epithelial cells express at least one alveolar type II (ATII) epithelial differentiation marker,
   and wherein the cells are in direct cell-cell contact with cells of one or more other types of the tissue culture.

23. The method according to claim 22, wherein
   said mixed suspension of at least pulmonary small airway epithelial cells and pulmonary fibroblast cells comprises cells de-differentiated before culturing and the cells are re-differentiated upon culturing.

24. The method according to claim 22, wherein cells of the culture are exposed to or contacted with Wnt11.

25. The method according to claim 22 also comprising the step of assaying the model tissue culture for a feature selected from
- a) expression of one or more ATII type epithelial differentiation markers characteristic to model tissue culture, wherein an increased expression level as compared to a reference culture is considered as indicative of the formation of a three dimensional pulmonary model tissue culture;
- b) expression of one or more pro-inflammatory cytokines wherein a decreased expression level as compared to a suitable reference culture is considered as indicative of the formation of a three dimensional pulmonary model tissue culture;
- c) at least one EMT marker, wherein a decreased expression level as compared to a suitable reference culture is considered as indicative of the formation of a three dimensional pulmonary model tissue culture; and
- d) morphology of the one or more aggregate(s).

26. A method for screening of a drug for its effect on lung tissue, said method comprising the steps of
- providing an engineered three dimensional pulmonary model tissue culture as defined in claim 1,
- taking at least a test sample and a reference sample of said model tissue culture,
- contacting the test sample with a drug while maintaining the test sample and the reference sample under the same conditions,
- detecting any alteration or modification of the test sample in comparison with the reference sample wherein if any alteration or modification of the test sample is detected it is considered as an indication of the effect of the drug.

\* \* \* \* \*

```
                        SEQUENCE LISTING

<160> NUMBER OF SEQ ID NOS: 36

<210> SEQ ID NO 1
<211> LENGTH: 19
<212> TYPE: DNA
<213> ORGANISM: Artificial Sequence
<220> FEATURE:
<223> OTHER INFORMATION: Forward primer for AQP3

<400> SEQUENCE: 1
agccccttca ggatttcca                                                     19

<210> SEQ ID NO 2
<211> LENGTH: 19
<212> TYPE: DNA
<213> ORGANISM: Artificial Sequence
<220> FEATURE:
<223> OTHER INFORMATION: Reverse primer for AQP3

<400> SEQUENCE: 2
gacccaaatt ccggttcca                                                     19

<210> SEQ ID NO 3
<211> LENGTH: 20
<212> TYPE: DNA
<213> ORGANISM: Artificial Sequence
<220> FEATURE:
<223> OTHER INFORMATION: Forward primer for AQP4

<400> SEQUENCE: 3
gcgaggacag ctcctatgat                                                    20

<210> SEQ ID NO 4
<211> LENGTH: 19
<212> TYPE: DNA
<213> ORGANISM: Artificial Sequence
<220> FEATURE:
<223> OTHER INFORMATION: Reverse primer for AQP4

<400> SEQUENCE: 4
actggtgcca gcatgaatc                                                     19

<210> SEQ ID NO 5
<211> LENGTH: 17
<212> TYPE: DNA
<213> ORGANISM: Artificial Sequence
<220> FEATURE:
<223> OTHER INFORMATION: Forward primer for AQP5

<400> SEQUENCE: 5
ccttgcggtg gtcatga                                                       17
```

```
<210> SEQ ID NO 6
<211> LENGTH: 21
<212> TYPE: DNA
<213> ORGANISM: Artificial Sequence
<220> FEATURE:
<223> OTHER INFORMATION: Reverse primer for AQP5

<400> SEQUENCE: 6
atggggccct acccagaaaa c                                              21

<210> SEQ ID NO 7
<211> LENGTH: 24
<212> TYPE: DNA
<213> ORGANISM: Artificial Sequence
<220> FEATURE:
<223> OTHER INFORMATION: Forward primer for beta-actin 1

<400> SEQUENCE: 7
ctgtgctatc cctgtacgcc tctg                                           24

<210> SEQ ID NO 8
<211> LENGTH: 24
<212> TYPE: DNA
<213> ORGANISM: Artificial Sequence
<220> FEATURE:
<223> OTHER INFORMATION: Reverse primer for beta-actin 1

<400> SEQUENCE: 8
gtgatctcct tctgcatcct gtcg                                           24

<210> SEQ ID NO 9
<211> LENGTH: 17
<212> TYPE: DNA
<213> ORGANISM: Artificial Sequence
<220> FEATURE:
<223> OTHER INFORMATION: Forward primer for beta-actin 2

<400> SEQUENCE: 9
gcgcggctac agcttca                                                   17

<210> SEQ ID NO 10
<211> LENGTH: 22
<212> TYPE: DNA
<213> ORGANISM: Artificial Sequence
<220> FEATURE:
<223> OTHER INFORMATION: Reverse primer for beta-actin 2

<400> SEQUENCE: 10
cttaatgtca cgcacgattt cc                                             22

<210> SEQ ID NO 11
<211> LENGTH: 19
<212> TYPE: DNA
<213> ORGANISM: Artificial Sequence
<220> FEATURE:
<223> OTHER INFORMATION: Forward primer for E-cad

<400> SEQUENCE: 11
gaccggtgca atcttcaaa                                                 19

<210> SEQ ID NO 12
<211> LENGTH: 19
<212> TYPE: DNA
<213> ORGANISM: Artificial Sequence
<220> FEATURE:
```

<223> OTHER INFORMATION: Reverse primer for E-cad

<400> SEQUENCE: 12
ttgacgccga gagctacac                                                    19

<210> SEQ ID NO 13
<211> LENGTH: 22
<212> TYPE: DNA
<213> ORGANISM: Artificial Sequence
<220> FEATURE:
<223> OTHER INFORMATION: Forward primer for IL-1b

<400> SEQUENCE: 13
tcagccaatc ttcattgctc aa                                                22

<210> SEQ ID NO 14
<211> LENGTH: 21
<212> TYPE: DNA
<213> ORGANISM: Artificial Sequence
<220> FEATURE:
<223> OTHER INFORMATION: Reverse primer for IL-1b

<400> SEQUENCE: 14
tggcgagctc aggtacttct g                                                 21

<210> SEQ ID NO 15
<211> LENGTH: 20
<212> TYPE: DNA
<213> ORGANISM: Artificial Sequence
<220> FEATURE:
<223> OTHER INFORMATION: Forward primer for IL-6

<400> SEQUENCE: 15
agggctcttc ggcaaatgta                                                   20

<210> SEQ ID NO 16
<211> LENGTH: 23
<212> TYPE: DNA
<213> ORGANISM: Artificial Sequence
<220> FEATURE:
<223> OTHER INFORMATION: Reverse primer for IL-6

<400> SEQUENCE: 16
gaaggaatgc ccattaacaa caa                                               23

<210> SEQ ID NO 17
<211> LENGTH: 23
<212> TYPE: DNA
<213> ORGANISM: Artificial Sequence
<220> FEATURE:
<223> OTHER INFORMATION: Forward primer for KRT7

<400> SEQUENCE: 17
ccacccacaa tcacaagaag att                                               23

<210> SEQ ID NO 18
<211> LENGTH: 26
<212> TYPE: DNA
<213> ORGANISM: Artificial Sequence
<220> FEATURE:
<223> OTHER INFORMATION: Reverse primer for KRT7

<400> SEQUENCE: 18
tcactttcca gactgtctca ctgtct                                            26

```
<210> SEQ ID NO 19
<211> LENGTH: 20
<212> TYPE: DNA
<213> ORGANISM: Artificial Sequence
<220> FEATURE:
<223> OTHER INFORMATION: Forward primer for N-cad

<400> SEQUENCE: 19
agcttctcac ggcatacacc                                               20

<210> SEQ ID NO 20
<211> LENGTH: 20
<212> TYPE: DNA
<213> ORGANISM: Artificial Sequence
<220> FEATURE:
<223> OTHER INFORMATION: Reverse primer for N-cad

<400> SEQUENCE: 20
gtgcatgaag gacagcctct                                               20

<210> SEQ ID NO 21
<211> LENGTH: 14
<212> TYPE: DNA
<213> ORGANISM: Artificial Sequence
<220> FEATURE:
<223> OTHER INFORMATION: Forward primer for S100A4

<400> SEQUENCE: 21
tggagaaggc cctg                                                     14

<210> SEQ ID NO 22
<211> LENGTH: 21
<212> TYPE: DNA
<213> ORGANISM: Artificial Sequence
<220> FEATURE:
<223> OTHER INFORMATION: Reverse primer for S100A4

<400> SEQUENCE: 22
ccctctttgc ccgagtactt g                                             21

<210> SEQ ID NO 23
<211> LENGTH: 19
<212> TYPE: DNA
<213> ORGANISM: Artificial Sequence
<220> FEATURE:
<223> OTHER INFORMATION: Forward primer for SFTPA1

<400> SEQUENCE: 23
ccccttgtct gcaggattt                                                19

<210> SEQ ID NO 24
<211> LENGTH: 20
<212> TYPE: DNA
<213> ORGANISM: Artificial Sequence
<220> FEATURE:
<223> OTHER INFORMATION: Reverse primer for SFTPA1

<400> SEQUENCE: 24
atccctggag agtgtggaga                                               20

<210> SEQ ID NO 25
<211> LENGTH: 22
<212> TYPE: DNA
<213> ORGANISM: Artificial Sequence
<220> FEATURE:
<223> OTHER INFORMATION: Forward primer for SFTPB
```

```
<400> SEQUENCE: 25
gcactttaaa ggacggtgtc tt                                              22

<210> SEQ ID NO 26
<211> LENGTH: 17
<212> TYPE: DNA
<213> ORGANISM: Artificial Sequence
<220> FEATURE:
<223> OTHER INFORMATION: Reverse primer for SFTPB

<400> SEQUENCE: 26
gatgcccaca ccacctg                                                    17

<210> SEQ ID NO 27
<211> LENGTH: 23
<212> TYPE: DNA
<213> ORGANISM: Artificial Sequence
<220> FEATURE:
<223> OTHER INFORMATION: Forward primer for SFTPC

<400> SEQUENCE: 27
aaagtccaca acttccagat gga                                             23

<210> SEQ ID NO 28
<211> LENGTH: 20
<212> TYPE: DNA
<213> ORGANISM: Artificial Sequence
<220> FEATURE:
<223> OTHER INFORMATION: Reverse primer for SFTPC

<400> SEQUENCE: 28
cctggcccag cttagacgta                                                 20

<210> SEQ ID NO 29
<211> LENGTH: 19
<212> TYPE: DNA
<213> ORGANISM: Artificial Sequence
<220> FEATURE:
<223> OTHER INFORMATION: Forward primer for SLUG

<400> SEQUENCE: 29
cagaccctgg ttgcttcaa                                                  19

<210> SEQ ID NO 30
<211> LENGTH: 20
<212> TYPE: DNA
<213> ORGANISM: Artificial Sequence
<220> FEATURE:
<223> OTHER INFORMATION: Reverse primer for SLUG

<400> SEQUENCE: 30
tgacctgtct gcaaatgctc                                                 20

<210> SEQ ID NO 31
<211> LENGTH: 21
<212> TYPE: DNA
<213> ORGANISM: Artificial Sequence
<220> FEATURE:
<223> OTHER INFORMATION: Forward primer for TTF-1

<400> SEQUENCE: 31
catgtcgatg agtccaaagc a                                               21

<210> SEQ ID NO 32
<211> LENGTH: 22
```

```
<212> TYPE: DNA
<213> ORGANISM: Artificial Sequence
<220> FEATURE:
<223> OTHER INFORMATION: Reverse primer for TTF-1

<400> SEQUENCE: 32
gcccactttc ttgtagcttt cc                                            22

<210> SEQ ID NO 33
<211> LENGTH: 20
<212> TYPE: DNA
<213> ORGANISM: Artificial Sequence
<220> FEATURE:
<223> OTHER INFORMATION: Forward primer for Wnt11

<400> SEQUENCE: 33
cgttggatgt cttgttgcac                                               20

<210> SEQ ID NO 34
<211> LENGTH: 20
<212> TYPE: DNA
<213> ORGANISM: Artificial Sequence
<220> FEATURE:
<223> OTHER INFORMATION: Reverse primer for Wnt11

<400> SEQUENCE: 34
tgacctcaag acccgatacc                                               20

<210> SEQ ID NO 35
<211> LENGTH: 28
<212> TYPE: DNA
<213> ORGANISM: Artificial Sequence
<220> FEATURE:
<223> OTHER INFORMATION: Forward primer for Wnt11 cloning

<400> SEQUENCE: 35
gaagatcttc atgcgcacca tcgtgcac                                      28

<210> SEQ ID NO 36
<211> LENGTH: 28
<212> TYPE: DNA
<213> ORGANISM: Artificial Sequence
<220> FEATURE:
<223> OTHER INFORMATION: Reverse primer for Wnt11 cloning

<400> SEQUENCE: 36
gcgtcgacgt tcacttgcag acgtagcg                                      28
```